US 7,485,425 B2
Feb. 3, 2009

(12) United States Patent
Spier

(10) Patent No.: US 7,485,425 B2
(45) Date of Patent: Feb. 3, 2009

(54) METHODS FOR AMPLIFICATION OF NUCLEIC ACIDS USING SPANNING PRIMERS

(75) Inventor: Eugene G. Spier, Palo Alto, CA (US)

(73) Assignee: Applied Biosystems Inc., Foster City, CA (US)

( * ) Notice: Subject to any disclaimer, the term of this patent is extended or adjusted under 35 U.S.C. 154(b) by 0 days.

(21) Appl. No.: 11/542,584

(22) Filed: Oct. 2, 2006

(65) Prior Publication Data

US 2007/0128632 A1  Jun. 7, 2007

Related U.S. Application Data

(60) Provisional application No. 60/723,579, filed on Oct. 3, 2005.

(51) Int. Cl.
 *C12Q 1/68* (2006.01)
 *C12P 19/34* (2006.01)
 *C07H 21/04* (2006.01)

(52) U.S. Cl. .............. 435/6; 435/91.2; 536/24.31; 536/24.32; 536/24.33

(58) Field of Classification Search .............. 435/6, 435/91.2; 536/24.31, 24.32, 24.33
See application file for complete search history.

(56) References Cited

U.S. PATENT DOCUMENTS

| 6,797,474 | B2 * | 9/2004 | Lizardi | 435/6 |
| 6,812,005 | B2 * | 11/2004 | Fan et al. | 435/91.2 |
| 2004/0110134 | A1 * | 6/2004 | Wenz et al. | 435/6 |

OTHER PUBLICATIONS

Lizardi et al., "Mutation detection and single-molecule counting using isothermal rolling-circle amplification," Nature Genetics, 19: 225-232 (1998).

* cited by examiner

*Primary Examiner*—Suryaprabha Chunduru
(74) *Attorney, Agent, or Firm*—Finnegan, Henderson Farabow, Garrett & Dunner, LLP; Lin Sun-Hoffman

(57) ABSTRACT

Methods and kits for detecting whether target nucleic acid sequences are present and/or quantitating target nucleic acid sequences are provided.

25 Claims, 18 Drawing Sheets
(11 of 18 Drawing Sheet(s) Filed in Color)

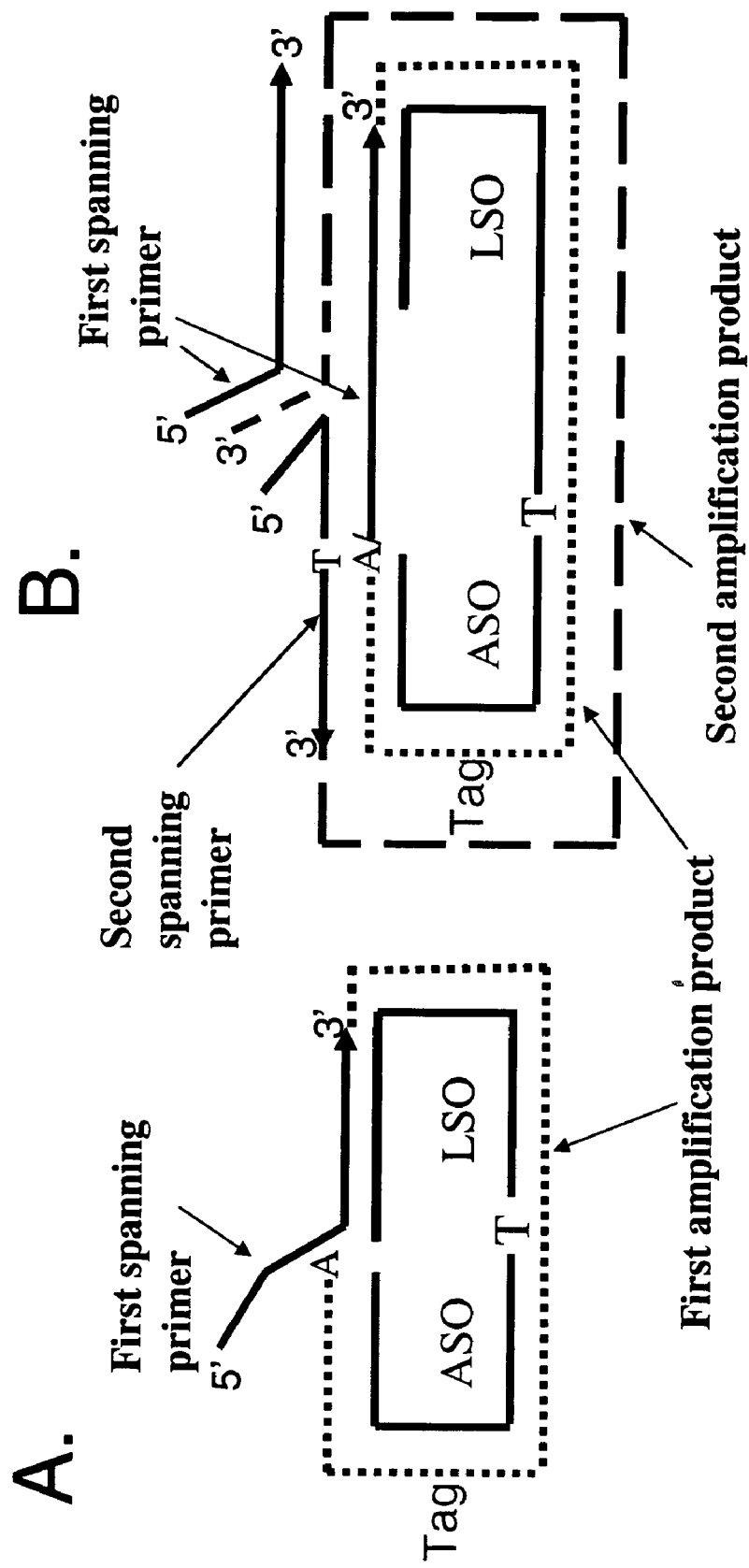

SEQUENCE LISTING

```
<160> NUMBER OF SEQ ID NOS: 4

<210> SEQ ID NO 1
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
tcgtacgtgg tggtgcgggc ctg                                              23
```

-continued

```
<210> SEQ ID NO 2
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
aggccaggtg caggcccgca ccaccaccgc t                                        31

<210> SEQ ID NO 3
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
aaccacgtac gatcgcacca ccaccg                                              26

<210> SEQ ID NO 4
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
agcggtggtg gtgcgatcgt acgtggtggt gcgggcctg                                39
```

METHODS FOR AMPLIFICATION OF NUCLEIC ACIDS USING SPANNING PRIMERS

This application claims the benefit of U.S. Provisional Application No. 60/723,579, filed Oct. 3, 2005, which is incorporated by reference herein for any purpose.

FIELD

The teachings relate to methods and kits for the amplification of target nucleic acids.

BACKGROUND

The detection of the presence or absence of (or quantity of) one or more target nucleic acid sequences in a sample containing one or more target nucleic acid sequences is commonly practiced. For example, the detection of cancer and many infectious diseases, such as AIDS and hepatitis, routinely includes screening biological samples for the presence or absence of diagnostic nucleic acid sequences. Also, detecting the presence or absence of nucleic acid sequences is often used in forensic science, paternity testing, genetic counseling, and organ transplantation. Certain amplification reactions are useful in certain research, diagnostic, medical, forensic and industrial fields. In certain instances, an amplification reaction generates amplification products for use in downstream assays. In certain instances, an amplification reaction generates reaction products for forensic or diagnostic purposes.

SUMMARY

A method for amplifying at least one target nucleic acid sequence is provided, comprising:
  forming an amplification reaction composition comprising:
    a target nucleic acid sequence;
    a polymerase;
    a first primer comprising (i) a sequence complementary to the 5' end of the target nucleic acid sequence and (ii) a sequence complementary to the 3' end of the target nucleic acid sequence; and
  subjecting the amplification reaction composition to at least one amplification reaction to form at least one amplification product.

A method for determining whether at least one target nucleic acid sequence is present in a sample is provided, comprising:
  forming a ligation reaction composition comprising the sample, and a ligation probe set for each target nucleic acid sequence, the probe set comprising (a) a first probe, comprising a first target-specific portion, and (b) a second probe, comprising a second target-specific portion, wherein the probes in each set are suitable for ligation together when hybridized adjacent to one another on the complementary target nucleic acid sequence;
  forming a first test composition by subjecting the ligation reaction composition to at least one cycle of ligation, wherein adjacently hybridizing complementary probes are ligated to one another to form a ligation product comprising the first probe and the second probe;
  forming an amplification reaction composition comprising:
    at least some of the first test composition;
    a polymerase;
    a first primer comprising (i) a sequence complementary to the 5' end of the ligation product and (ii) a sequence complementary to the 3' end of the ligation product;
  forming a second test composition by subjecting the amplification reaction composition to at least one amplification reaction, wherein the second test composition comprises at least one amplification product if a target nucleic acid sequence is present in the sample; and
  determining whether the at least one target nucleic acid sequence is present by detecting at least one amplification product.

A method for determining whether at least one target nucleic acid sequence is present in a sample is provided, comprising:
  (a) forming a reaction composition comprising:
    the sample;
    a ligation probe set for each target nucleic acid sequence, the probe set comprising (i) at least one first probe, comprising a first target-specific portion and (ii) at least one second probe, comprising a second target-specific portion,
    wherein the probes in each set are suitable for ligation together to form a ligation product when hybridized adjacent to one another on a complementary target nucleic acid sequence;
    a polymerase; and
    a first primer comprising (i) a sequence complementary to the 5' end of the ligation product and (ii) a sequence complementary to the 3' end of the ligation product;
  (b) subjecting the reaction composition to at least one cycle of ligation, wherein adjacently hybridizing complementary probes are ligated to one another to form a ligation product comprising the first probe and the second probe;
  (c) after the at least one cycle of ligation, subjecting the reaction composition to at least one amplification reaction to form at least one amplification product if a target nucleic acid sequence is present in the sample; and
  (d) determining whether the at least one target nucleic acid sequence is present by detecting at least one amplification product.

A kit for amplifying at least one target nucleic acid sequence is provided, comprising a polymerase and a first primer comprising (i) a sequence complementary to the 5' end of the target nucleic acid sequence and (ii) a sequence complementary to the 3' end of the target nucleic acid sequence.

A kit for amplifying at least one target nucleic acid sequence is provided, comprising:
  a ligation probe set for each target nucleic acid sequence, the probe set comprising (a) a first probe, comprising a first target-specific portion, and (b) a second probe, comprising a second target-specific portion, wherein the probes in each set are suitable for ligation together when hybridized adjacent to one another on a complementary target sequence, a polymerase, and a first primer comprising (i) a sequence complementary to the 5' end of the target nucleic acid sequence and (ii) a sequence complementary to the 3' end of the target nucleic acid sequence.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The skilled artisan will understand that the drawings, described below, are for illustration purposes only. The figures are not intended to limit the scope of the teachings in any way.

In FIG. 2A, a first spanning primer (110) hybridizes to both the 3' and the 5' ends of a target nucleic acid sequence (120). In the presence of a polymerase (130), the first spanning primer is elongated to form a first amplification product (140). A second spanning primer (210) hybridizes to both the 3' end of the first amplification product (140) and to any portion of the first spanning primer. The second spanning primer (210) is elongated by the polymerase (130) to form a polynucleotide comprising the target nucleic acid sequence with the addition of the second spanning primer at its 5' end (220). FIG. 2B depicts the same method as FIG. 2A, except that the second spanning primer (210) hybridizes to both the 3' end of the first amplification product (140) and to the 5' end of the first spanning primer, which is incorporated into the first amplification product (140).

FIGS. 8A and 8B show certain exemplary embodiments of amplifying a ligation product using first and second spanning primers.

DETAILED DESCRIPTION OF CERTAIN EXEMPLARY EMBODIMENTS

Figure 1:
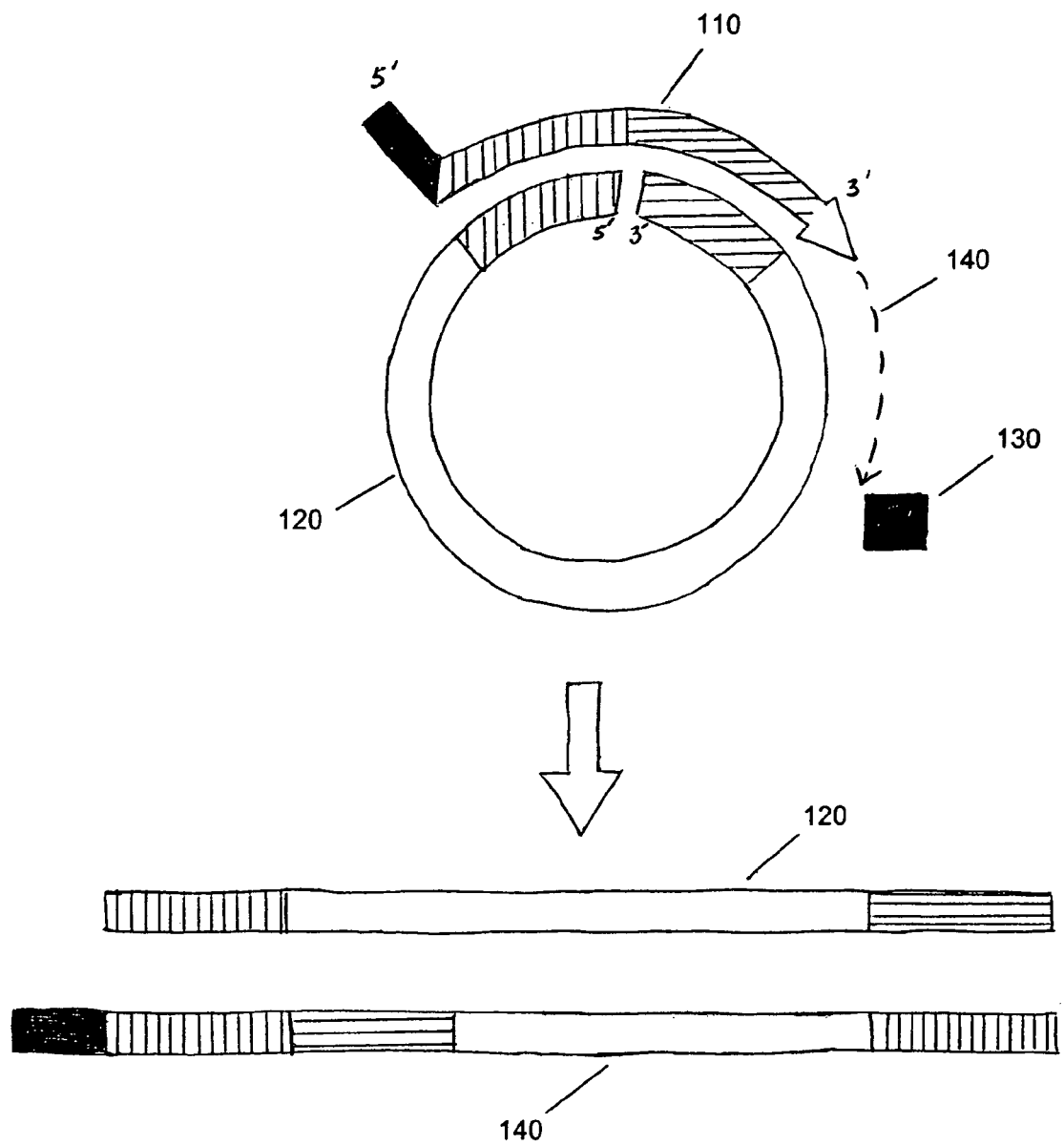
FIG. 1 is a schematic diagram depicting a method of linear amplification of a target nucleic acid sequence using a spanning primer according to certain embodiments. A spanning primer (110) hybridizes to both the 3' and the 5' end of a target nucleic acid sequence (120). In the presence of a polymerase (130), the spanning primer is elongated to form a first amplification product (140).

In this application, the use of the singular includes the plural unless specifically stated otherwise. In this application, the word "a" or "an" means "at least one" unless specifically stated otherwise. In this application, the use of "or" means "and/or" unless stated otherwise. In this application, the meaning of the phrase "at least one" is equivalent to the meaning of the phrase "one or more." Furthermore, the use of the term "including", as well as other forms, such as "includes" and "included", is not limiting. Also, terms such as "element" or "component" encompass both elements and components comprising one unit and elements and components that comprise more than one subunit unless specifically stated otherwise.

The section headings used herein are for organizational purposes only and are not to be construed as limiting the subject matter described. All documents cited in this application, including but not limited to patents, patent applications, articles, books, and treatises, are hereby expressly incorporated by reference in their entirety for any purpose. In the event that one or more of the documents incorporated by reference defines a term that contradicts that term's definition in this application, this application controls.

Certain Definitions

The term "nucleotide base", as used herein, refers to a substituted or unsubstituted aromatic ring or rings. In certain embodiments, the aromatic ring or rings contain at least one nitrogen atom. In certain embodiments, the nucleotide base is capable of forming Watson-Crick and/or Hoogsteen hydrogen bonds with an appropriately complementary nucleotide base. Exemplary nucleotide bases and analogs thereof include, but are not limited to, naturally occurring nucleotide bases, e.g., adenine, guanine, cytosine, 6 methyl-cytosine, uracil, thymine, and analogs of the naturally occurring nucleotide bases, e.g., 7-deazaadenine, 7-deazaguanine, 7-deaza-8-azaguanine, 7-deaza-8-azaadenine, N6-Δ2-isopentenyladenine (6iA), N6-Δ2-isopentenyl-2-methylthioadenine (2ms6iA), N2-dimethylguanine (dmG), 7-methylguanine (7mG), inosine, nebularine, 2-aminopurine, 2-amino-6-chloropurine, 2,6-diaminopurine, hypoxanthine, pseudouridine, pseudocytosine, pseudoisocytosine, 5-propynylcytosine, isocytosine, isoguanine, 7-deazaguanine, 2-thiopyrimidine, 6-thioguanine, 4-thiothymine, 4-thiouracil, $O^6$-methylguanine, $N^6$-methyladenine, $O^4$-methylthymine, 5,6-dihydrothymine, 5,6-dihydrouracil, pyrazolo[3,4-D]pyrimidines (see, e.g., U.S. Pat. Nos. 6,143,877 and 6,127,121 and PCT published application WO 01/38584), ethenoadenine, indoles such as nitroindole and 4-methylindole, and pyrroles such as nitropyrrole. Certain exemplary nucleotide bases can be found, e.g., in Fasman, 1989, Practical Handbook of Biochemistry and Molecular Biology, pp. 385-394, CRC Press, Boca Raton, Fla., and the references cited therein.

The term "nucleotide", as used herein, refers to a compound comprising a nucleotide base linked to the C-1' carbon of a sugar, such as ribose, arabinose, xylose, and pyranose, and sugar analogs thereof. The term nucleotide also encompasses nucleotide analogs. The sugar may be substituted or unsubstituted. Substituted ribose sugars include, but are not limited to, those riboses in which one or more of the carbon atoms, for example the 2'-carbon atom, is substituted with one or more of the same or different Cl, F, —R, —OR, —NR$_2$ or halogen groups, where each R is independently H, $C_1$-$C_6$ alkyl or $C_5$-$C_{14}$ aryl. Exemplary riboses include, but are not limited to, 2'-(C1-C6)alkoxyribose, 2'-(C5-C14)aryloxyribose, 2',3'-didehydroribose, 2'-deoxy-3'-haloribose, 2'-deoxy-3'-fluororibose, 2'-deoxy-3'-chlororibose, 2'-deoxy-3'-aminoribose, 2'-deoxy-3'-(C1-C6)alkylribose, 2'-deoxy-3'-(C1-C6)alkoxyribose and 2'-deoxy-3'-(C5-C14) aryloxyribose, ribose, 2'-deoxyribose, 2',3'-dideoxyribose, 2'-haloribose, 2'-fluororibose, 2'-chlororibose, and 2'-alkylribose, e.g., 2'-O-methyl, 4'-α-anomeric nucleotides, 1'-α-anomeric nucleotides, 2'-4'- and 3'-4'-linked and other "locked" or "LNA", bicyclic sugar modifications (see, e.g., PCT published application nos. WO 98/22489, WO 98/39352, and WO 99/14226; and U.S. Pat. Nos. 6,268,490 and 6,794,499). Exemplary LNA sugar analogs within a polynucleotide include, but are not limited to, the structures:

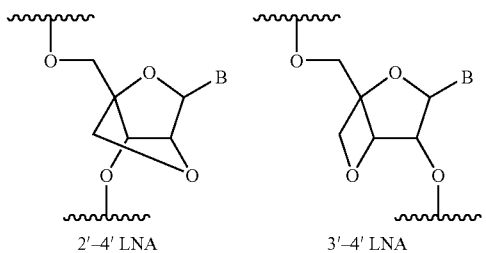

2'–4' LNA      3'–4' LNA where B is any nucleotide base.

Modifications at the 2'- or 3'-position of ribose include, but are not limited to, hydrogen, hydroxy, methoxy, ethoxy, allyloxy, isopropoxy, butoxy, isobutoxy, methoxyethyl, alkoxy, phenoxy, azido, amino, alkylamino, fluoro, chloro and bromo. Nucleotides include, but are not limited to, the natural D optical isomer, as well as the L optical isomer forms (see, e.g., Garbesi (1993) Nucl. Acids Res. 21:4159-65; Fujimori (1990) J. Amer. Chem. Soc. 112:7435; Urata, (1993) Nucleic Acids Symposium Ser. No. 29:69-70). When the nucleotide base is purine, e.g. A or G, the ribose sugar is attached to the $N^9$-position of the nucleotide base. When the nucleotide base is pyrimidine, e.g. C, T or U, the pentose sugar is attached to the $N^1$-position of the nucleotide base, except for pseudouridines, in which the pentose sugar is attached to the C5 position of the uracil nucleotide base (see, e.g., Kornberg and Baker, (1992) *DNA Replication*, 2$^{nd}$ Ed., Freeman, San Francisco, Calif.).

One or more of the pentose carbons of a nucleotide may be substituted with a phosphate ester having the formula:

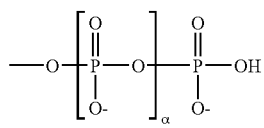

where α is an integer from 0 to 4. In certain embodiments, α is 2 and the phosphate ester is attached to the 3'- or 5'-carbon of the pentose. In certain embodiments, the nucleotides are those in which the nucleotide base is a purine, a 7-deazapurine, a pyrimidine, or an analog thereof. "Nucleotide 5'-triphosphate" refers to a nucleotide with a triphosphate ester group at the 5' position, and are sometimes denoted as "NTP", or "dNTP" and "ddNTP" to particularly point out the structural features of the ribose sugar. The triphosphate ester group may include sulfur substitutions for the various oxygens, e.g. α-thio-nucleotide 5'-triphosphates. For a review of nucleotide chemistry, see: Shabarova, Z. and Bogdanov, A. *Advanced Organic Chemistry of Nucleic Acids*, VCH, New York, 1994.

The term "nucleotide analog", as used herein, refers to embodiments in which the pentose sugar and/or the nucleotide base and/or one or more of the phosphate esters of a nucleotide may be replaced with its respective analog. In certain embodiments, exemplary pentose sugar analogs are those described above. In certain embodiments, the nucleotide analogs have a nucleotide base analog as described above. In certain embodiments, exemplary phosphate ester analogs include, but are not limited to, alkylphosphonates, methylphosphonates, phosphoramidates, phosphotriesters, phosphorothioates, phosphorodithioates, phosphoroselenoates, phosphorodiselenoates, phosphoroanilothioates, phosphoroanilidates, phosphoroamidates, boronophosphates, etc., and may include associated counterions.

Also included within the definition of "nucleotide analog" are nucleotide analog monomers which can be polymerized into polynucleotide analogs in which the DNA/RNA phosphate ester and/or sugar phosphate ester backbone is replaced with a different type of internucleotide linkage. Exemplary polynucleotide analogs include, but are not limited to, peptide nucleic acids, in which the sugar phosphate backbone of the polynucleotide is replaced by a peptide backbone.

As used herein, the terms "polynucleotide", "oligonucleotide", and "nucleic acid" are used interchangeably and mean single-stranded and double-stranded polymers of nucleotide monomers, including 2'-deoxyribonucleotides (DNA) and ribonucleotides (RNA) linked by internucleotide phosphodiester bond linkages, or internucleotide analogs, and associated counter ions, e.g., H$^+$, NH$_4^+$, trialkylammonium, Mg$^{2+}$, Na$^+$ and the like. A nucleic acid may be composed entirely of deoxyribonucleotides, entirely of ribonucleotides, or chimeric mixtures thereof. The nucleotide monomer units may comprise any of the nucleotides described herein, including, but not limited to, nucleotides and nucleotide analogs. Nucleic acids typically range in size from a few monomeric units, e.g. 5-40 when they are sometimes referred to in the art as oligonucleotides, to several thousands of monomeric nucleotide units. Unless denoted otherwise, whenever a nucleic acid sequence is represented, it will be understood that the nucleotides are in 5' to 3' order from left to right and that "A" denotes deoxyadenosine or an analog thereof, "C" denotes deoxycytidine or an analog thereof, "G" denotes deoxyguanosine or an analog thereof, and "T" denotes thymidine or an analog thereof, unless otherwise noted.

Nucleic acids include, but are not limited to, genomic DNA, cDNA, hnRNA, snRNA, mRNA, rRNA, tRNA, fragmented nucleic acid, nucleic acid obtained from subcellular organelles such as mitochondria or chloroplasts, and nucleic acid obtained from microorganisms or DNA or RNA viruses that may be present on or in a biological sample.

Nucleic acids may be composed of a single type of sugar moiety, e.g., as in the case of RNA and DNA, or mixtures of different sugar moieties, e.g., as in the case of RNA/DNA chimeras. In certain embodiments, nucleic acids are ribopolynucleotides and 2'-deoxyribopolynucleotides according to the structural formulae below:

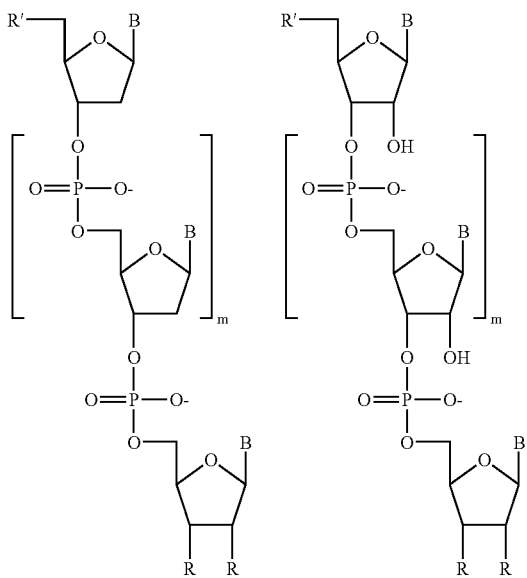

wherein each B is independently the base moiety of a nucleotide, e.g., a purine, a 7-deazapurine, a pyrimidine, or an analog thereof; each m defines the length of the respective nucleic acid and can range from zero to thousands, tens of thousands, or even more; each R is independently selected from the group comprising hydrogen, hydroxyl, halogen, —R", —OR", and —NR"R", where each R" is independently ($C_1$-$C_6$) alkyl or ($C_5$-$C_{14}$) aryl, or two adjacent Rs are taken together to form a bond such that the ribose sugar is 2',3'-didehydroribose; and each R' is independently hydroxyl or

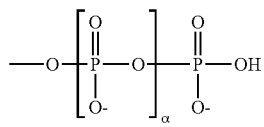

where α is zero, one or two.

In certain embodiments of the ribopolynucleotides and 2'-deoxyribopolynucleotides illustrated above, the nucleotide bases B are covalently attached to the C1' carbon of the sugar moiety as previously described.

The terms "nucleic acid", "polynucleotide", and "oligonucleotide" may also include nucleic acid analogs, polynucleotide analogs, and oligonucleotide analogs. The terms "nucleic acid analog", "polynucleotide analog" and "oligonucleotide analog" are used interchangeably, and refer to a nucleic acid that contains at least one nucleotide analog and/or at least one phosphate ester analog and/or at least one pentose sugar analog. Also included within the definition of nucleic acid analogs are nucleic acids in which the phosphate ester and/or sugar phosphate ester linkages are replaced with other types of linkages, such as N-(2-aminoethyl)-glycine amides and other amides (see, e.g., Nielsen et al., 1991, *Science* 254:1497-1500; WO 92/20702; U.S. Pat. No. 5,719,262; U.S. Pat. No. 5,698,685); morpholinos (see, e.g., U.S. Pat. No. 5,698,685; U.S. Pat. No. 5,378,841; U.S. Pat. No. 5,185,144); carbamates (see, e.g., Stirchak & Summerton, 1987, *J. Org. Chem.* 52: 4202); methylene(methylimino) (see, e.g., Vasseur et al., 1992, *J. Am. Chem. Soc.* 114: 4006); 3'-thioformacetals (see, e.g., Jones et al., 1993, *J. Org. Chem.* 58: 2983); sulfamates (see, e.g., U.S. Pat. No. 5,470,967); 2-aminoethylglycine, commonly referred to as PNA (see, e.g., Buchardt, WO 92/20702; Nielsen (1991) *Science* 254: 1497-1500); and others (see, e.g., U.S. Pat. No. 5,817,781; Frier & Altman, 1997, *Nucl. Acids Res.* 25:4429 and the references cited therein). Phosphate ester analogs include, but are not limited to, (i) $C_1$-$C_4$ alkylphosphonate, e.g. methylphosphonate; (ii) phosphoramidate; (iii) $C_1$-$C_6$ alkyl-phosphotriester; (iv) phosphorothioate; and (v) phosphorodithioate.

The terms "annealing" and "hybridization" are used interchangeably and mean the base-pairing interaction of one nucleic acid with another nucleic acid that results in formation of a duplex, triplex, or other higher-ordered structure. In certain embodiments, the primary interaction is base specific, e.g., A/T and G/C, by Watson/Crick and Hoogsteen-type hydrogen bonding. In certain embodiments, base-stacking and hydrophobic interactions may also contribute to duplex stability.

An "enzymatically active mutant or variant thereof," when used in reference to an enzyme such as a polymerase or a ligase, means a protein with appropriate enzymatic activity. Thus, for example, but without limitation, an enzymatically active mutant or variant of a DNA polymerase is a protein that is able to catalyze the stepwise addition of appropriate deoxynucleoside triphosphates into a nascent DNA strand in a template-dependent manner. An enzymatically active mutant or variant differs from the "generally-accepted" or consensus sequence for that enzyme by at least one amino acid, including, but not limited to, substitutions of one or more amino acids, addition of one or more amino acids, deletion of one or more amino acids, and alterations to the amino acids themselves. With the change, however, at least some catalytic activity is retained. In certain embodiments, the changes involve conservative amino acid substitutions. Conservative amino acid substitution may involve replacing one amino acid with another that has, e.g., similar hydrophobicity, hydrophilicity, charge, or aromaticity. In certain embodiments, conservative amino acid substitutions may be made on the basis of similar hydropathic indices. A hydropathic index takes into account the hydrophobicity and charge characteristics of an amino acid, and in certain embodiments, may be used as a guide for selecting conservative amino acid substitutions. The hydropathic index is discussed, e.g., in Kyte et al., *J. Mol. Biol.*, 157:105-131 (1982). It is understood in the art that conservative amino acid substitutions may be made on the basis of any of the aforementioned characteristics.

Alterations to the amino acids may include, but are not limited to, glycosylation, methylation, phosphorylation, biotinylation, and any covalent and noncovalent additions to a protein that do not result in a change in amino acid sequence. "Amino acid" as used herein refers to any amino acid, natural or nonnatural, that may be incorporated, either enzymatically or synthetically, into a polypeptide or protein.

Fragments, for example, but without limitation, proteolytic cleavage products, are also encompassed by this term, provided that at least some enzyme catalytic activity is retained.

The skilled artisan will readily be able to measure catalytic activity using an appropriate well-known assay. Thus, an appropriate assay for polymerase catalytic activity might include, for example, measuring the ability of a variant to incorporate, under appropriate conditions, rNTPs or dNTPs into a nascent polynucleotide strand in a template-dependent manner. Likewise, an appropriate assay for ligase catalytic activity might include, for example, the ability to ligate adjacently hybridized oligonucleotides comprising appropriate reactive groups. Protocols for such assays may be found, among other places, in Sambrook et al., Molecular Cloning, A Laboratory Manual, Cold Spring Harbor Press (1989) (hereinafter "Sambrook et al."), Sambrook and Russell, Molecular Cloning, Third Edition, Cold Spring Harbor Press (2000) (hereinafter "Sambrook and Russell"), Ausubel et al., Current Protocols in Molecular Biology (1993) including supplements through September 2005, John Wiley & Sons (hereinafter "Ausubel et al.").

A "target," "target nucleic acid," or "target nucleic acid sequence" is a nucleic acid sequence in a sample. In certain embodiments, a target nucleic acid sequence serves as a template for amplification in a PCR reaction. In certain embodiments, a target nucleic acid sequence serves as a ligation template. Target nucleic acid sequences may include both naturally occurring and synthetic molecules. Exemplary target nucleic acid sequences include, but are not limited to, genomic DNA, ligation products, and amplification products.

A "pivotal nucleotide" is a nucleotide of interest in a target nucleic acid sequence, and may represent, for example, without limitation, a single polymorphic nucleotide in a multiallelic target locus. In certain embodiments, a pivotal nucleotide is deleted in one or more alleles of a multiallelic target locus. In certain embodiments, a pivotal nucleotide is added in one or more alleles of a multiallelic target locus. In certain embodiments, a target nucleic acid sequence may comprise more than one pivotal nucleotide.

A "pivotal complement" or "pivotal complement nucleotide" is a nucleotide base complementary to a pivotal nucleotide.

A "buffering agent" is a compound added to an amplification reaction which modifies the stability, activity, and/or longevity of one or more components of the amplification reaction by regulating the pH of the amplification reaction. Certain buffering agents are well known in the art and include, but are not limited to, Tris and Tricine.

The term "sample" refers to any substance comprising nucleic acid material.

An additive is a compound added to a composition which modifies the stability, activity, and/or longevity of one or more components of the composition. In certain embodiments, the composition is an amplification reaction composition. In certain embodiments, an additive inactivates contaminant enzymes, stabilizes protein folding, and/or decreases aggregation. Exemplary additives that may be included in an amplification reaction include, but are not limited to, betaine, formamide, KCl, $CaCl_2$, MgOAc, $MgCl_2$, NaCl, $NH_4OAc$, NaI, $Na(CO_3)_2$, LiCl, MnOAc, NMP, trehalose, demiethylsulfoxide ("DMSO"), glycerol, ethylene glycol, dithiothreitol ("DTT"), pyrophosphatase (including, but not limited to Thermoplasma acidophilum inorganic pyrophosphatase ("TAP")), bovine serum albumin ("BSA"), propylene glycol, glycinamide, CHES, Percoll, aurintricarboxylic acid, Tween 20, Tween 21, Tween 40, Tween 60, Tween 85, Brij 30, NP-40, Triton X-100, CHAPS, CHAPSO, Mackernium, LDAO, Zwittergent 3-10, Xwittergent 3-14, Xwittergent SB 3-16, Empigen, NDSB-20, T4G32, *E. Coli* SSB, RecA, nicking endonucleases, 7-deazaG, dUTP, and UNG, anionic detergents, cationic detergents, non-ionic detergents, zwittergent, sterol, osmolytes, cations, and any other chemical, protein, or cofactor that may alter the efficiency of amplification. In certain embodiments, two or more additives are included in an amplification reaction.

The term "probe" comprises a polynucleotide that comprises a specific portion designed to hybridize in a sequence-specific manner with a complementary region of a specific nucleic acid sequence, e.g., a target nucleic acid sequence. In certain embodiments, the specific portion of the probe may be specific for a particular sequence, or alternatively, may be degenerate, e.g., specific for a set of sequences. In certain embodiments, the probe is labeled.

A "ligation probe set" is a group of two or more probes designed to detect at least one target. As a non-limiting example, a ligation probe set may comprise two nucleic acid probes designed to hybridize to a target such that, when the two probes are hybridized to the target adjacent to one another, they are suitable for ligation together.

The statement that two probes are "hybridized adjacent to each other" on a target nucleic acid encompasses the situation in which the 3' end of one probe and the 5' end of the other probe hybridize to contiguous regions of the target nucleic acid. The statement also encompasses the situation in which there is a gap between the probes when they are initially hybridized to the target nucleic acid, and the gap is filled by a gap-filling procedure, e.g., by extending one of the probes with a polymerase or by hybridizing an oligonucleotide to the region of the target nucleic acid that is opposite the gap. Thus, the probes become hybridized adjacent to each other on the target nucleic acid sequence through the gap-filling procedure.

"Suitable for ligation" refers to at least one first target-specific probe and at least one second target-specific probe, each comprising an appropriately reactive group. Exemplary reactive groups include, but are not limited to, a free hydroxyl group on the 3' end of the first probe and a free phosphate group on the 5' end of the second probe. Exemplary pairs of reactive groups include, but are not limited to: phosphorothioate and tosylate or iodide; esters and hydrazide; $RC(O)S^-$, haloalkyl, or $RCH_2S$ and α-haloacyl; thiophosphoryl and bromoacetoamido groups. Exemplary reactive groups include, but are not limited to, S-pivaloyloxymethyl-4-thiothymidine. Additionally, in certain embodiments, first and second target-specific probes are hybridized to the target sequence such that the 3' end of the first target-specific probe and the 5' end of the second target-specific probe are immediately adjacent to allow ligation.

The term "addressable portion" refers to an oligonucleotide sequence designed to hybridize to the complement of the addressable portion. In certain embodiments, an addressable portion may comprise a tag, such as an allele-specific tag or a locus-specific tag.

The term "signal moiety" as used herein refers to any tag, label, or identifiable moiety.

"Detectably different signal" means that detectable signals from different signal moieties are distinguishable from one another by at least one detection method.

The term "detectable signal value" refers to a value of the signal that is detected from a label. In certain embodiments, the detectable signal value is the amount or intensity of signal that is detected from a label. Thus, if there is no detectable signal value from a label, its detectable signal value is zero (0). In certain embodiments, the detectable signal value is a characteristic of the signal other than the amount or intensity of the signal, such as the spectra, wavelength, color, or lifetime of the signal.

"Detectably different signal value" means that one or more detectable signal values are distinguishable from one another by at least one detection method.

The term "labeled probe" refers to a probe that provides a detectably different signal value depending upon whether a given nucleic acid sequence is present or absent. In certain embodiments, a labeled probe provides a detectably different signal value when the intact labeled probe is hybridized to a given nucleic acid sequence than when the intact labeled probe is not hybridized to a given nucleic acid sequence. Thus, if a given nucleic acid sequence is present, the labeled probe provides a detectably different signal value than when the given nucleic acid sequence is absent. In certain embodiments, a labeled probe provides a detectably different signal value when the probe is intact than when the probe is not intact. In certain such embodiments, a labeled probe remains intact unless a given nucleic acid sequence is present. In certain such embodiments, if a given nucleic acid sequence is present, the labeled probe is cleaved, which results in a detectably different signal value than when the probe is intact.

In certain embodiments, the labeled probe is an "interaction probe." The term "interaction probe" refers to a probe that comprises at least two moieties that can interact with one another to provide a detectably different signal value depending upon whether a given nucleic acid sequence is present or absent. The signal value that is detected from the interaction probe is different depending on whether the two moieties are sufficiently close to one another or are spaced apart from one another. During certain methods described herein, the proximity of the two moieties to one another is different depending upon whether the given nucleic acid is present or absent.

In certain embodiments, the two moieties of the interaction probe are moved further apart if the given nucleic acid sequence is present. In certain embodiments, the interaction probe comprises two moieties that are linked together by a link element, and the two moieties become unlinked during the method if the given nucleic acid sequence is present. The signal value that is detected from the interaction probe that includes the two moieties linked together is different from the signal value that is detected from the interaction probe when the two moieties are not linked.

The term "threshold difference between signal values" refers to a set difference between a first detectable signal value and a second detectable signal value that results when the target nucleic acid sequence that is being sought is present in a sample, but that does not result when the target nucleic acid sequence is absent. The first detectable signal value of a labeled probe is the detectable signal value from the probe when it is not exposed to a given nucleic acid sequence. The second detectable signal value is detected during and/or after an amplification reaction using a composition that comprises the labeled probe.

The term "quantitating," when used in reference to an amplification product, refers to determining the quantity or amount of a particular sequence that is representative of a target nucleic acid sequence in the sample. For example, but without limitation, one may measure the intensity of the signal from a labeled probe. The intensity or quantity of the signal is typically related to the amount of amplification product. The amount of amplification product generated correlates with the amount of target nucleic acid sequence present prior to amplification or prior to ligation and amplification, and thus, in certain embodiments, may indicate the level of expression for a particular gene.

The term "amplification product" as used herein refers to the product of an amplification reaction. Exemplary amplification reactions include, but are not limited to, primer extension, the polymerase chain reaction, and the like. Thus, exemplary amplification products include, but are not limited to, primer extension products, PCR amplicons, and the like.

The term "primer" refers to a polynucleotide that anneals to a template nucleic acid sequence and allows synthesis of a sequence complementary to the template nucleic acid sequence. Primers include, but are not limited to, spanning primers. A "PCR primer" refers to a primer in a set of at least two primers that are capable of exponentially amplifying a target nucleic acid sequence in the polymerase chain reaction.

A "spanning primer" is a primer that anneals to separate (non-contiguous) portions of the same target nucleic acid sequence. In certain embodiments, a spanning primer anneals to both the 3' and 5' ends of the same target nucleic acid sequence. In certain embodiments, a spanning primer anneals to the 3' end and another portion of the same target nucleic acid sequence. In certain embodiments, a spanning primer anneals to the 5' end and another portion of the same target nucleic acid sequence.

A "universal primer" is capable of hybridizing to the primer-specific portion of more than one species of probe, ligation product, and/or amplification product, as appropriate. A "universal primer set" comprises a first primer and a second primer that hybridize with a plurality of species of probes, ligation products, and/or amplification products, as appropriate.

In this application, a statement that one sequence is the same as or is complementary to another sequence encompasses situations where both of the sequences are completely the same or complementary to one another, and situations where only a portion of one of the sequences is the same as, or is complementary to, a portion or the entirety of the other sequence. Here, the term "sequence" encompasses, but is not limited to, nucleic acid sequences, polynucleotides, oligonucleotides, probes, primers, primer-specific portions, target-specific portions, addressable portions, and oligonucleotide link elements.

In this application, a statement that one sequence is complementary to another sequence encompasses situations in which the two sequences have mismatches. Here, the term "sequence" encompasses, but is not limited to, nucleic acid sequences, polynucleotides, oligonucleotides, probes, primers, primer-specific portions, target-specific portions, addressable portions, and oligonucleotide link elements. Despite the mismatches, the two sequences should selectively hybridize to one another under appropriate conditions.

In this application, a statement that a first sequence is complementary to the 5' end of a second sequence encompasses the situation in which one or more 5' terminal nucleotides of the second sequence are mismatched with respect to the first sequence. In certain embodiments, up to five of the 5' terminal nucleotides of the second sequence are mismatched with respect to the first sequence. Despite the mismatches, the two sequences should selectively hybridize to one another under appropriate conditions.

In this application, a statement that a first sequence is complementary to the 3' end of a second sequence encompasses the situation in which one or more 3' terminal nucleotides of the second sequence are mismatched with respect to the first sequence. In certain embodiments, up to five of the 3' terminal nucleotides of the second sequence are mismatched with respect to the first sequence. Despite the mismatches, the two sequences should selectively hybridize to one another under appropriate conditions.

The term "selectively hybridize" means that, for particular identical sequences, a substantial portion of the particular identical sequences hybridize to a given desired sequence or sequences, and a substantial portion of the particular identical sequences do not hybridize to other undesired sequences. A "substantial portion of the particular identical sequences" in each instance refers to a portion of the total number of the particular identical sequences, and it does not refer to a portion of an individual particular identical sequence. In certain embodiments, "a substantial portion of the particular identical sequences" means at least 70% of the particular identical sequences. In certain embodiments, "a substantial portion of the particular identical sequences" means at least 80% of the particular identical sequences. In certain embodiments, "a substantial portion of the particular identical sequences" means at least 90% of the particular identical sequences. In certain embodiments, "a substantial portion of the particular identical sequences" means at least 95% of the particular identical sequences.

In certain embodiments, the number of mismatches that may be present may vary in view of the complexity of the composition. Thus, in certain embodiments, the more complex the composition, the more likely undesired sequences will hybridize. For example, in certain embodiments, with a given number of mismatches, a probe may more likely hybridize to undesired sequences in a composition with the entire genomic DNA than in a composition with fewer DNA sequences, when the same hybridization conditions are employed for both compositions. Thus, that given number of mismatches may be appropriate for the composition with fewer DNA sequences, but fewer mismatches may be more optimal for the composition with the entire genomic DNA.

In certain embodiments, sequences are complementary if they have no more than 20% mismatched nucleotides. In certain embodiments, sequences are complementary if they have no more than 15% mismatched nucleotides. In certain embodiments, sequences are complementary if they have no more than 10% mismatched nucleotides. In certain embodiments, sequences are complementary if they have no more than 5% mismatched nucleotides.

In this application, a statement that one sequence hybridizes or binds to another sequence encompasses situations where the entirety of both of the sequences hybridize or bind to one another, and situations where only a portion of one or both of the sequences hybridizes or binds to the entire other sequence or to a portion of the other sequence. Here, the term "sequence" encompasses, but is not limited to, nucleic acid sequences, polynucleotides, oligonucleotides, probes, primers, primer-specific portions, target-specific portions, addressable portions, and oligonucleotide link elements.

In certain embodiments, the term "to a measurably lesser extent" encompasses situations in which the event in question is reduced at least 10 fold. In certain embodiments, the term "to a measurably lesser extent" encompasses situations in which the event in question is reduced at least 100 fold.

In certain embodiments, a statement that a component may be, is, or has been "substantially removed" means that at least 90% of the component may be, is, or has been removed. In certain embodiments, a statement that a component may be, is, or has been "substantially removed" means that at least 95% of the component may be, is, or has been removed.

Certain Exemplary Spanning Primers and Certain Methods of Use

In certain embodiments, methods are provided for amplifying a target nucleic acid using a spanning primer. In certain embodiments, the spanning primer anneals to at least two separate (non-contiguous) portions of a target nucleic acid. In certain embodiments, the spanning primer is complementary to 1) a first region of the target nucleic acid that is at or near the 5' end of the target nucleic acid and 2) a second region of the target nucleic acid that is at or near the 3' end of the target nucleic acid. In certain such embodiments, the first region is within 100, 50, 25, 10, or 5 nucleotides of the 5' end of the target nucleic acid. In certain such embodiments, the second region is within 100, 50, 25, 10, or 5 nucleotides of the 3' end of the target nucleic acid. In certain embodiments, the spanning primer is complementary to the 5' and 3' ends of the target nucleic acid. In certain embodiments, the spanning primer comprises a 5' tail that does not hybridize to the target nucleic acid.

FIG. 1 shows exemplary embodiments of amplification using a spanning primer. In FIG. 1, a spanning primer (110) hybridizes to both the 3' and the 5' ends of a target nucleic acid sequence (120). In the presence of a polymerase (130), the spanning primer is elongated to form an amplification product (140).

Figure 2A:
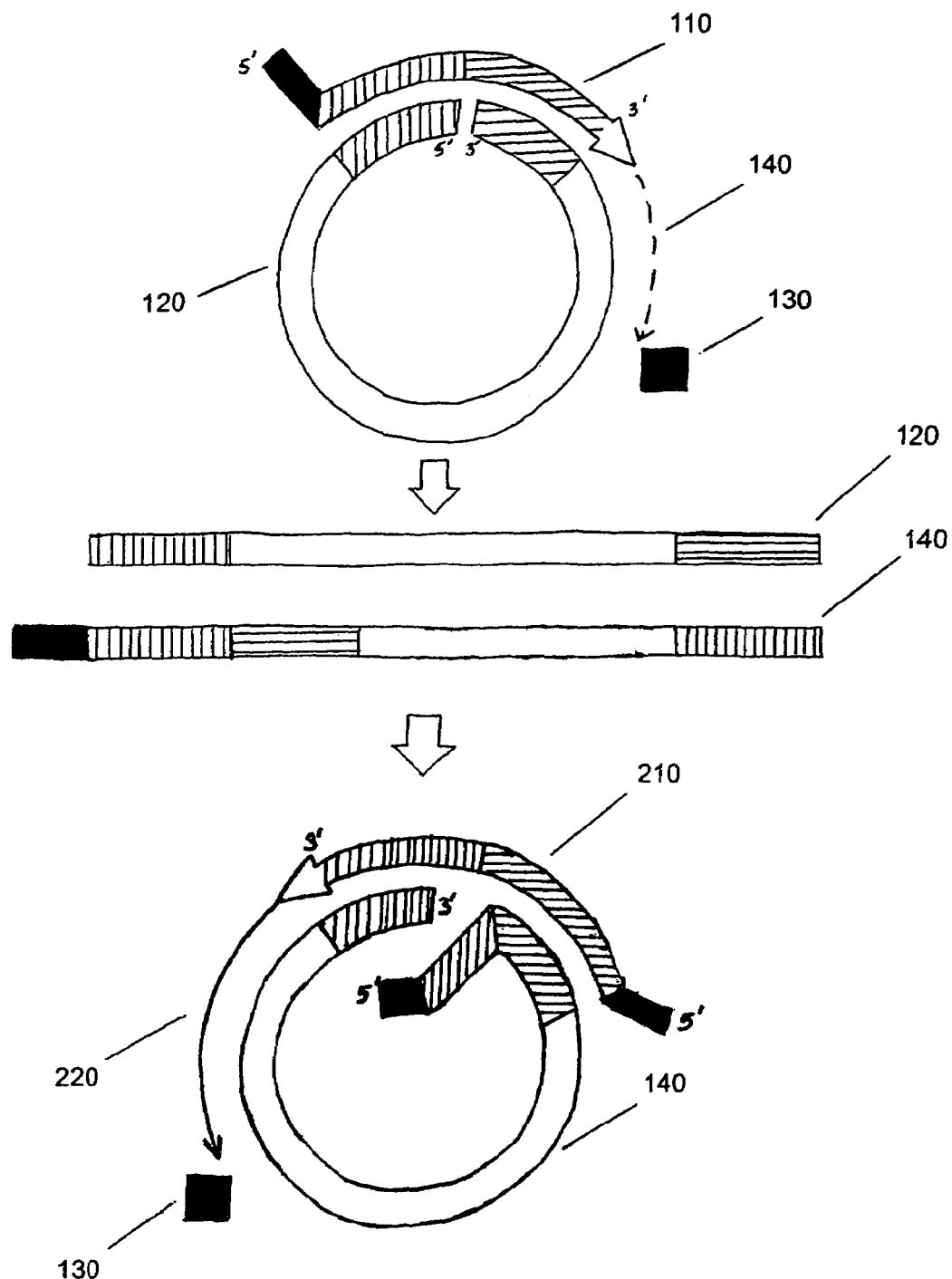
FIGS. 2A and 2B are schematic diagrams depicting methods of exponential amplification of a target nucleic acid sequence using a first spanning primer and a second spanning primer according to certain embodiments.
Figure 2B:
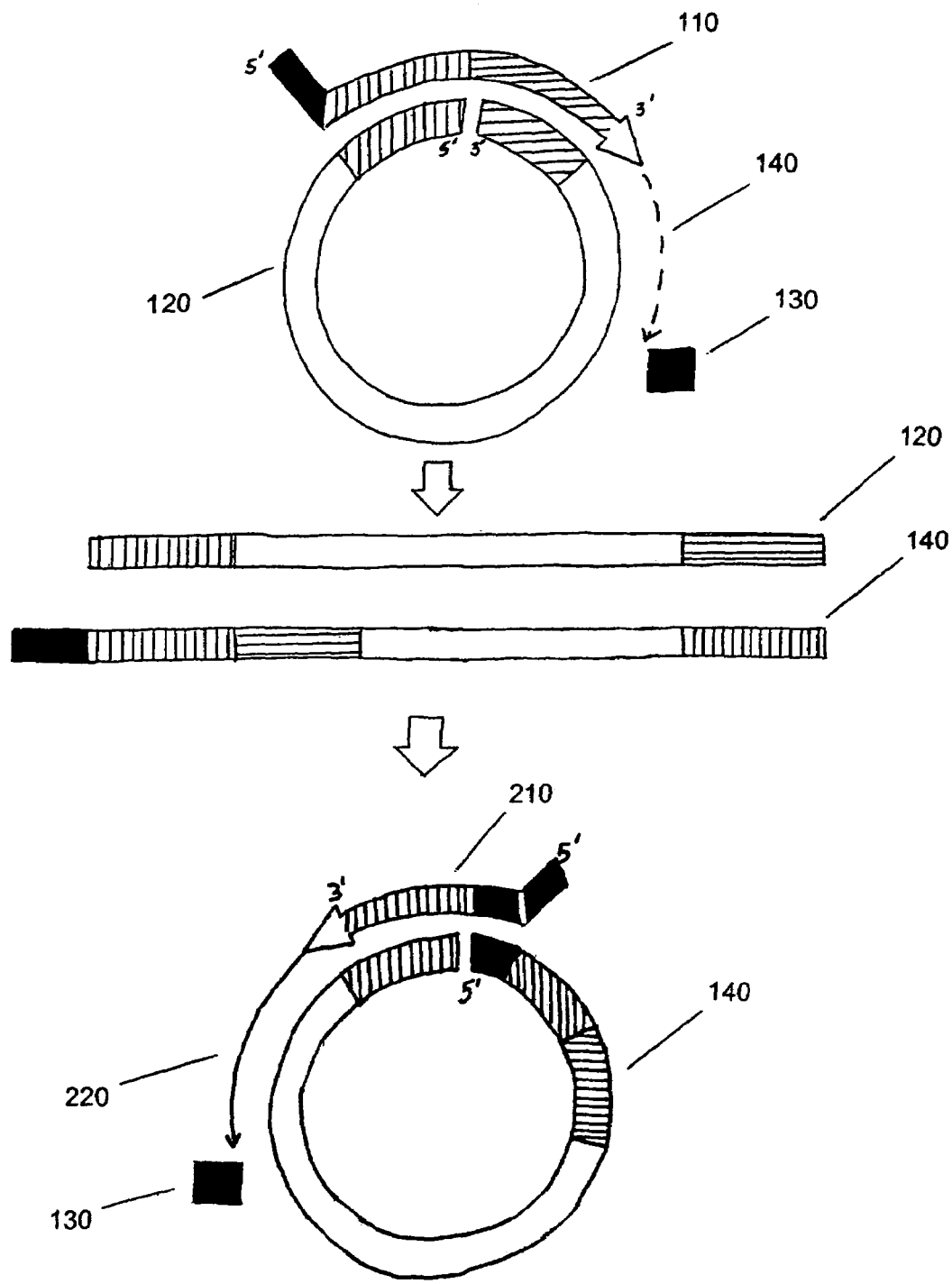

In certain embodiments, a target nucleic acid is amplified exponentially using two or more spanning primers, for example, as depicted in the embodiments shown in FIGS. 2A and 2B. In FIG. 2A, a first spanning primer (110) hybridizes to both the 3' and the 5' ends of a target nucleic acid sequence (120). In the presence of a polymerase (130), the first spanning primer is elongated to form a first amplification product (140). A second spanning primer (210) hybridizes to both the 3' end of the first amplification product (140) and to any portion of the first spanning primer incorporated into the first amplification product. The second spanning primer (210) is elongated by the polymerase (130) to form a polynucleotide comprising the target nucleic acid sequence with the addition of the second spanning primer at its 5' end (220). FIG. 2B depicts the same method as FIG. 2A, except that the second spanning primer (210) hybridizes to both the 3' end of the first amplification product (140) and to the 5' end of the first spanning primer incorporated into the first amplification product.

In certain embodiments, a spanning primer is used to amplify a ligation product. In certain such embodiments, a spanning primer amplifies a ligation product with greater efficiency than one or more non-spanning primers. For example, in certain embodiments, a first nucleic acid and a second nucleic acid are combined in a ligation mixture under conditions permissive for ligation of the first nucleic acid to the second nucleic acid. In certain instances, ligation may be incomplete, such that the ligation mixture comprises unligated nucleic acids as well as ligation products. In certain embodiments, the ligation products may be amplified from the ligation mixture using, e.g., a non-spanning primer that anneals to either the first or the second nucleic acid in the ligation product. Under certain conditions, however, the non-spanning primer is capable of annealing to the unligated first or second nucleic acid in the ligation mixture and is extended. This decreases the efficiency of the amplification of the ligation products and generates spurious amplification products.

Figure 3A:
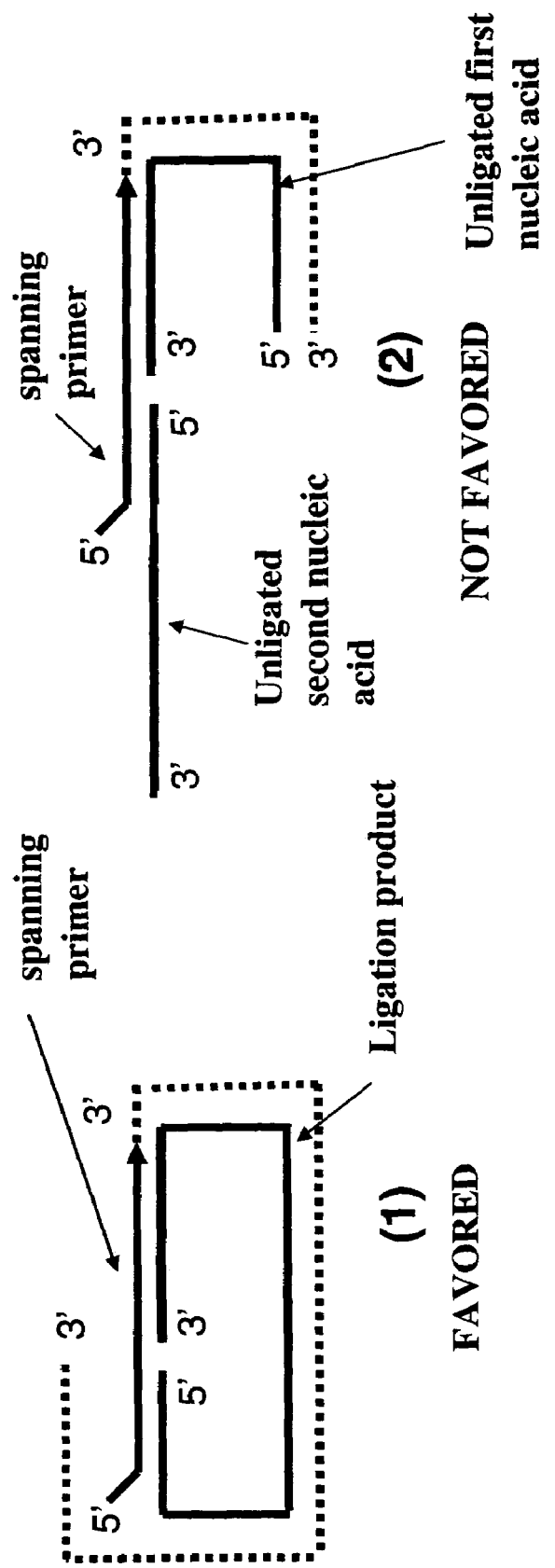
FIGS. 3A and 3B show an exemplary use of spanning primers to favor amplification of ligation products over amplification of unligated nucleic acids, according to certain embodiments.
Figure 3B:
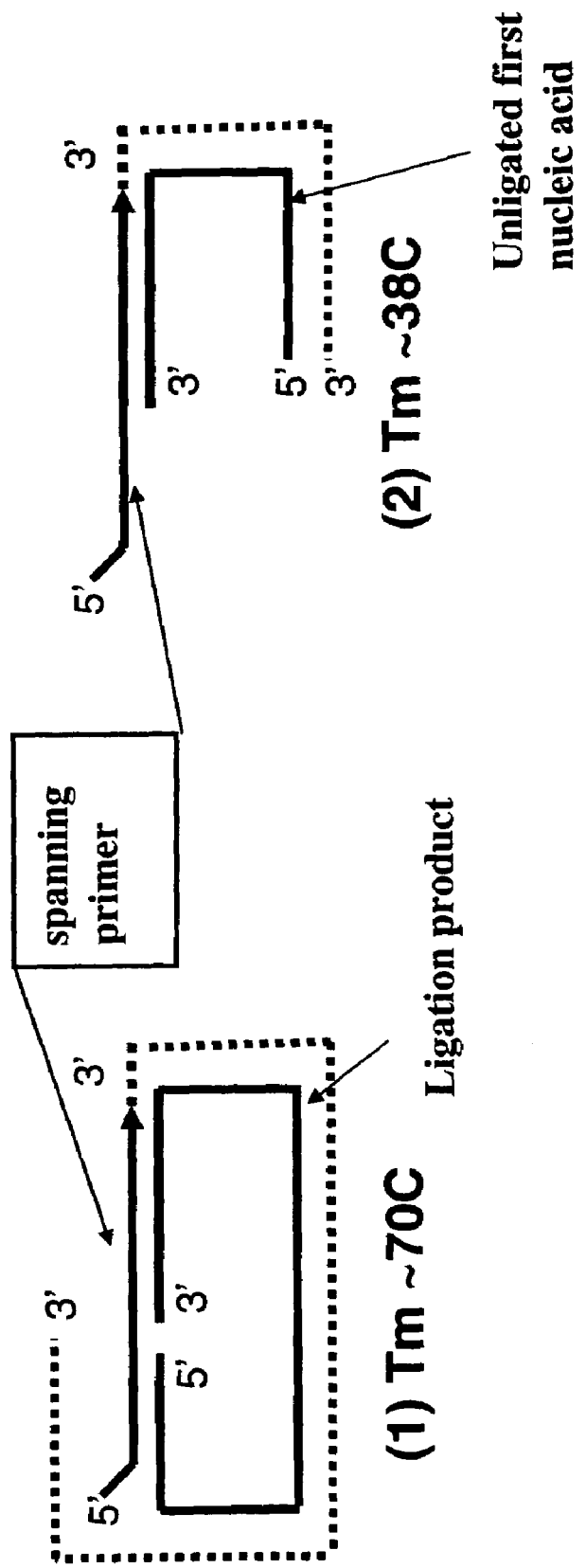

In certain embodiments, a spanning primer favors amplification of ligation products over amplification of unligated nucleic acids in a ligation mixture. FIGS. 3A and 3B illustrates certain such embodiments. For example, in the embodiments shown in FIGS. 3A and 3B, a spanning primer anneals to a first region that is at the 5' end of a ligation product and a second region that is at the 3' end of the ligation product. In certain such embodiments, the spanning primer may comprise non-annealing nucleotides disposed between the nucleotides that anneal to the first region and second region of the ligation product. In certain such embodiments, the number of non-annealing nucleotides may be any number of nucleotides between 0 and 10 nucleotides.

In certain embodiments, a spanning primer is capable of annealing to unligated nucleic acids. In certain embodiments, under certain conditions, however, the spanning primer does not anneal as efficiently to unligated nucleic acids as it does to the ligation product. Thus, amplification of the ligation product by the spanning primer is favored.

In certain embodiments, a spanning primer does not anneal to both an unligated first nucleic acid and an unligated second nucleic acid as efficiently as it does to a ligation product comprising the first and second nucleic acids. For example, FIG. 3A shows certain embodiments in which the spanning primer is capable of annealing to the unligated first and second nucleic acids in a "three-molecule" interaction (2). This three-molecule interaction, however, is not as favored kinetically or thermodynamically as the annealing of the spanning primer to the ligation product, a "two-molecule" interaction (1).

In certain embodiments, under certain annealing conditions, a spanning primer does not anneal to either the unligated first nucleic acid or the unligated second nucleic acid as efficiently as it does to the ligation product. For example, in certain embodiments, the Tm of the hybridization complex between the spanning primer and the ligation product is higher than the Tm of the hybridization complex between the spanning primer and either the first or the second unligated nucleic acid. For example, as illustrated in FIG. 3B, the region of complementarity between the spanning primer and the ligation product is greater than the region of complementarity between the spanning primer and the unligated first nucleic acid. Thus, the Tm of the hybridization complex between the spanning primer and the ligation product is higher than the Tm of the hybridization complex between the spanning primer and the unligated first nucleic acid. One skilled in the art would readily understand that, for the same reasons, the Tm of the hybridization complex between the spanning primer and the ligation product is higher than the Tm of the hybridization complex between the spanning primer and the unligated second nucleic acid. In view of this difference in Tms, one skilled in the art could ascertain an annealing temperature that favors the formation of the hybridization complex including the ligation product over the hybridization complex including the unligated first or second nucleic acids.

For example, in certain embodiments, amplification may be performed using an annealing temperature that is greater than the Tm of the hybridization complex between the spanning primer and at least one of the unligated nucleic acids. For example, the annealing temperature may be at least 5° C., at least 10° C., at least 20° C., or at least 30° C. greater than the Tm of the hybridization complex between the spanning primer and an unligated nucleic acid. In certain such embodiments, the annealing temperature is less than or equal to the Tm of the hybridization complex between the spanning primer and the ligation product. For example, the annealing temperature may be any temperature from 0° C. to at least 10° C. less than the Tm of the hybridization complex between the spanning primer and the ligation product. Under certain such exemplary conditions, the formation of a hybridization complex between the spanning primer and the ligation product is favored over the formation of a hybridization complex between the spanning primer and an unligated nucleic acid.

In certain embodiments, ligation products are amplified directly from all or a portion of a ligation mixture using a spanning primer. For example, in certain embodiments, the ligation products are not isolated or purified from the ligation mixture prior to the amplification. In certain embodiments, the ligation mixture is not diluted prior to the amplification.

In certain embodiments, spanning primers are used to amplify ligation products produced in an oligonucleotide ligation assay (OLA). Certain exemplary methods for performing OLA and amplifying ligation products are described, e.g., in U.S. patent application Ser. No. 09/584,905, filed May 30, 2000; U.S. patent application Ser. No. 10/011,993, filed Dec. 5, 2001, corresponding to U.S. Patent Application Publication No. US 2003/0119004 A1; Patent Cooperation Treaty Application No. PCT/US01/17329, filed May 30, 2001, corresponding to PCT International Publication No. WO 01/92579 A2, published Dec. 6, 2001, and U.S. Patent Application Publication No. US 2003/0190646 A1; Patent Cooperation Treaty Application No. PCT/US97/45559, filed May 27, 1997; and U.S. Pat. No. 6,027,889, issued Feb. 22, 2000.

Figure 4:
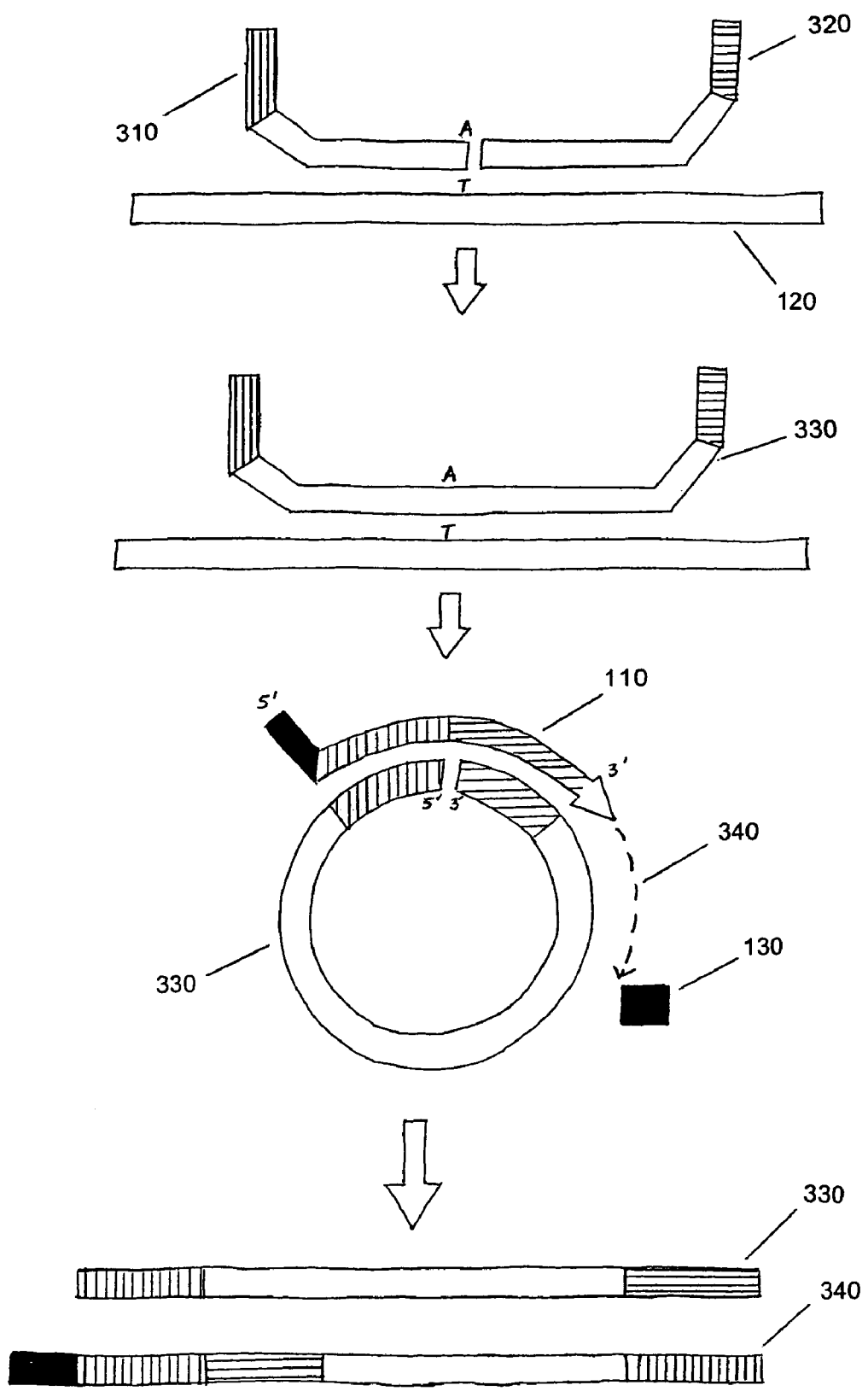
FIG. 4 is a schematic diagram depicting a method of ligation and amplification using a spanning primer according to certain embodiments. A first probe (310) and a second probe (320) are hybridized to a target nucleic acid sequence (120) adjacent to one another, such that the first probe and the second probe are suitable for ligation together. After at least one cycle of ligation, a ligation product (330) is formed, comprising the first probe (310) and the second probe (320). A spanning primer (110) hybridizes to both the 3' and the 5' ends of the ligation product (330). In the presence of a polymerase (130), the spanning primer (110) is elongated to form a first amplification product (340).

FIG. 4 shows exemplary embodiments in which a ligation product resulting from an OLA is amplified using a spanning primer. In the embodiments shown in FIG. 4, a first probe (310) and a second probe (320) are hybridized to a target nucleic acid sequence (120) adjacent to each other, such that the adjacent ends of the first and second probes are ligated together under suitable conditions.

In certain embodiments, there is a gap between the first probe and the second probe upon hybridization of those probes to the target nucleic acid sequence. In certain such embodiments, the gap is filled by a gap-filling procedure. For example, in certain embodiments, the gap is filled by an oligonucleotide that is complementary to the target nucleic acid sequence opposite the gap. In certain embodiments, the gap is filled by extension of the 3' end of either the first or second probe. Thus, in certain embodiments, the first and second probes become hybridized adjacent to one another on the target nucleic acid sequence through the gap-filling procedure. In certain embodiments, a gap-filling procedure increases the specificity of the OLA.

In the embodiments shown in FIG. 4, a ligation product (330) is formed after at least one cycle of ligation, wherein the ligation product comprises the first probe (310) and the second probe (320). A spanning primer (110) hybridizes to both the 3' and the 5' ends of the ligation product (330). In the presence of a polymerase (130), the spanning primer (110) is elongated to form a first amplification product (340).

In certain embodiments, an OLA may be used for genotyping a nucleic acid. For example, in certain embodiments, an OLA may be used to determine the allele present at a polymorphic locus, such as a locus comprising a "SNP," or "single nucleotide polymorphism." In an exemplary OLA, illustrated in FIG. 5, a sample comprising a target nucleic acid that comprises a SNP is combined with a ligation probe set. The ligation probe set comprises one or more allele-specific oligonucleotides (ASOs) (also referred to as "allele specific probes") and a locus-specific oligonucleotide (LSO) (also referred to as a "locus-specific probe"). The ASO and the LSO each comprise a target-specific portion (T-SP) that hybridizes to the target nucleic acid. The target-specific portion of the ASO comprises a nucleotide called a "pivotal complement" (PC). That nucleotide is complementary to one of the possible nucleotides (X), or "pivotal nucleotides," at the polymorphic nucleotide. When more than one ASO is used, the ASOs may comprise different pivotal complements to distinguish different alleles. In certain embodiments, the pivotal complement is located at the 5' terminal nucleotide of an ASO. In certain embodiments, the pivotal complement is located at the 3' terminal nucleotide of an ASO. The ASO and the LSO hybridize adjacent to each other on the target nucleic acid, such that the 5' end of one of the oligonucleotides is adjacent to the 3' end of the other. Under conditions permissive for ligation, an ASO comprising a pivotal complement that is complementary to the pivotal nucleotide becomes ligated to an adjacently hybridized LSO, whereas an ASO comprising a pivotal nucleotide that is not complementary to the pivotal nucleotide does not substantially ligate to an adjacently hybridized LSO. In various embodiments, ligation products are detected using methods comprising amplifying the ligation product and detecting the amplification product.

In certain embodiments, a ligation product comprising an ASO and a LSO is amplified using a first spanning primer that anneals to a region that is at the 5' end of the ligation product and a region that is at the 3' end of the ligation product. For example, in certain embodiments, the first spanning primer comprises a first portion and a second portion, wherein the first portion is 3' of the second portion. In certain such embodiments, such as the embodiments shown in FIG. 6A, the first portion anneals to the 3' end of the LSO and the second portion anneals to the 5' end of the ASO in the ligation product. In certain such embodiments, the 3' end of the LSO is blocked, e.g., by an amine group or by a minor groove binder-nonfluorescent quencher (MGB-NFQ). In certain such embodiments, the LSO or a ligation product comprising the LSO is incapable of priming nucleic acid synthesis using the first spanning primer as a template.

Alternatively, in certain embodiments, the first portion of the first spanning primer anneals to the 3' end of the ASO and the second portion anneals to the 5' end of the LSO in the ligation product. In certain such embodiments, the 3' end of the ASO is blocked, e.g., by an amine group. In certain such embodiments, the ASO or a ligation product comprising the ASO is incapable of priming nucleic acid synthesis using the first spanning primer as a template.

In certain embodiments, the first portion of the first spanning primer is about 5, 6, 7, 8, 9, or 10 nucleotides in length. In certain embodiments, the second portion of the first spanning primer is about 9, 10, 11, or 12 nucleotides in length. In certain embodiments, the Tm of the hybridization complex between the first spanning primer and the ligation product is any temperature from about 60° C. to 75° C., including all temperatures within that range.

Figure 5:
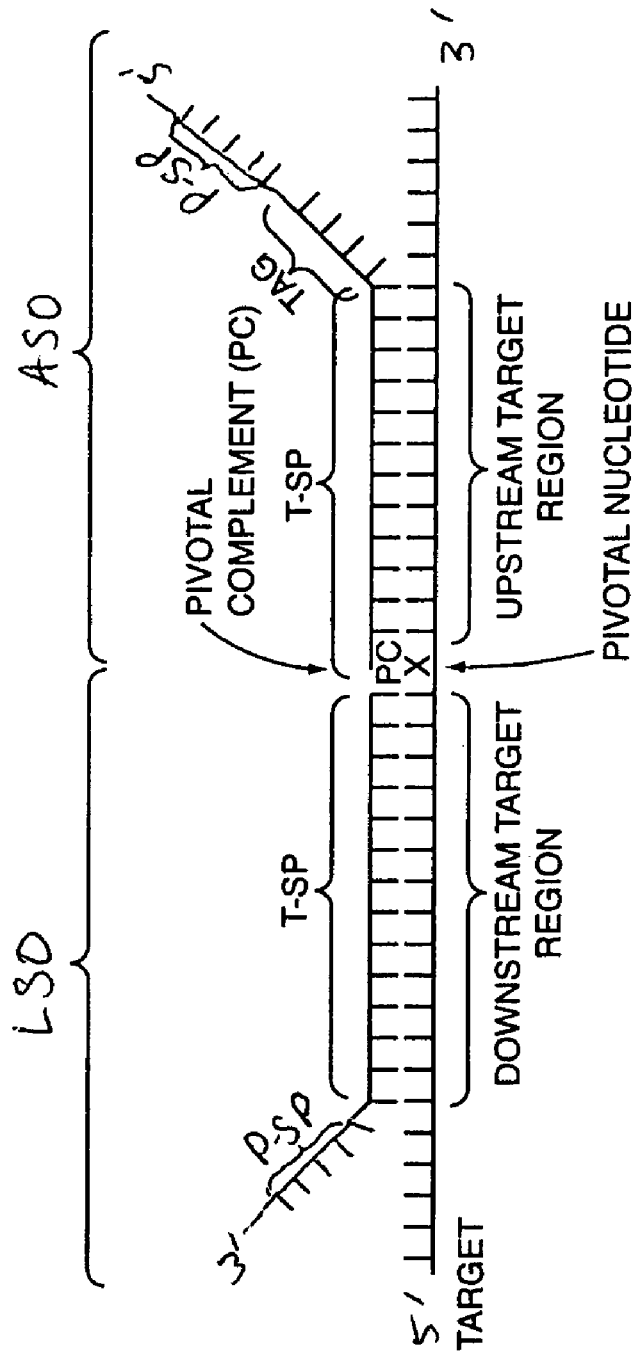
FIG. 5 shows exemplary components of an exemplary oligonucleotide ligation assay (OLA), according to certain embodiments.

In certain embodiments, such as the embodiment shown in FIG. 5, an ASO and/or a LSO comprises a primer-specific portion (P-SP) that does not hybridize to the target nucleic acid. In certain embodiments, an ASO comprises an addressable portion, such as a tag, that does not hybridize to the target nucleic acid. In certain such embodiments, such as the embodiment shown in FIG. 5, the tag ("TAG") is disposed between the primer-specific portion (P-SP) and the target-specific portion (T-SP) of the ASO. In certain embodiments in which more than one ASO is used, ASOs having different pivotal complements comprise different tag sequences, and ASOs having the same pivotal complement comprise the same tag sequence. In certain such embodiments, the tag sequences provide a mechanism for distinguishing ligation products or amplification products in an allele-specific manner.

In certain embodiments, an LSO comprises an addressable portion, such as a tag, that does not hybridize to the target nucleic acid. In certain such embodiments, the tag is disposed between the primer-specific portion and the target-specific portion of the LSO. In certain embodiments, the tag sequence provides a mechanism for identifying the locus from which a ligation product or amplification product is derived. In certain embodiments, the tag sequence provides a mechanism for separating ligation or amplification products using methods such as hybridization based pullout (HBP). See, e.g., WO 01/92579.

Figure 6A:
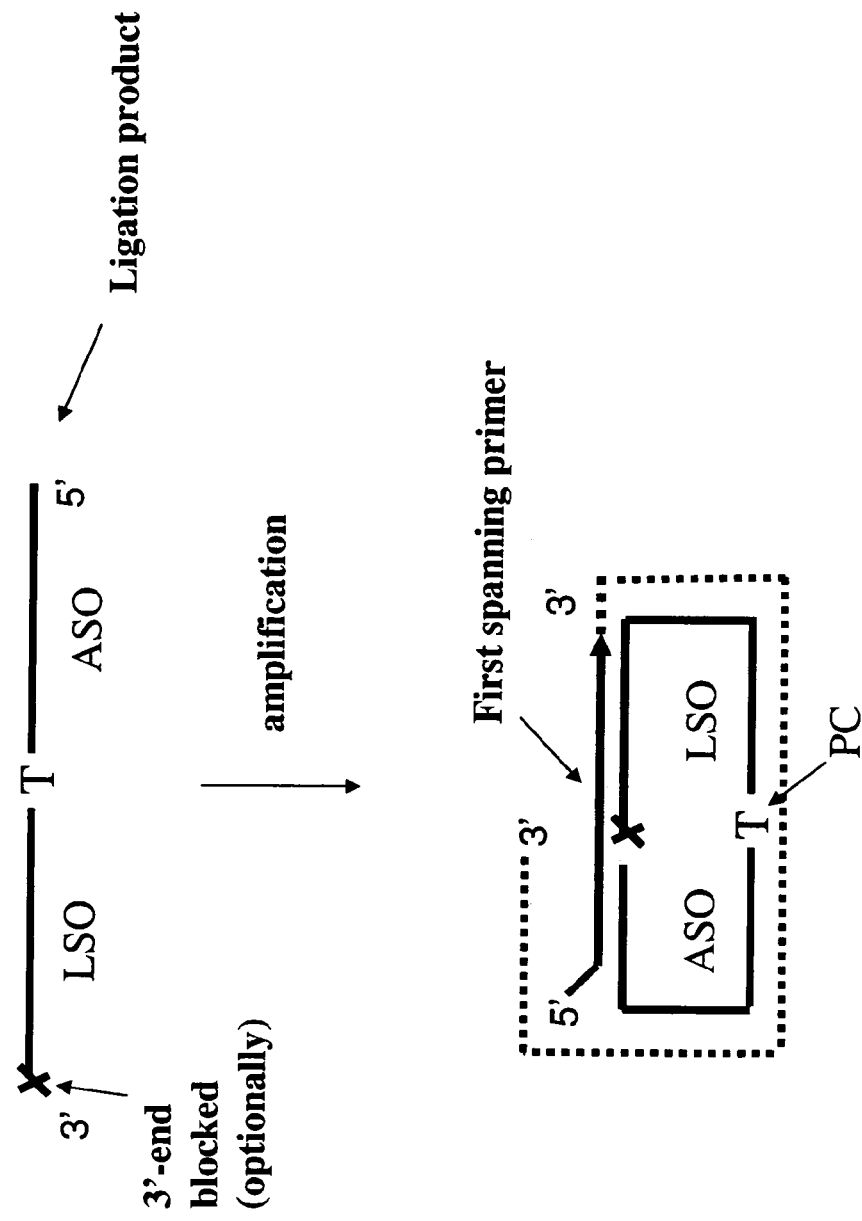
FIGS. 6A and 6B show certain exemplary embodiments of amplification of a ligation product using a spanning primer.
Figure 6B:
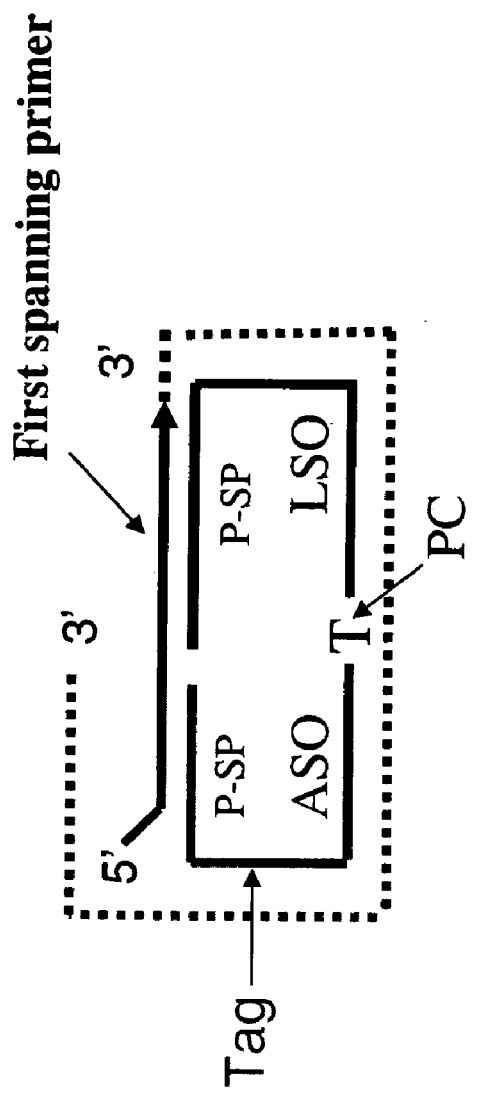

In certain embodiments, illustrated in FIG. 6B, a ligation product comprising an ASO and a LSO is amplified using a first spanning primer comprising a first portion (red) that anneals to the primer-specific portion of the LSO and a second portion (dark blue) that anneals to the primer-specific portion of the ASO. In certain embodiments, the sequences of the primer-specific portions of the ASO and LSO for a particular target nucleic acid (e.g., a first locus) are the same as the sequences of the primer-specific portions of an ASO and LSO for a different target nucleic acid (e.g., a second locus). In certain such embodiments, a first spanning primer may serve as a universal primer for the amplification of ligation products corresponding to two different target nucleic acids (e.g., two different genomic loci), thus allowing "multiplex" amplification to take place.

In certain embodiments, such as the embodiments shown in FIGS. 6A and 6B, a first spanning primer comprises a 5' "tail" (light blue) that does not anneal to the ligation product. In certain such embodiments, the 5' tail or its complement comprises a sequence that may serve as a binding site for a universal primer.

Figure 7:
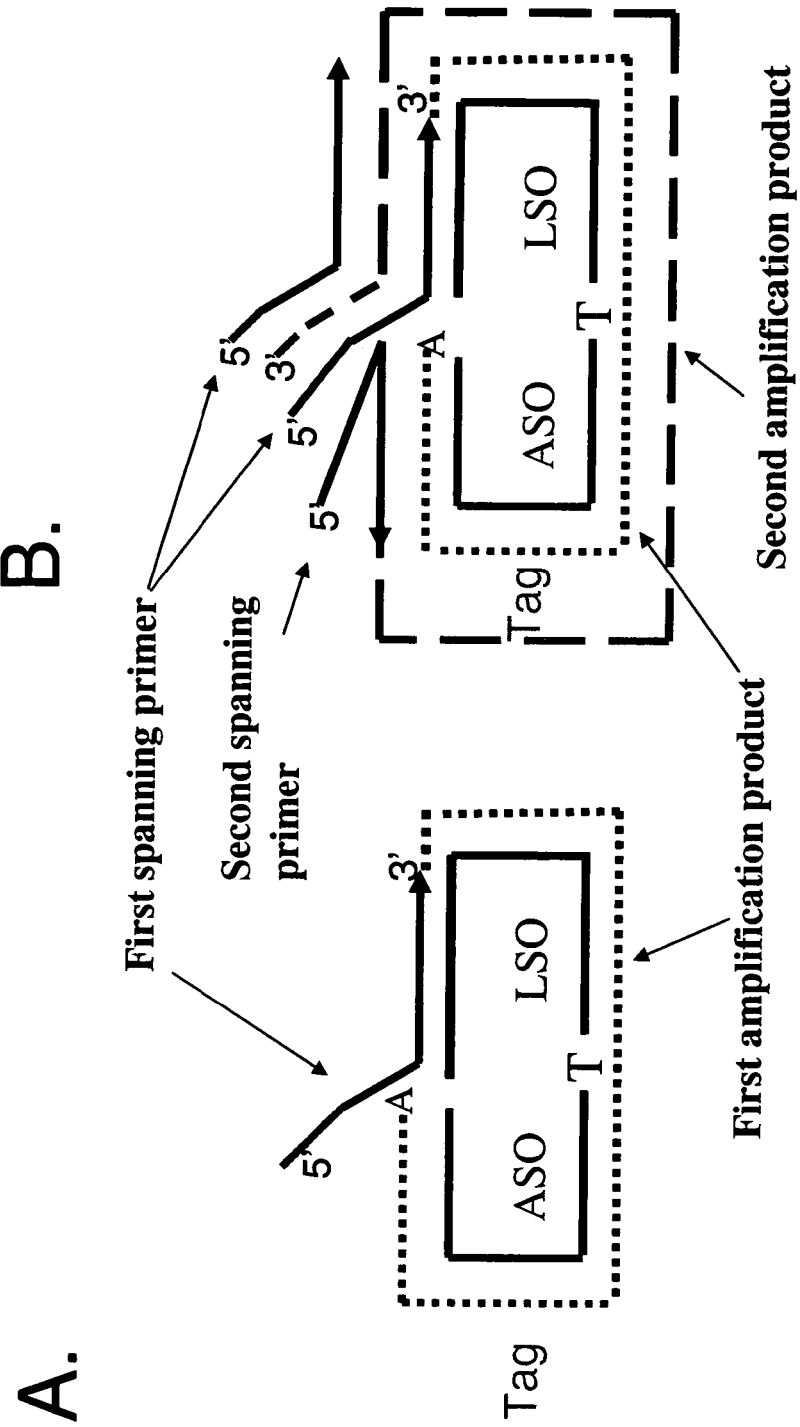
FIGS. 7A and 7B show certain exemplary embodiments of amplifying a ligation product using first and second spanning primers.

In certain embodiments of amplification, a first spanning primer is extended using a polymerase that lacks 5' to 3' exonuclease activity. In certain such embodiments, the polymerase possesses strand displacement activity, as illustrated in FIGS. 7A and 8A. In certain such embodiments, the amplification product comprises the complement of the ligation product plus additional sequence at the 5' end of the amplification product. That additional sequence corresponds to the 5' end of the first spanning primer. In certain embodiments, a polymerase that lacks 5' to 3' exonuclease activity is the Stoffel fragment of Taq DNA polymerase. In certain such embodiments, the Stoffel fragment adds an adenine (A) to the 3' end of the amplification product in a non-template-directed manner. See, e.g., FIGS. 7A and 8A.

In certain embodiments of amplification, a first spanning primer is extended using a polymerase that possesses 5' to 3' exonuclease activity. In certain such embodiments, the polymerase will extend the first spanning primer using the ligation product as a template. When the extending polymerase reaches the portion of the ligation product that is annealed to the second portion of the first spanning primer, the polymerase will degrade the region of the first spanning primer that is annealed to the ligation product.

In certain embodiments, the amplification product resulting from extension of the first spanning primer (the first amplification product) is further amplified using a second primer. In certain such embodiments, as illustrated in FIG. 7B, the second primer comprises a portion that anneals to a region at the 3' end of the first amplification product. In certain embodiments, such as the embodiments shown in FIG. 8B, the second primer is a second spanning primer comprising a first portion and a second portion, wherein the first portion is 3' of the second portion. In certain such embodiments, the first portion anneals to a region at the 3' end of the first amplification product, and the second portion anneals to a region at the 5' end of the first amplification product. In certain embodiments, such as the embodiments shown in FIG. 8B, the region at the 5' end of the first amplification product comprises the 5' tail of the first spanning primer.

In certain embodiments, the first portion of the second spanning primer is about 10, 11, 12, 13, 14, or 15 nucleotides in length. In certain embodiments, the second portion of the second spanning primer is about 9, 10, 11, 12, 13, or 14 nucleotides in length. In certain embodiments, the Tm of the hybridization complex between the second spanning primer and the first amplification product is any temperature from about 60° C. to 78° C., including all temperatures within that range.

In certain embodiments, such as the embodiments shown in FIGS. 7B and 8B, the second primer comprises a 5' tail (black) that does not anneal to the first amplification product. In certain such embodiments, the 5' tail or its complement comprises a sequence that may serve as a binding site for a universal primer.

In certain embodiments, such as those shown in FIGS. 7B and 8B, the second primer is extended to form a second amplification product, i.e, an amplification product that comprises a sequence complementary to the first amplification product that resulted from extension of the first spanning primer. In various embodiments, any of the polymerases discussed above may be used to extend the second primer. In certain embodiments, such as the embodiments shown in FIGS. 7B and 8B, the first spanning primer anneals to the second amplification product and is extended. In this manner, in certain embodiments, multiple amplification cycles may be carried out using the first spanning primer and second primer in the same reaction mixture.

Certain Exemplary Cycling Conditions in Amplification Reactions Using Spanning Primers In certain embodiments, the annealing temperature for amplification may be from about 55° C. to 75° C., including all temperatures within that range. In certain such embodiments, the annealing temperature for amplification may be from about 65° C. to about 75° C. In certain such embodiments, the annealing temperature is higher than that typically used in certain PCRs (~55° C.). In certain embodiments, a higher annealing temperature may minimize non-specific priming as well as priming by unligated ASOs and/or LSOs. In certain embodiments, a higher annealing temperature may also minimize other PCR artifacts such as primer dimers.

In certain embodiments in which multiple amplification cycles are performed, different amplification cycles may have different annealing temperatures. For example, in certain embodiments, the first 1, 2, 3, 4, or 5 cycles may have a lower annealing temperature than subsequent cycles. For example, in certain embodiments, the first 1, 2, 3, 4, or 5 cycles may be performed using a first annealing temperature of about 65 to about 70° C., including all temperatures within that range. In certain such embodiments, subsequent cycles may be performed using a second annealing temperature that is higher than the first annealing temperature, e.g., at 70° C.-75° C., including all temperatures within that range.

In certain embodiments, the annealing step of an amplification cycle is from about 10-30 seconds in length, including all times between those endpoints. In certain embodiments, annealing and extension may be performed in a single step. In certain embodiments, a total of about 20 to about 40 cycles are performed, including any number of cycles between those endpoints.

Certain Exemplary Methods of Genotyping Using Spanning Primers

As discussed above, in certain embodiments, OLA can be used to determine the allele or alleles present at a polymorphic locus, such as a locus comprising a SNP. FIGS. 9-13 show certain exemplary embodiments for detecting the particular allele or alleles present at a biallelic locus. In those figures, nucleic acid sequences having the same color are the same or are complementary to one another. One skilled in the art would understand that various embodiments may be adapted for the detection of up to four alleles at any given SNP.

Figure 9A:
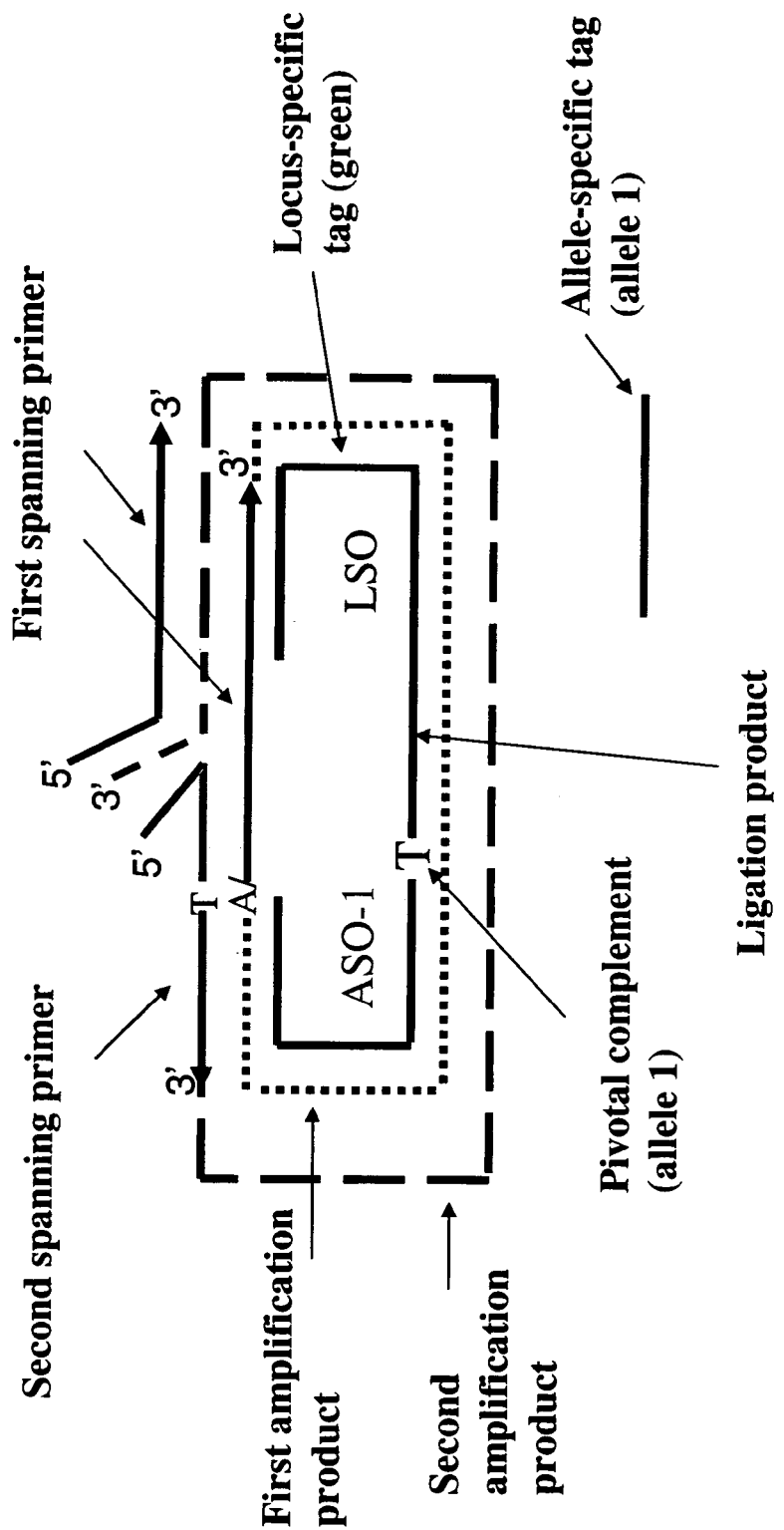
FIGS. 9A and 9B show certain exemplary methods of genotyping using first and second spanning primers.

FIG. 9A shows amplification of a ligation product resulting from oligonucleotide ligation at a biallelic locus, according to certain embodiments. In FIG. 9A, the ligation product comprises an ASO (ASO-1) and a LSO. ASO-1 comprises a pivotal complement (a "T") that is complementary to the pivotal nucleotide for one of the alleles ("allele 1") at the biallelic locus. ASO-1 also comprises a primer-specific portion (dark blue). The LSO comprises a primer-specific portion (red). If allele 1 is present at the biallelic locus, a ligation product comprising ASO-1 and LSO is formed, as shown in FIG. 9A.

In FIG. 9A, a first spanning primer specific for allele 1 is used to amplify the ligation product. The first spanning primer comprises a first portion (red) that anneals to the primer-specific portion of the LSO and a second portion that anneals to the primer-specific portion of ASO-1 (dark blue) in the ligation product. The first spanning primer further comprises a 5' tail (light blue). Together, the 5' tail (light blue) and the second portion (dark blue) of the first spanning primer comprise an allele-specific tag (specific for allele 1), which will be incorporated into a first amplification product. The term "allele-specific tag" refers to a nucleic acid sequence or its complement which indicates whether a particular allele is present in a target nucleic acid.

The first amplification product resulting from extension of the first spanning primer is amplified using a second spanning primer specific for allele 1. Specifically, the second spanning primer comprises a first portion (dark blue) that anneals to the complement of the primer-specific portion of ASO-1 and a second portion (light blue) that anneals to the 5' tail of the first spanning primer in the first amplification product. In certain embodiments, the second spanning primer further comprises a 5' tail (orange). The second amplification product resulting from extension of the second spanning primer comprises the complement of the allele-specific tag. The second amplification product may then be amplified by the first spanning primer. Multiple amplification cycles may then be carried out using the first and second spanning primers.

In certain embodiments, if allele 1 is not present at the biallelic locus, then the pivotal complement of ASO-1 will not base pair with the pivotal nucleotide at the biallelic locus. In certain such embodiments, no ligation product will form, and thus, there will be no ligation product for the first spanning primer to amplify. Thus, in certain such embodiments, the absence of amplification products from the first and/or second spanning primers indicates the absence of allele 1 at the biallelic locus. Conversely, in certain embodiments, if allele 1 is present at the biallelic locus, then the pivotal complement of ASO-1 will base pair with the pivotal nucleotide at the biallelic locus. In certain such embodiments, ligation products will form, and the first spanning primer will amplify those ligation products. Thus, in certain such embodiments, the presence of amplification products from the first and/or second spanning primers indicates the presence of allele 1 at the biallelic locus.

In certain embodiments, ligation products comprising ASO-1 and LSO may form even if allele 1 is not present at the biallelic locus. In certain such embodiments, those "non-specific" ligation products may be amplified by the first spanning primer. However, such non-specific ligation occurs to a measurably lesser extent than "allele-specific" ligation, which occurs when allele 1 is present at the biallelic locus. In certain embodiments, one can quantify non-specific ligation by subjecting ASO-1 and LSO to conditions permissive for ligation in the presence of a target nucleic acid comprising the biallelic locus in which allele 1 is not present (e.g., a negative control). In certain embodiments, one can quantify allele-specific ligation by subjecting ASO-1 and LSO to conditions permissive for ligation in the presence of a target nucleic acid comprising the biallelic locus in which allele 1 is present (e.g., a positive control). In certain embodiments, one can quantify ligation, e.g., by detecting amplification products from the first and/or second spanning primers. The quantitative difference between non-specific and allele-specific ligation can be used to set an appropriate threshold value, above which it is considered that allele 1 is present at the biallelic locus.

Figure 9B:
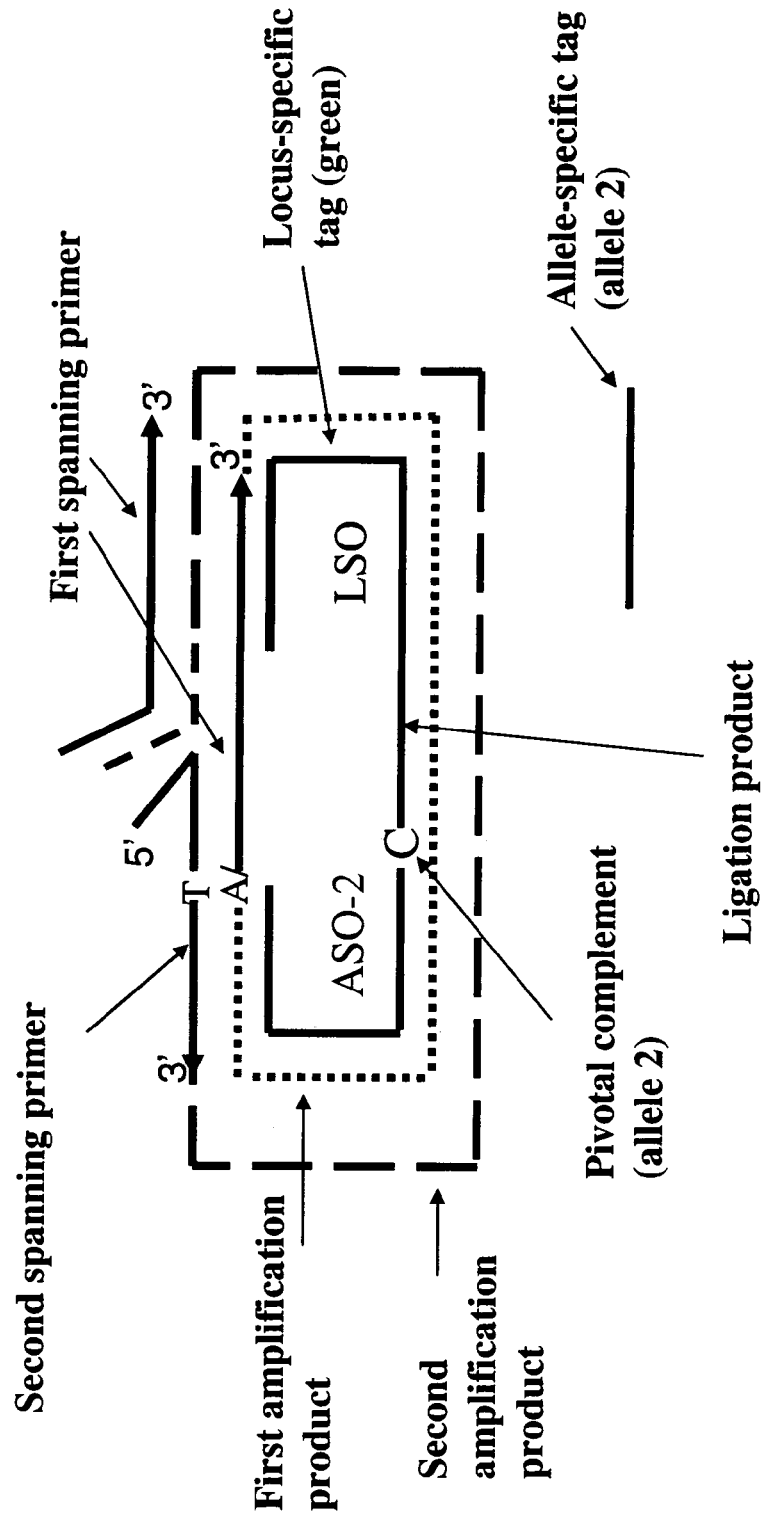

FIG. 9B shows amplification of a ligation product resulting from oligonucleotide ligation at the same biallelic locus shown in FIG. 9A, according to certain embodiments. In FIG. 9B, the ligation product comprises an ASO (ASO-2) and a LSO. ASO-2 comprises a pivotal complement (a "C") that is complementary to the pivotal nucleotide for the second allele ("allele 2") at the biallelic locus. ASO-2 also comprises a primer-specific portion (brown). The LSO comprises a primer-specific portion (red). If allele 2 is present at the biallelic locus, a ligation product comprising ASO-2 and LSO is formed, as shown in FIG. 9B.

In FIG. 9B, a first spanning primer specific for allele 2 is used to amplify the ligation product. The first spanning primer comprises a first portion (red) that anneals to the primer-specific portion of the LSO and a second portion (brown) that anneals to the primer-specific portion of ASO-2 in the ligation product. The first spanning primer further comprises a 5' tail (pink). Together, the 5' tail (pink) and the second portion (brown) of the first spanning primer comprise an allele-specific tag (specific for allele 2), which will be incorporated into a first amplification product.

In FIG. 9B, the first amplification product resulting from extension of the first spanning primer is amplified using a second spanning primer specific for allele 2. Specifically, the second spanning primer comprises a first portion (brown) that anneals to the primer-specific portion of ASO-2 and a second portion (pink) that anneals to the 5' tail of the first spanning primer in the amplification product. In certain embodiments, the second spanning primer further comprises a 5' tail (orange). The second amplification product resulting from extension of the second spanning primer comprises the complement of the allele-specific tag. The second amplification product may then be amplified by the first spanning primer. Multiple amplification cycles may then be carried out using the first and second spanning primers.

In certain embodiments, if allele 2 is not present at the biallelic locus, then the pivotal complement of ASO-2 will not base pair with the pivotal nucleotide at the biallelic locus. In certain such embodiments, no ligation product will form, and thus, there will be no ligation product for the first spanning primer to amplify. Thus, in certain such embodiments, the absence of amplification products from the first and/or second spanning primers indicates the absence of allele 2 at the biallelic locus. Conversely, in certain embodiments, if allele 2 is present at the biallelic locus, then the pivotal complement of ASO-2 will base pair with the pivotal nucleotide at the biallelic locus. In certain such embodiments, ligation products will form, and the first spanning primer will amplify those ligation products. Thus, in certain such embodiments, the presence of amplification products from the first and/or second spanning primers indicates the presence of allele 2 at the biallelic locus.

In certain embodiments, ligation products comprising ASO-2 and LSO may form even if allele 2 is not present at the biallelic locus. In certain such embodiments, those "non-specific" ligation products may be amplified by the first spanning primer. However, such non-specific ligation occurs to a measurably lesser extent than "allele-specific" ligation, which occurs when allele 2 is present at the biallelic locus. In certain embodiments, one can quantify non-specific ligation by subjecting ASO-2 and LSO to conditions permissive for ligation in the presence of a target nucleic acid comprising the biallelic locus in which allele 2 is not present (e.g., a negative control). In certain embodiments, one can quantify allele-specific ligation by subjecting ASO-2 and LSO to conditions permissive for ligation in the presence of a target nucleic acid comprising the biallelic locus in which allele 2 is present (e.g., a positive control). In certain embodiments, one can quantify ligation, e.g., by detecting amplification products from the first and/or second spanning primers. The quantitative difference between non-specific and allele-specific ligation can be used to set an appropriate threshold value, above which it is considered that allele 2 is present at the biallelic locus.

In certain embodiments, the allele(s) present at a polymorphic locus are identified by detecting allele-specific tag(s) present in amplification products specific for that locus. For example, in certain embodiments, the amplification products of FIG. 9A and the amplification products of FIG. 9B are detected and distinguished from each other by detecting their respective allele-specific tags. In certain such embodiments, the amplification reactions shown in FIGS. 9A and 9B may be performed in a single reaction mixture. Thus, in certain embodiments, if only the allele-specific tag specific for allele 1 is detected in the amplification mixture, then the biallelic locus is homozygous for allele 1. In certain embodiments, if only the allele-specific tag specific for allele 2 is detected in the amplification mixture, then the biallelic locus is homozygous for allele 2. In certain embodiments, if both the allele-specific tag specific for allele 1 and the allele-specific tag specific for allele 2 are detected in the amplification mixture, then the biallelic locus is heterozygous for allele 1 and allele 2.

In various embodiments, an allele-specific tag may be detected using a first spanning primer or a second spanning primer that comprises an allele-specific label. For example, in certain embodiments, the second spanning primer in FIG. 9A may be labeled with a particular label, and the second spanning primer in FIG. 9B may be labeled with a different label. Thus, in certain embodiments, detection of a signal from a given label indicates the presence of a particular allele-specific tag, which in turn indicates the allele present at the biallelic locus. In certain such embodiments, the detectable signal value is greater than an appropriate threshold value.

In various embodiments, an allele-specific tag may be detected using a nucleic acid probe that hybridizes to the allele-specific tag. In certain embodiments, the probe comprises a label. In certain embodiments, the probe comprises a mobility modifier. In certain such embodiments, the probe is detected using a mobility-dependent analysis technique. In certain embodiments, different allele-specific tags are detected using probes comprising different labels. In certain embodiments, different allele-specific tags are detected using probes comprising different mobility modifiers.

In certain embodiments, a LSO comprises a tag that does not hybridize to the target nucleic acid. In certain such embodiments, the tag is a locus-specific tag. The term "locus-specific tag" refers to a nucleic acid sequence or its complement which indicates whether a particular target nucleic acid is present. In certain embodiments, a locus-specific tag is disposed between the primer-specific portion and the target-specific portion of the LSO. In certain such embodiments, the locus-specific tag is used to identify the target nucleic acid, e.g., the polymorphic locus, to which the LSO is capable of hybridizing. Thus, in certain embodiments, detection of the locus-specific tag in an amplification mixture indicates the presence of an amplification product corresponding to that target nucleic acid.

In certain embodiments, locus-specific tags may be used to distinguish amplification products derived from different target nucleic acids (e.g., different loci) in a multiplex amplification reaction. For example, LSOs that hybridize to different polymorphic loci may comprise different locus-specific tags. The different locus-specific tags identify the loci to which the different LSOs hybridizes. Amplification products comprising those locus-specific tags may thus be distinguished from one another.

In certain embodiments, an amplification product comprises both a locus-specific tag (e.g., to identify the locus from which the amplification product is derived) and an allele-specific tag (e.g., to identify the particular allele that is present at the locus). Certain exemplary embodiments are shown in FIGS. 9A and 9B. The amplification products shown in FIG. 9A comprise a different allele-specific tag and the same locus-specific tag as the amplification products shown in FIG. 9B. In certain embodiments, an allele-specific tag and a locus-specific tag in a given amplification product are within about 5, 6, 7, 8, 9, or 10 nucleotides of one another. In certain such embodiments, the allele-specific tag and the locus-specific tag are within about 6-8 nucleotides of one another.

In various embodiments, the allele-specific tag and/or the locus-specific tag in an amplification product is detected. In certain embodiments, the allele-specific tag and/or the locus-specific tag in an amplification product is detected based on the mobility of the amplification product. In certain embodiments, the allele-specific tag and/or the locus-specific tag in an amplification product is detected using an allele-specific probe that hybridizes to the allele-specific tag and/or a locus-specific probe that hybridizes to the locus-specific tag. In certain embodiments, one can identify the allele present in a target nucleic acid by detecting the particular allele-specific probe that hybridizes to an amplification product specific for that target nucleic acid. In certain embodiments, one can identify the target nucleic acid from which an amplification product is obtained by detecting the particular locus-specific probe that hybridizes to the amplification product. In certain embodiments, because it is possible to distinguish amplification products in an allele-specific and a locus-specific manner, one can thus ascertain the alleles present in multiple target nucleic acids in a single multiplex reaction mixture.

For example, in certain embodiments, different probes may be used to distinguish different alleles at a particular locus. Referring to the exemplary embodiments in FIGS. 9A and 9B, in certain embodiments, a first allele-specific probe may hybridize to the "allele 1" allele-specific tag, while a second allele-specific probe may hybridize to the "allele 2" allele-specific tag. In certain embodiments, allele-specific probes that recognize different allele-specific tags comprise different labels. In certain embodiments, allele-specific probes that recognize different allele-specific tags comprise different mobility modifiers. In certain embodiments, allele-specific probes that recognize different allele-specific tags comprise the same mobility modifier but different labels.

In certain embodiments, the allele-specific tag and the locus-specific tag in an amplification product may be detected using a single nucleic acid probe that hybridizes to both the allele-specific tag and the locus-specific tag. For example, referring to the exemplary embodiments in FIGS. 9A and 9B, a first probe may hybridize to both the "allele 1" allele-specific tag and the locus-specific tag in the first or second amplification product shown in FIG. 9A, while a second probe may hybridize to both the "allele 2" allele-specific tag and the locus-specific tag in the first or second amplification product shown in FIG. 9B. In certain embodiments, the first probe and the second probe comprise different labels. In certain embodiments, the first probe and the second probe comprise the same label but different mobility modifiers. In certain embodiments, the first probe and the second probe comprise the same mobility modifier but different labels.

In certain embodiments, the allele-specific tag and the locus-specific tag in an amplification product are detected using a probe specific for the locus-specific tag and a separate probe specific for the allele-specific tag. For example, in certain embodiments, an amplification product is exposed to a locus-specific probe comprising the complement of the locus-specific tag under hybridization conditions. In certain such embodiments, the locus-specific probe is immobilized on a solid support, such as an array or a bead. In certain embodiments, by detecting whether the amplification product hybridizes to a particular locus-specific probe, one can identify the particular target nucleic acid from which the amplification product is obtained.

In certain embodiments, the amplification product is also exposed to one or more allele-specific probes, each allele-specific probe being capable of hybridizing to a different allele-specific tag. In certain such embodiments, by detecting which allele-specific probes hybridize to the amplification product, one can identify the particular alleles present in a target nucleic acid.

Figure 10:
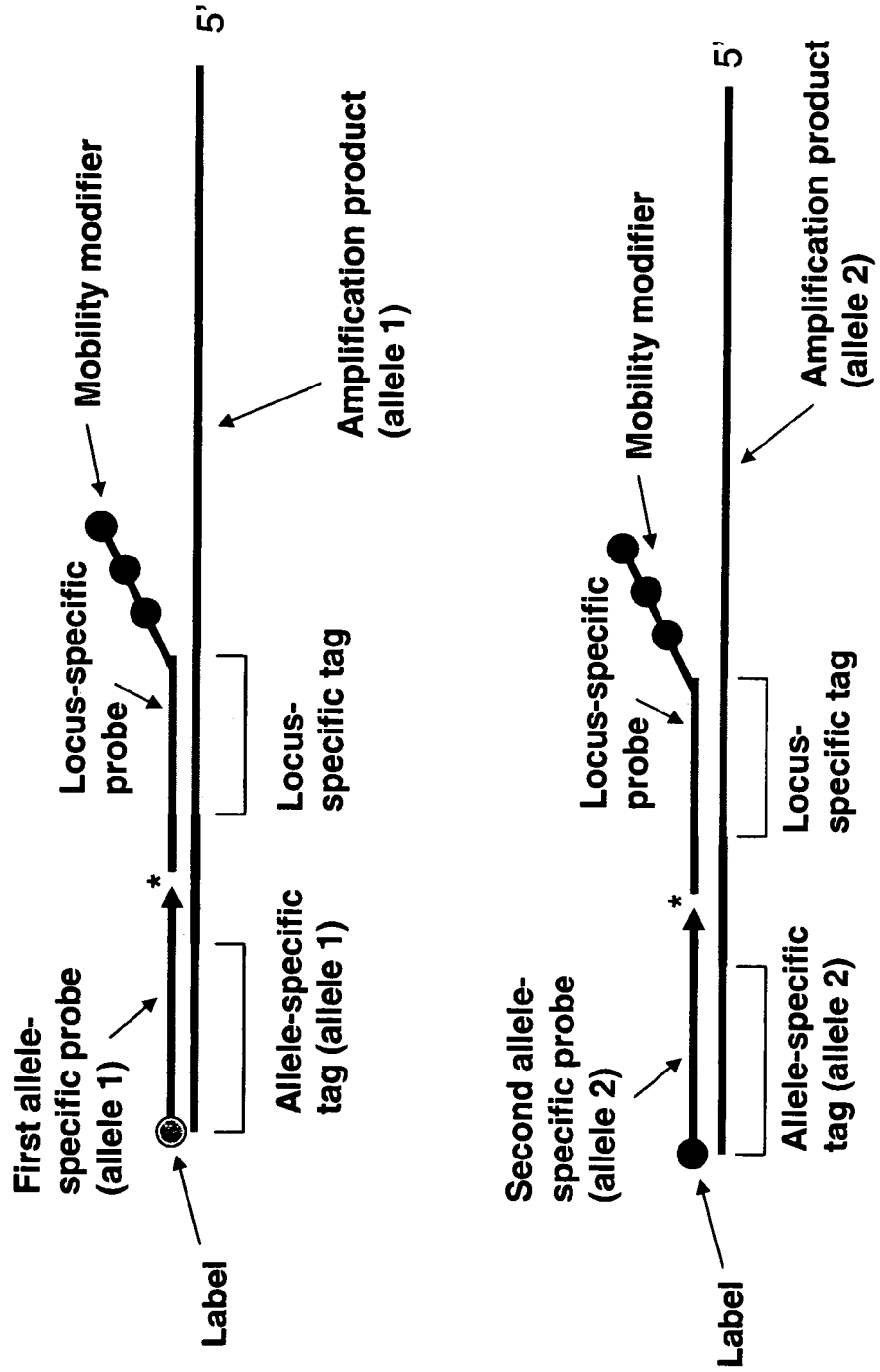
FIG. 10 shows certain exemplary embodiments in which allele-specific probes are used to distinguish between an amplification product specific for a first allele ("allele 1") of a target nucleic acid and an amplification product specific for a second allele ("allele 2") of the target nucleic acid.

FIG. 10 shows certain exemplary embodiments in which allele-specific probes are used to distinguish between an amplification product specific for a first allele ("allele 1") of a target nucleic acid and an amplification product specific for a second allele ("allele 2") of the target nucleic acid. The amplification products comprise the same locus-specific tag but different allele-specific tags. The amplification products are exposed to three different probes: 1) a first allele-specific probe that hybridizes to an "allele 1" allele-specific tag; 2) a second allele-specific probe that hybridizes to an "allele 2" allele-specific tag; and 3) a common locus-specific probe that hybridizes to the locus-specific tag in both amplification products. In the embodiments shown in FIG. 10, the first and second allele-specific probes comprise different labels. In the embodiments shown in FIG. 10, the common locus-specific probe comprises a mobility modifier.

In the embodiments shown in FIG. 10, the first allele-specific probe and the common locus-specific probe hybridize adjacent to each other on the amplification product specific for allele 1. The second allele-specific probe and the common locus-specific probe hybridize adjacent to each other on the amplification product specific for allele 2. The resulting hybridization complexes are exposed to ligation conditions. Under such conditions, the first allele-specific probe and common locus-specific probe are ligated to each other (indicated by an asterisk), and the second allele-specific probe and common locus-specific probe are ligated to each other (indicated by an asterisk). In certain embodiments, the resulting ligation products are subjected to a mobility-dependent analysis technique, such that the ligation products have substantially the same mobility but they have different labels, depending on whether they comprise the first allele-specific probe or the second allele-specific probe.

Figure 11:
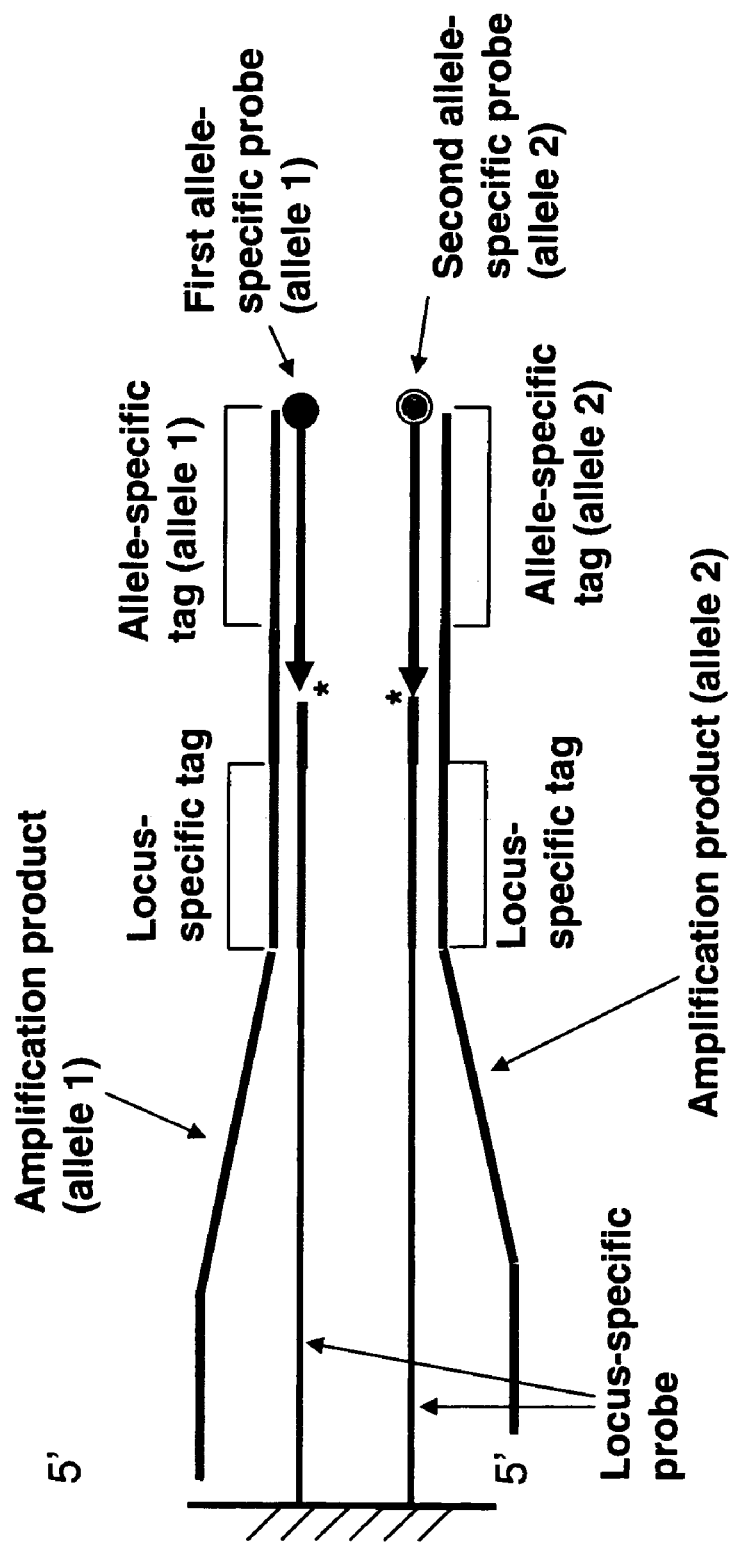
FIG. 11 shows certain exemplary embodiments in which allele-specific probes are used to distinguish between an amplification product specific for a first allele ("allele 1") of a target nucleic acid and an amplification product specific for a second allele ("allele 2") of the target nucleic acid.

FIG. 11 shows certain exemplary embodiments in which allele-specific probes are used to distinguish between an amplification product specific for a first allele ("allele 1") of a target nucleic acid and an amplification product specific for a second allele ("allele 2") of the target nucleic acid. The amplification products comprise the same locus-specific tag but different allele-specific tags. In the embodiments shown in FIG. 11, the amplification products are exposed to a common locus-specific probe under hybridization conditions. Multiple copies of the locus-specific probe may be immobilized on a solid support, e.g., on a bead or at a particular position on an array. The amplification products are also exposed to 1) a first allele-specific probe that hybridizes to an "allele 1" allele-specific tag, and 2) a second allele-specific probe that hybridizes to an "allele 2" allele-specific tag. In the embodiments shown in FIG. 11, the first allele-specific probe and the second allele-specific probe comprise different labels.

In the embodiments shown in FIG. 11, the first allele-specific probe and the locus-specific probe hybridize adjacent to each other on the amplification product specific for allele 1. Likewise, the second allele-specific probe and the locus-specific probe hybridize adjacent to each other on the amplification product specific for allele 2. Under ligation conditions, the first allele-specific probe and the locus-specific probe are ligated to each other (indicated by an asterisk), and the second allele-specific probe and the locus-specific probe are ligated to each other (indicated by an asterisk). Thus, in certain embodiments, the first and second allele-specific probes become attached to the solid support through the locus-specific probe. The labels that are detected on the solid support indicate which alleles are present in the target nucleic acid.

In certain embodiments, the allele-specific tag and the locus-specific tag in an amplification product are detected using a probe specific for the locus-specific tag and a primer specific for the allele-specific tag. For example, in certain embodiments, an amplification product is exposed to one or more allele-specific primers, wherein each primer hybridizes to a different allele-specific tag. In certain such embodiments, the allele-specific primer that hybridizes to the amplification product is extended to form an allele-specific extension product. In certain embodiments, detection of the allele-specific extension product indicates the presence of a particular allele in a target nucleic acid.

In certain embodiments, an allele-specific extension product comprises a locus-specific tag. In certain embodiments, a region of the allele-specific extension product comprising the locus-specific tag is allowed to hybridize to a locus-specific probe that comprises the complement of the locus-specific tag. In certain such embodiments, the locus-specific probe is immobilized on a solid support, such as an array or a bead. In certain embodiments, by detecting a hybridization complex between the allele-specific extension product and the locus-specific probe, one can identify the particular target nucleic acid from which the extension product is obtained.

Figure 12:
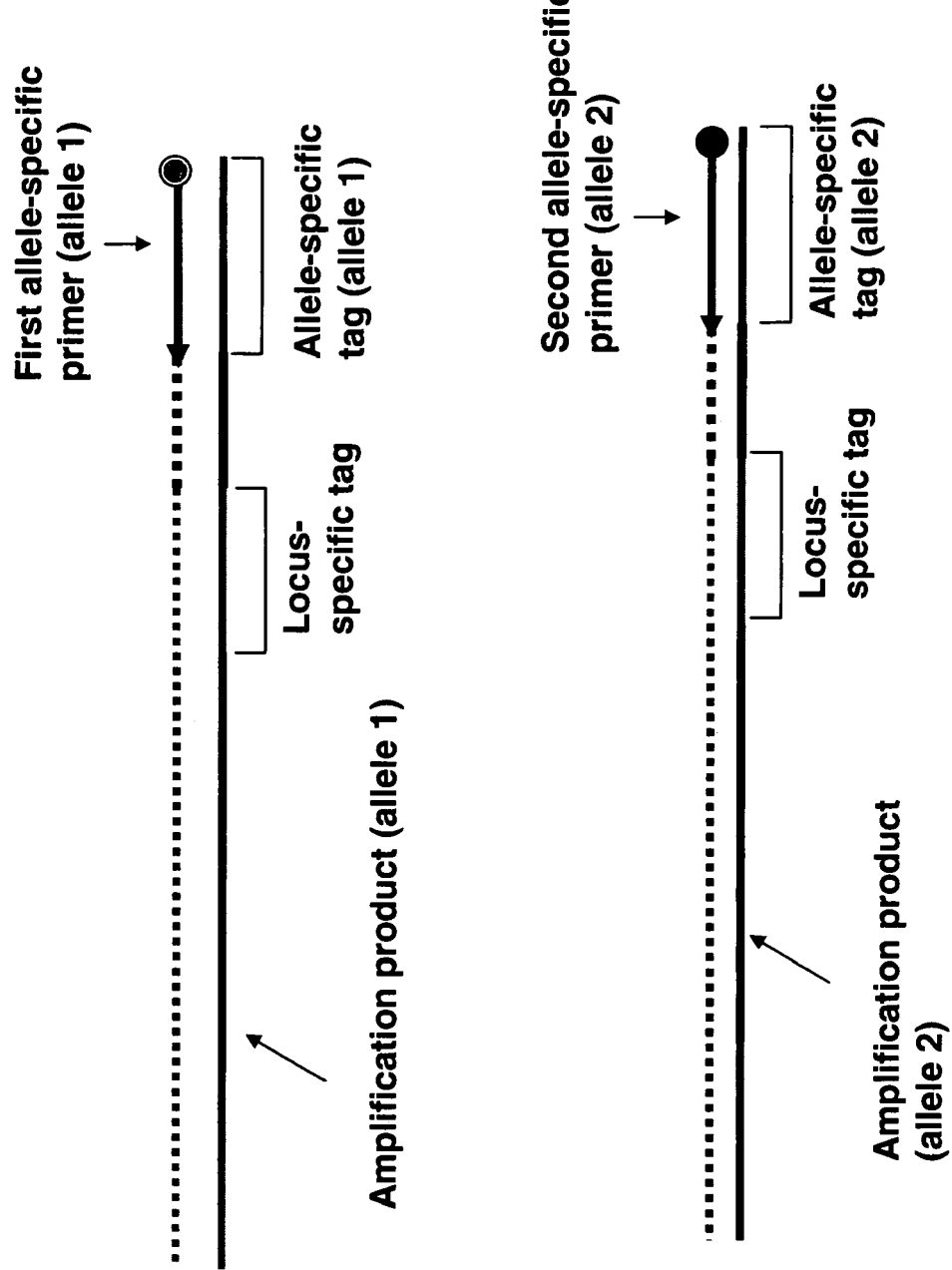
FIGS. 12A, 12B, and 12C shows certain exemplary embodiments in which allele-specific primers are used to distinguish between an amplification product specific for a first allele ("allele 1") of a target nucleic acid and an amplification product specific for a second allele ("allele 2") of the target nucleic acid.
Figure 12:
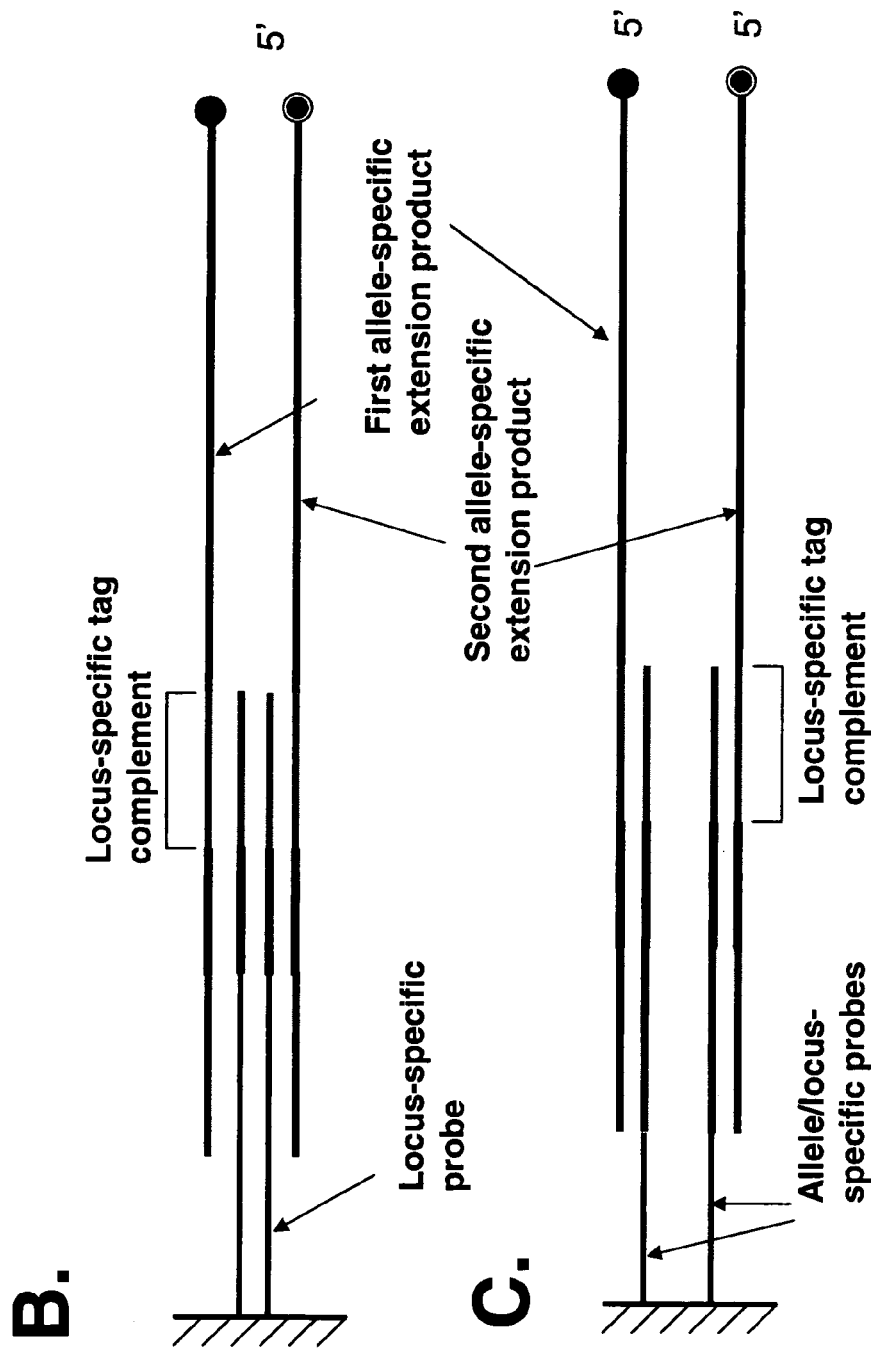

FIG. 12 shows certain exemplary embodiments in which allele-specific primers are used to distinguish between an amplification product specific for a first allele ("allele 1") of a target nucleic acid and an amplification product specific for a second allele ("allele 2") of the target nucleic acid. In the embodiments shown in FIG. 12A, the amplification products comprise the same locus-specific tag but different allele-specific tags. The amplification products are exposed to 1) a first allele-specific primer, which hybridizes to an "allele 1" allele-specific tag, and 2) a second allele-specific primer, which hybridizes to an "allele 2" allele-specific tag. In the embodiments shown in FIG. 12A, the allele-specific primers comprise different labels. The first allele-specific primer is extended to form a first allele-specific extension product (shown in FIGS. 12B and 12C), and the second allele-specific primer is extended to form a second allele-specific extension product (shown in FIGS. 12B and 12C).

In the embodiments shown in FIGS. 12B and 12C, both the first allele-specific extension product and the second allele-specific extension product comprise the same locus-specific tag. Accordingly, as shown in FIG. 12B, the extension products hybridize to a common locus-specific probe. In the embodiments shown in FIG. 12B, the common locus-specific probe is immobilized on a solid support, e.g., on a bead or at a particular position on an array. The labels detected on the solid support indicate which alleles are present in the target nucleic acid. For example, the presence of two labels on the solid support indicates the presence of two alleles (i.e., heterozygosity) in a given target nucleic acid, whereas the presence of only one label on the solid support indicates the presence of a single allele (homozygosity) in a given target nucleic acid.

In the embodiments shown in FIG. 12C, the extension products hybridize to one of two different probes that are both allele- and locus-specific. In FIG. 12C, the first probe comprises the "allele 1" allele-specific tag and the locus-specific tag, and the second probe comprises the "allele 2" allele-specific tag and the same locus-specific tag. In the embodiments shown in FIG. 12C, the first and second probes are immobilized on a solid support, e.g., on a bead or at a particular position on an array. Thus, the labels that are detected on the solid support indicate the alleles that are present in the target nucleic acid.

In certain embodiments, the allele-specific tag and the locus-specific tag in an amplification product are detected using a type II restriction endonuclease. A type II restriction endonuclease cleaves a nucleic acid at a site other than its recognition site. Exemplary type II restriction endonucleases include, but are not limited to, FokI and BsmFI. In certain embodiments, an allele-specific tag comprises a recognition site for a type II restriction endonuclease. In certain embodiments, different allele-specific tags comprise different recognition sites in order to distinguish among different alleles at a given locus. In certain embodiments, a type II endonuclease recognizes a recognition site in the allele-specific tag, but cleaves within the locus-specific tag in the amplification product. In certain such embodiments, the absence or presence of a cleavage product is detected, and thus, the absence or presence of the amplification product is detected. In certain such embodiments, the presence of a cleavage product indicates the presence of the allele corresponding to the allele-specific tag.

Figure 13:
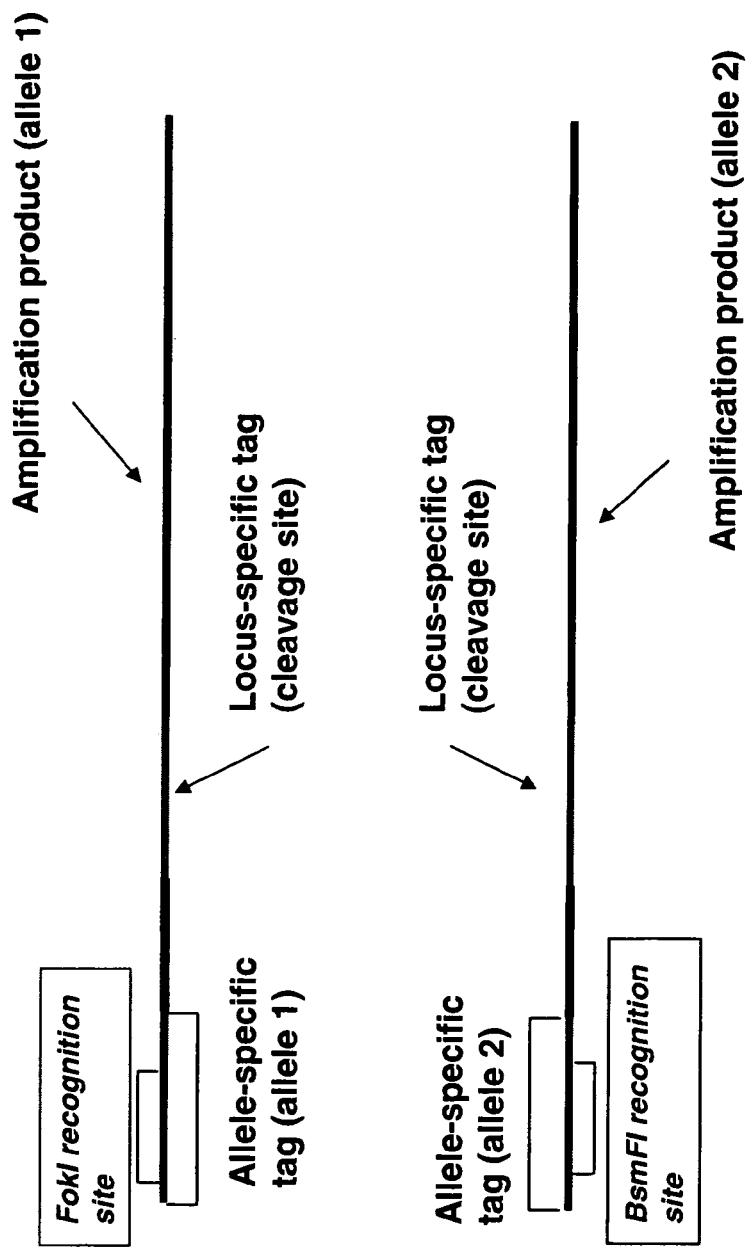
FIGS. 13A and 13B show certain exemplary embodiments of detection using type II restriction endonucleases.

FIG. 13 shows exemplary embodiments of detection using type II restriction endonucleases. FIG. 13A shows an amplification product specific for a first allele ("allele 1"). That amplification product comprises an "allele 1" allele-specific tag that is recognized by the type II restriction endonuclease FokI. In certain embodiments, when FokI recognizes the "allele 1" allele-specific tag in the amplification product, it cleaves the amplification product within the locus-specific tag. FIG. 13B shows an amplification product specific for a second allele ("allele 2"). That amplification product comprises an "allele 2" allele-specific tag that is recognized by the type II restriction endonuclease BsmFI. In certain embodiments, when BsmFI recognizes the "allele 2" allele-specific tag in the amplification product, it cleaves the amplification product within the locus-specific tag.

In certain embodiments, to determine whether a single reaction mixture contains either or both of the amplification products shown in FIG. 13, an aliquot of the reaction mixture is exposed to FokI, and a separate aliquot of the reaction mixture is exposed to BsmFI. The absence or presence of cleavage products in both reaction mixtures is detected, e.g., by detecting hybridization of all or a portion of the locus-specific tag to a complementary nucleic acid sequence.

One skilled in the art will understand that any of the above embodiments may be modified to detect the complements of the allele-specific tags and/or complements of the locus-specific tags. Certain other variations on any of the above embodiments are within the skill of one skilled in the art.

Certain Methods of Nucleic Acid Detection Using Spanning Primers

In certain embodiments, methods for detecting target nucleic acid sequences are present in a sample (or quantitating target nucleic acid sequences in a sample) are provided. In certain embodiments, a method for amplifying at least one target nucleic acid sequence is provided, comprising: forming an amplification reaction composition comprising: a target nucleic acid sequence; a polymerase; and a first primer comprising (i) a sequence complementary to the 5' end of the target nucleic acid sequence and (ii) a sequence complementary to the 3' end of the target nucleic acid sequence; and subjecting the amplification reaction composition to at least one amplification reaction to form at least one amplification product. In certain embodiments, the 3' end of the target nucleic acid sequence is blocked. In certain embodiments, the polymerase lacks exonuclease activity.

In certain embodiments, the amplification reaction composition further comprises dNTPs. In certain embodiments, the amplification reaction composition further comprises a buffering agent. In certain embodiments, the amplification reaction composition further comprises an additive.

In certain embodiments, the amplification reaction composition further comprises a second primer. In certain embodiments, the second primer comprises (i) a sequence complementary to the 3' end of a complement of the target nucleic acid sequence and (ii) a sequence complementary to any portion of the first primer. In certain such embodiments, the second primer comprises a thymidine between (i) the sequence complementary to the 3' end of a complement of the target nucleic acid sequence and (ii) the sequence complementary to any portion of the first primer. In certain embodiments, a second primer comprises (i) a sequence complementary to the 3' end of a complement of the target nucleic acid sequence and (ii) a sequence complementary to the 5' end of the first primer. In certain such embodiments, the second primer comprises a thymidine between (i) the sequence complementary to the 3' end of a complement of the target nucleic acid sequence and (ii) the sequence complementary to the 5' end of the first primer.

In certain embodiments, the first primer is a universal primer. In certain embodiments, the second primer is a universal primer. In certain embodiments, both the first and second primers are universal primers.

In certain embodiments, the amplification reaction comprises an annealing step that takes place at a predetermined annealing temperature. In certain embodiments, the annealing temperature of the first few cycles of amplification is from 62 to 66° C., including all temperatures between those endpoints, and is increased to at least 70° C. for subsequent cycles of amplification. In certain embodiments, the annealing temperature of the first few cycles of amplification is 65° C. and is increased to at least 70° C. for subsequent cycles of amplification. In certain embodiments, the first few cycles comprise two cycles. In certain embodiments, the first few cycles comprise three, four, or five cycles. In certain embodiments, the annealing temperature is 70° C. or greater.

In certain embodiments, the method for amplifying at least one target nucleic acid sequence further comprises detecting the at least one amplification product. In certain embodiments, the amplification reaction composition further comprises at least one probe. In certain embodiments, the at least one probe is detectably labeled. In certain embodiments, the at least one probe is specific for a sequence located within the first primer or a sequence complementary to a sequence located within the first primer. In certain embodiments, the at least one probe is specific for a sequence located within the second primer or a sequence complementary to a sequence located within the second primer. In certain embodiments, the at least one probe is specific for a sequence located within the target nucleic acid sequence or a sequence complementary to a sequence located within the target nucleic acid sequence.

In certain embodiments, methods for detecting whether target nucleic acid sequences are present in a sample (or quantitating target nucleic acid sequences in a sample) are provided. In certain embodiments, a method for determining whether at least one target nucleic acid sequence is present in a sample is provided, comprising: forming a ligation reaction composition comprising the sample and a ligation probe set for each target nucleic acid sequence, the ligation probe set comprising (a) a first probe, comprising a first target-specific portion, and (b) a second probe, comprising a second target-specific portion, wherein the probes in each set are suitable for ligation together when hybridized adjacent to one another on the corresponding target nucleic acid sequence; forming a first test composition by subjecting the ligation reaction composition to at least one cycle of ligation, wherein adjacently hybridizing complementary probes are ligated to one another to form a ligation product comprising the first probe and the second probe; forming an amplification reaction composition comprising: at least some of the first test composition; a polymerase; and a first primer comprising (i) a sequence complementary to the 5' end of the ligation product and (ii) a sequence complementary to the 3' end of the ligation product; forming a second test composition by subjecting the amplification reaction composition to at least one amplification reaction, wherein the second test composition comprises at least one amplification product if a target nucleic acid sequence is present in the sample, and determining whether the at least one target nucleic acid sequence is present by detecting at least one amplification product. In certain embodiments, the 3' end of the target nucleic acid sequence is blocked. In certain embodiments, the polymerase lacks exonuclease activity.

In certain embodiments, the amplification reaction composition comprises dNTPs. In certain embodiments, the amplification reaction composition comprises a buffering agent. In certain embodiments, the amplification reaction composition comprises an additive.

In certain embodiments, the ligation and amplification reactions are performed in separate reaction vessels. In certain embodiments, the ligation and amplification reactions are performed in a single reaction vessel. In certain embodiments, the ligation product is purified prior to amplification. In certain embodiments, the ligation product is not purified prior to amplification.

In certain embodiments, the first primer is a universal primer. In certain embodiments, the second primer is a universal primer. In certain embodiments, both the first and second primers are universal primers.

In certain embodiments, the amplification reaction comprises an annealing step that takes place at a predetermined annealing temperature. In certain embodiments, the annealing temperature of two first cycles of amplification is 65° C. and is increased to at least 70° C. for subsequent cycles of amplification. In certain embodiments, the annealing temperature is 70° C. or greater.

In certain embodiments, the amplification reaction composition further comprises a second primer. In certain embodiments, the second primer comprises (i) a sequence complementary to the 3' end of a complement of the target nucleic acid sequence and (ii) a sequence complementary to any portion of the first primer. In certain such embodiments, the second primer comprises a thymidine between (i) the sequence complementary to the 3' end of a complement of the target nucleic acid sequence and (ii) the sequence complementary to any portion of the first primer. In certain embodiments, a second primer comprises (i) a sequence complementary to the 3' end of a complement of the target nucleic acid sequence and (ii) a sequence complementary to the 5' end of the first primer. In certain such embodiments, the second primer comprises a thymidine between (i) the sequence complementary to the 3' end of a complement of the target nucleic acid sequence and (ii) the sequence complementary to the 5' end of the first primer.

In certain embodiments, each probe set further comprises a third probe comprising a third target specific portion, wherein the third target specific portion differs from the first target specific portion by at least one nucleotide. In certain embodiments, the first probe comprises a first addressable specific portion. In certain embodiments, the third probe comprises a second addressable specific portion. In certain embodiments, the second probe comprises a third addressable specific portion.

In certain embodiments, each target nucleic acid sequence contains at least one pivotal nucleotide, such that a first allele of the target nucleic acid sequence comprises a first nucleotide at the at least one pivotal nucleotide, and a second allele of the target nucleic acid sequence comprises a second nucleotide at the at least one pivotal nucleotide, and wherein the first nucleotide and the second nucleotide are different. In certain such embodiments, each probe set further comprises a third probe, comprising a third target specific portion, wherein the third target specific portion differs from the first target specific portion by at least one nucleotide, and wherein the first target specific portion comprises at least one pivotal complement for the first allele of the target nucleic acid sequence and the third target specific portion comprises at least one pivotal complement for the second allele of the target nucleic acid sequence.

In certain such embodiments, the first probe comprises a first addressable specific portion and the third probe comprises a second addressable specific portion, such that the presence of the first addressable specific portion in at least one amplification product indicates the presence of the first allele of the target nucleic acid sequence and the presence of the second addressable specific portion in at least one amplification product indicates the presence of the second allele of the target nucleic acid sequence. In certain such embodiments, the second probe comprises a third addressable specific portion, such that the presence of the third addressable specific portion in at least one amplification product indicates the presence of the pivotal nucleotide in the target nucleic acid sequence.

In certain such embodiments, the amplification reaction composition further comprises a second primer comprising a sequence complementary to the 3' end of a complement of the target nucleic acid sequence, and the detecting comprises one of the following methods. In certain embodiments, the detecting comprises: exposing at least some of the second test composition to (a) a first detection probe comprising (i) a sequence complementary to the first addressable specific portion and (ii) a sequence complementary to the third addressable specific portion; and (b) a second detection probe comprising (i) a sequence complementary to the second addressable specific portion and (ii) a sequence complementary to the third addressable specific portion; and detecting whether the first detection probe hybridizes to at least one amplification product to determine whether the first allele of the target nucleic acid sequence is present and detecting whether the second detection probe hybridizes to at least one amplification product to determine whether the second allele of the target nucleic acid sequence is present.

In certain embodiments, the detecting comprises: exposing at least some of the second test composition to a first restriction endonuclease and a second restriction endonuclease to produce a third test composition which comprises a cleavage product if at least one amplification product is present in the second test composition, wherein the first addressable specific portion has a recognition site for the first restriction endonuclease, the second addressable specific portion has a recognition site for the second restriction endonuclease, and wherein the cleavage site for the first restriction endonuclease and the second restriction endonuclease is within the third addressable specific portion of at least one amplification product; exposing the third test composition to a first detection probe comprising a sequence complementary to the first addressable specific portion and to a second detection probe comprising a sequence complementary to the second addressable specific portion; separating the hybridized cleavage product from unhybridized first detection probes and second detection probes; and detecting the presence or absence of the cleavage product.

In certain embodiments, the detecting comprises: forming a second ligation reaction composition comprising at least some of the second test composition, a first detection probe comprising a sequence complementary to the first addressable specific portion and a first label, a second detection probe comprising a second label and a sequence complementary to the second addressable specific portion, and a third detection probe comprising a sequence complementary to the third addressable specific portion, wherein the first detection probe and the third detection probe are suitable for ligation together when hybridized adjacent to one another on at least one amplification product, and wherein the second probe and the third probe are suitable for ligation together when hybridized adjacent to one another on at least one amplification product; forming a third test composition by subjecting the second ligation reaction composition to at least one cycle of ligation, wherein adjacently hybridizing complementary detection probes are ligated to one another to form a second ligation product comprising the first detection probe or the second detection probe and the third detection probe; separating the second ligation product from unligated first detection probes, second detection probes, and third detection probes; and detecting the presence or absence of the first label and the second label.

In certain embodiments, the detecting comprises: forming a second amplification reaction composition comprising at least some of the second test composition, a detection probe comprising a sequence complementary to the third addressable specific portion, a first PCR primer comprising a first label and a sequence complementary to the first addressable specific portion, a second PCR primer comprising a second label and a sequence complementary to the second addressable specific portion, and a polymerase, wherein the detection probe is attached to a solid support; subjecting the second amplification reaction composition to at least one amplification reaction; and detecting the presence or absence of the first label and the second label.

In certain embodiments, the detecting comprises: forming a second ligation reaction composition comprising at least some of the second test composition, a first detection probe comprising a first label and a sequence complementary to the first addressable specific portion, a second detection probe comprising a second label and a sequence complementary to the second addressable specific portion, and a third detection probe comprising a sequence complementary to the third addressable specific portion, wherein the first detection probe and the third detection probe are suitable for ligation together when hybridized adjacent to one another on at least one amplification product, and wherein the second detection probe and the third detection probe are suitable for ligation together when hybridized adjacent to one another on at least one amplification product, and wherein the third detection probe is attached to a solid support; forming a third test composition by subjecting the ligation reaction composition to at least one cycle of ligation, wherein adjacently hybridizing complementary probes are ligated to one another to form a second ligation product comprising the first detection probe or the second detection probe and the third detection probe; separating the second ligation product from unligated first detection probes and second detection probes; and detecting the presence or absence of the first label and the second label.

In certain embodiments, the detecting comprises: exposing the second test composition to at least two different sequence-specific mobility-modifiers, wherein each different mobility-modifier is capable of sequence-specific binding to a different addressable specific portion and comprises (a) a tag complement for specifically binding the addressable specific portion of at least one amplification product, and (b) a tail which imparts to each mobility modifier a mobility that is distinctive relative to the mobilities of one or more other of the at least two different mobility-modifiers in a mobility-dependent analysis technique; removing mobility-modifiers that are not sequence-specifically bound to the amplification reaction products from mobility-modifiers that are sequence-specifically bound to at least one amplification product; releasing the sequence-specifically bound mobility-modifiers from the amplification reaction products; subjecting the released mobility-modifiers to a mobility-dependent analysis technique; and detecting one or more target nucleic acid sequences by detecting distinctive positions of the mobility-modifiers. In certain such embodiments, at least one sequence-specific mobility modifier comprises a label. In certain embodiments, the mobility-dependent analysis technique is electrophoresis.

In certain embodiments, at least one amplification product comprises a first or second addressable specific portion that is four, five, six, seven, eight, nine, or ten nucleotides from the third addressable specific portion. In certain such embodiments, at least one amplification product comprises a first or second addressable specific portion that is eight nucleotides from the third addressable specific portion.

In certain embodiments, a method for determining whether at least one target nucleic acid sequence is present in a sample is provided, comprising: (a) forming a reaction composition comprising: the sample; a ligation probe set for each target nucleic acid sequence, the probe set comprising (a) at least one first probe, comprising a first target-specific portion and (b) at least one second probe, comprising a second target-specific portion, wherein the probes in each set are suitable for ligation together to form a ligation product when hybridized adjacent to one another on a complementary target nucleic acid sequence; a polymerase; and a first primer comprising (i) a sequence complementary to the 5' end of the ligation product and (ii) a sequence complementary to the 3' end of the ligation product; (b) subjecting the reaction composition to at least one cycle of ligation, wherein adjacently hybridizing complementary probes are ligated to one another to form a ligation product comprising the first probe and the second probe; (c) after the at least one cycle of ligation, subjecting the reaction composition to at least one amplification reaction to form at least one amplification product if a target nucleic acid sequence is present in the sample; and (d) determining whether the at least one target nucleic acid sequence is present by detecting at least one amplification product. In certain such embodiments, the quantity of target nucleic acid sequences in the sample is determined. In certain embodiments, the 3' end of the target nucleic acid sequence is blocked. In certain embodiments, the polymerase lacks exonuclease activity.

In certain embodiments, the amplification reaction composition comprises dNTPs. In certain embodiments, the amplification reaction composition comprises a buffering agent. In certain embodiments, the amplification reaction composition comprises an additive.

In certain embodiments, the ligation product is purified prior to amplification. In certain embodiments, the ligation product is not purified prior to amplification.

In certain embodiments, the amplification reaction comprises an annealing step that takes place at a predetermined annealing temperature. In certain embodiments, the annealing temperature of the first few cycles of amplification is from 62 to 66° C., including all temperatures between those endpoints, and is increased to at least 70° C. for subsequent cycles of amplification. In certain embodiments, the annealing temperature of the first few cycles of amplification is 65° C. and is increased to at least 70° C. for subsequent cycles of amplification. In certain embodiments, the first few cycles comprise two cycles. In certain embodiments, the first few cycles comprise three, four, or five cycles.

In certain embodiments, the amplification reaction composition further comprises a second primer. In certain embodiments, the second primer comprises (i) a sequence complementary to the 3' end of a complement of the target nucleic acid sequence and (ii) a sequence complementary to any portion of the first primer. In certain such embodiments, the second primer comprises a thymidine between (i) the sequence complementary to the 3' end of a complement of the target nucleic acid sequence and (ii) the sequence complementary to any portion of the first primer. In certain embodiments, the second primer comprises (i) a sequence complementary to the 3' end of a complement of the target nucleic acid sequence and (ii) a sequence complementary to the 5' end of the first primer. In certain such embodiments, the second primer comprises a thymidine between (i) the sequence complementary to the 3' end of a complement of the target nucleic acid sequence and (ii) the sequence complementary to the 5' end of the first primer.

In certain embodiments, each probe set further comprises a third probe comprising a third target specific portion, wherein the third target specific portion differs from the first target specific portion by at least one nucleotide. In certain embodiments, the first probe comprises a first addressable specific portion. In certain embodiments, the third probe comprises a second addressable specific portion. In certain embodiments, the second probe comprises a third addressable specific portion.

In certain embodiments, each target nucleic acid sequence contains at least one pivotal nucleotide, such that a first allele of the target nucleic acid sequence comprises a first nucleotide at the at least one pivotal nucleotide, and a second allele of the target nucleic acid sequence comprises a second nucleotide at the at least one pivotal nucleotide, and wherein the first nucleotide and the second nucleotide are different. In certain such embodiments, each probe set further comprises a third probe, comprising a third target specific portion, wherein the third target specific portion differs from the first target specific portion by at least one nucleotide, and wherein the first target specific portion comprises at least one pivotal complement for the first allele of the target nucleic acid sequence and the third target specific portion comprises at least one pivotal complement for the second allele of the target nucleic acid sequence.

In certain such embodiments, the first probe comprises a first addressable specific portion and the third probe comprises a second addressable specific portion, such that the presence of the first addressable specific portion in at least one amplification product indicates the presence of the first allele of the target nucleic acid sequence and the presence of the second addressable specific portion in at least one amplification product indicates the presence of the second allele of the target nucleic acid sequence. In certain such embodiments, the second probe comprises a third addressable specific portion, such that the presence of the third addressable specific portion in at least one amplification product indicates the presence of the pivotal nucleotide in the target nucleic acid sequence.

In certain such embodiments, the amplification reaction composition further comprises a second primer comprising a sequence complementary to the 3' end of a complement of the target nucleic acid sequence, and the detecting comprises one of the following methods. In certain embodiments, the detecting comprises: exposing at least some of the second test composition to (a) a first detection probe comprising (i) a sequence complementary to the first addressable specific portion and (ii) a sequence complementary to the third addressable specific portion; and (b) a second detection probe comprising (i) a sequence complementary to the second addressable specific portion and (ii) a sequence complementary to the third addressable specific portion; and detecting whether the first detection probe hybridizes to at least one amplification product to determine whether the first allele of the target nucleic acid sequence is present and detecting whether the second detection probe hybridizes to at least one amplification product to determine whether the second allele of the target nucleic acid sequence is present.

In certain embodiments, the detecting comprises: exposing at least some of the second test composition to a first restriction endonuclease and a second restriction endonuclease to produce a third test composition which comprises a cleavage product if at least one amplification product is present in the second test composition, wherein the first addressable specific portion has a recognition site for the first restriction endonuclease, the second addressable specific portion has a recognition site for the second restriction endonuclease, and wherein the cleavage site for the first restriction endonuclease and the second restriction endonuclease is within the third addressable specific portion of at least one amplification product; exposing the third test composition to a first detection probe comprising a sequence complementary to the first addressable specific portion and to a second detection probe comprising a sequence complementary to the second addressable specific portion; separating the hybridized cleavage product from unhybridized first detection probes and second detection probes; and detecting the presence or absence of the cleavage product.

In certain embodiments, the detecting comprises: forming a second ligation reaction composition comprising at least some of the second test composition, a first detection probe comprising a sequence complementary to the first addressable specific portion and a first label, a second detection probe comprising a second label and a sequence complementary to the second addressable specific portion, and a third detection probe comprising a sequence complementary to the third addressable specific portion, wherein the first detection probe and the third detection probe are suitable for ligation together when hybridized adjacent to one another on at least one amplification product, and wherein the second probe and the third probe are suitable for ligation together when hybridized adjacent to one another on at least one amplification product; forming a third test composition by subjecting the second ligation reaction composition to at least one cycle of ligation, wherein adjacently hybridizing complementary detection probes are ligated to one another to form a second ligation product comprising the first detection probe or the second detection probe and the third detection probe; separating the second ligation product from unligated first detection probes, second detection probes, and third detection probes; and detecting the presence or absence of the first label and the second label.

In certain embodiments, the detecting comprises: forming a second amplification reaction composition comprising at least some of the second test composition, a detection probe comprising a sequence complementary to the third addressable specific portion, a first PCR primer comprising a first label and a sequence complementary to the first addressable specific portion, a second PCR primer comprising a second label and a sequence complementary to the second addressable specific portion, and a polymerase, wherein the detection probe is attached to a solid support; subjecting the second amplification reaction composition to at least one amplification reaction; and detecting the presence or absence of the first label and the second label.

In certain embodiments, the detecting comprises: forming a second ligation reaction composition comprising at least some of the second test composition, a first detection probe comprising a first label and a sequence complementary to the first addressable specific portion, a second detection probe comprising a second label and a sequence complementary to the second addressable specific portion, and a third detection probe comprising a sequence complementary to the third addressable specific portion, wherein the first detection probe and the third detection probe are suitable for ligation together when hybridized adjacent to one another on at least one amplification product, and wherein the second detection probe and the third detection probe are suitable for ligation together when hybridized adjacent to one another on at least one amplification product, and wherein the third detection probe is attached to a solid support; forming a third test composition by subjecting the ligation reaction composition to at least one cycle of ligation, wherein adjacently hybridizing complementary probes are ligated to one another to form a second ligation product comprising the first detection probe or the second detection probe and the third detection probe; separating the second ligation product from unligated first detection probes and second detection probes; and detecting the presence or absence of the first label and the second label.

In certain embodiments, the detecting comprises: exposing the second test composition to at least two different sequence-specific mobility-modifiers, wherein each different mobility-modifier is capable of sequence-specific binding to a different addressable specific portion and comprises (a) a tag complement for specifically binding the addressable specific portion of at least one amplification product, and (b) a tail which imparts to each mobility modifier a mobility that is distinctive relative to the mobilities of one or more other of the at least two different mobility-modifiers in a mobility-dependent analysis technique; removing mobility-modifiers that are not sequence-specifically bound to the amplification reaction products from mobility-modifiers that are sequence-specifically bound to at least one amplification product; releasing the sequence-specifically bound mobility-modifiers from the amplification reaction products; subjecting the released mobility-modifiers to a mobility-dependent analysis technique; and detecting one or more target nucleic acid sequences by detecting distinctive positions of the mobility-modifiers. In certain such embodiments, at least one sequence-specific mobility modifier comprises a label. In certain embodiments, the mobility-dependent analysis technique is electrophoresis.

In certain embodiments, at least one amplification product comprises a first or second addressable specific portion that is four, five, six, seven, eight, nine, or ten nucleotides from the third addressable specific portion. In certain such embodiments, at least one amplification product comprises a first or second addressable specific portion that is eight nucleotides from the third addressable specific portion.

Certain Exemplary Kits

In certain embodiments, kits are provided that are designed to expedite performing certain methods. In certain embodiments, kits serve to expedite the performance of the methods of interest by assembling two or more components used in carrying out the methods. In certain embodiments, kits may contain components in pre-measured unit amounts to minimize the need for measurements by end-users. In certain embodiments, kits may include instructions for performing one or more methods. In certain embodiments, the kit components are optimized to operate in conjunction with one another.

In certain embodiments, a kit for amplifying at least one target nucleic acid sequence is provided. In certain embodiments, a kit comprises a polymerase and a first primer comprising (i) a sequence complementary to the 5' end of the target nucleic acid sequence and (ii) a sequence complementary to the 3' end of the target nucleic acid sequence. In certain embodiments, the kit further comprises a second primer. In certain embodiments, the second primer comprises (i) a sequence complementary to the 3' end of a complement of the target nucleic acid sequence and (ii) a sequence complementary to the 5' end of the first primer. In certain embodiments, a second primer comprises (i) a sequence complementary to the 3' end of a complement of the target nucleic acid sequence and (ii) a sequence complementary to any portion of the first primer. In certain embodiments, the kit comprises dNTPs. In certain embodiments, the kit comprises one or more buffering agents. In certain embodiments, the kit comprises one or more additives. In certain embodiments, the kit further comprises instructions for use.

In certain embodiments, a kit comprises a ligation probe set for each target nucleic acid sequence, wherein the probe set comprises (a) a first probe, comprising a first target-specific portion, and (b) a second probe, comprising a second target-specific portion, wherein the probes in each set are suitable for ligation together when hybridized adjacent to one another on a complementary target sequence. In certain embodiments, a kit further comprises a polymerase and a first primer comprising (i) a sequence complementary to the 5' end of the target nucleic acid sequence and (ii) a sequence complementary to the 3' end of the target nucleic acid sequence. In certain embodiments, a kit further comprises a second primer. In certain embodiments the second primer comprises (i) a sequence complementary to the 3' end of a complement of the target nucleic acid sequence and (ii) a sequence complementary to the 5' end of the first primer. In certain embodiments, the kit comprises a ligase. In certain embodiments, the kit comprises dNTPs. In certain embodiments, the kit comprises one or more buffering agents.

In certain embodiments, the kit comprises one or more additives. In certain embodiments, the kit comprises instructions for use.

Certain Components for Ligation

Certain Target Nucleic Acids

Exemplary target nucleic acid sequences include, but are not limited to, RNA and DNA. Exemplary RNA target sequences include, but are not limited to, mRNA, snRNA, rRNA, tRNA, viral RNA, and variants of RNA, such as splicing variants. Exemplary DNA target sequences include, but are not limited to, genomic DNA, plasmid DNA, phage DNA, nucleolar DNA, mitochondrial DNA, and chloroplast DNA.

Exemplary target nucleic acid sequences include, but are not limited to, cDNA, yeast artificial chromosomes (YAC's), bacterial artificial chromosomes (BAC's), other extrachromosomal DNA, and nucleic acid analogs. Exemplary nucleic acid analogs include, but are not limited to, LNAs, PNAs, PPGs (e.g., pyrazolopyrimidine G), and other nucleic acid analogs.

A variety of methods are available for obtaining a target nucleic acid sequence for use with certain compositions and methods of the present teachings. When the nucleic acid target is obtained through isolation from a biological matrix, certain isolation techniques include, but are not limited to, (1) organic extraction followed by ethanol precipitation, e.g., using a phenol/chloroform organic reagent (e.g., Ausubel et al., eds., *Current Protocols in Molecular Biology Volume* 1, Chapter 2, Section I, John Wiley & Sons, New York (1993)), in certain embodiments, using an automated DNA extractor, e.g., the Model 341 DNA Extractor available from Applied Biosystems (Foster City, Calif.); (2) stationary phase adsorption methods (e.g., Boom et al., U.S. Pat. No. 5,234,809; Walsh et al., *Biotechniques* 10(4): 506-513 (1991)); and (3) salt-induced DNA precipitation methods (e.g., Miller et al., *Nucleic Acids Research,* 16(3): 9-10 (1988)), such precipitation methods being typically referred to as "salting-out" methods. In certain embodiments, the above isolation methods may be preceded by an enzyme digestion step to help eliminate unwanted protein from the sample, e.g., digestion with proteinase K, or other like proteases. See, e.g., Published U.S. Patent Application No. 2005/0009045.

In certain embodiments, a target nucleic acid sequence may be derived from any living, or once living, organism, including but not limited to prokaryote, eukaryote, plant, animal, and virus. In certain embodiments, the target nucleic acid sequence may originate from a nucleus of a cell, e.g., genomic DNA, or may be extranuclear nucleic acid, e.g., plasmid, mitochondrial nucleic acid, various RNAs, and the like. In certain embodiments, if the sequence from the organism is RNA, it may be reverse-transcribed into a cDNA target nucleic acid sequence. Furthermore, in certain embodiments, the target nucleic acid sequence may be present in a double stranded or single stranded form.

Exemplary target nucleic acid sequences include, but are not limited to, amplification products, ligation products, reverse transcription products, primer extension products, methylated DNA, and cleavage products. Exemplary amplification products include, but are not limited to, PCR and products of certain isothermal amplification techniques.

In certain embodiments, nucleic acids in a sample may be subjected to a cleavage or fragmentation procedure. In certain embodiments, such cleavage products and/or fragments may comprise targets.

Different target nucleic acid sequences may be different portions of a single contiguous nucleic acid or may be on different nucleic acids. Different portions of a single contiguous nucleic acid may or may not overlap.

The person of ordinary skill will appreciate that while a target nucleic acid sequence is typically described as a single-stranded molecule, the opposing strand of a double-stranded molecule comprises a complementary sequence that may also be used as a target sequence.

Certain Ligation Probe Sets

A ligation probe set, according to certain embodiments, comprises two or more probes that comprise a target-specific portion that is designed to hybridize in a sequence-specific manner with a complementary region on a specific target nucleic acid sequence (see, e.g., FIG. 5). In certain embodiments, a probe of a ligation probe set may further comprise a primer-specific portion, and/or an addressable portion, or a combination of these additional components. In certain embodiments, any of the probe's components may overlap any other probe component(s). For example, but without limitation, the target-specific portion may overlap the primer-specific portion. Also, without limitation, the addressable portion may overlap with the target-specific portion or the primer specific-portion, or both.

In certain embodiments, at least one probe of a ligation probe set comprises the addressable portion located between the target-specific portion and the primer-specific portion. In certain embodiments, the probe's addressable portion may comprise a sequence that is the same as, or is complementary to, at least a portion of a labeled probe. In certain embodiments, the probe's primer-specific portion may comprise a sequence that is the same as, or is complementary to, at least a portion of a labeled probe. In certain embodiments, the probe's addressable portion is not complementary with target sequences, primer sequences, or probe sequences other than complementary portions of labeled probes.

The sequence-specific portions of probes are of sufficient length to permit specific annealing to complementary sequences in primers, addressable portions, and/or targets as appropriate. In certain embodiments, the length of the addressable portions and target-specific portion are any number of nucleotides from 6 to 35. In certain embodiments, the length of the addressable portions and target-specific portion is greater than 35. Detailed descriptions of probe design that provide for sequence-specific annealing can be found, among other places, in Dieffenbach and Dveksler, PCR Primer, A Laboratory Manual, Cold Spring Harbor Press (1995), and Kwok et al., Nucl. Acids Res. 18:999-1005 (1990).

Under appropriate conditions, adjacently hybridized probes may be ligated together to form a ligation product, provided that they comprise appropriate reactive groups, for example, without limitation, a free 3'-hydroxyl and 5'-phosphate group.

According to certain embodiments, some ligation probe sets may comprise more than one first probe or more than one second probe to allow sequence discrimination between target sequences that differ by one or more nucleotides.

The skilled artisan will appreciate that, in various embodiments, a pivotal nucleotide(s) may be located anywhere in the target sequence and that likewise, a pivotal complement(s) may be located anywhere within a target-specific portion of the probe(s). For example, according to various embodiments, the pivotal complement may be located at the 3' end of a probe, at the 5' end of a probe, or anywhere between the 3' end and the 5' end of a probe.

In certain embodiments, certain mechanisms may be employed to avoid ligation of probes that do not include the correct complementary nucleotide at the pivotal complement. For example, in certain embodiments, conditions may be employed such that a probe of a ligation probe set will hybridize to the target sequence to a measurably lesser extent if there is a mismatch at the pivotal nucleotide. Thus, in such embodiments, such non-hybridized probes will not be ligated to the other probe in the probe set.

In certain embodiments, the first probes and second probes in a ligation probe set are designed with similar melting temperatures ($T_m$). Where a probe includes a pivotal complement, in certain embodiments, the $T_m$ for the probe(s) comprising the pivotal complement(s) of the target pivotal nucleotide sought will be approximately 4-15° C. lower than the other probe(s) that do not contain the pivotal complement in the probe set. In certain such embodiments, the probe comprising the pivotal complement(s) will also be designed with a $T_m$ near the ligation temperature. Thus, a probe with a mismatched nucleotide will more readily dissociate from the target at the ligation temperature. The ligation temperature, therefore, in certain embodiments provides another way to discriminate between, for example, multiple potential alleles in the target.

Further, in certain embodiments, ligation probe sets do not comprise a pivotal complement at the terminus of the first or the second probe (e.g., at the 3' end or the 5' end of the first or second probe). Rather, the pivotal complement is located somewhere between the 5' end and the 3' end of the first or second probe. In certain such embodiments, probes with target-specific portions that are fully complementary with their respective target regions will hybridize under high stringency conditions. Probes with one or more mismatched bases in the target-specific portion, by contrast, will hybridize to their respective target region to a measurably lesser extent. Both the first probe and the second probe must be hybridized to the target for a ligation product to be generated.

In certain embodiments, highly related sequences that differ by as little as a single nucleotide can be distinguished. For example, according to certain embodiments, one can distinguish the two potential alleles in a biallelic locus as follows. One can combine a ligation probe set comprising two first probes, differing in their addressable portions and their pivotal complement, one second probe, and the sample containing the target. All three probes will hybridize with the target sequence under appropriate conditions. Only the first probe with the hybridized pivotal complement, however, will be ligated efficiently to the hybridized second probe. Thus, if only one allele is present in the sample, only one ligation product for that target will be generated. Both ligation products would be formed in a sample from a heterozygous individual. In certain embodiments, ligation of probes with a pivotal complement that is not complementary to the pivotal nucleotide may occur, but such ligation occurs to a measurably lesser extent than ligation of probes with a pivotal complement that is complementary to the pivotal nucleotide.

Certain Components for Detection

Many different signal moieties may be used in various embodiments. For example, exemplary signal moieties include, but are not limited to, fluorophores, radioisotopes, chromogens, enzymes, antigens, heavy metals, dyes, phosphorescence groups, chemiluminescent groups, and electrochemical detection moieties. Exemplary fluorophores that may be used as signal moieties include, but are not limited to, rhodamine, cyanine 3 (Cy 3), cyanine 5 (Cy 5), fluorescein, Vic™, LiZ™, Tamra™, 5-Fam™, 6-Fam™, and Texas Red (Molecular Probes). (Vic™, LiZ™, Tamra™, 5-Fam™, and 6-Fam™ (all available from Applied Biosystems, Foster City, Calif.) Exemplary radioisotopes include, but are not limited to, $^{32}P$, $^{33}P$, and $^{35}S$. Signal moieties include elements of multi-element indirect reporter systems, e.g., biotin/avidin, antibody/antigen, ligand/receptor, enzyme/substrate, and the like, in which the element interacts with other elements of the system in order to effect a detectable signal. Certain exemplary multi-element systems include, but are not limited to, a biotin reporter group attached to a probe and an avidin conjugated with a fluorescent label. Certain detailed protocols for methods of attaching signal moieties to oligonucleotides can be found in, among other places, G. T. Hermanson, Bioconjugate Techniques, Academic Press, San Diego, Calif. (1996) and S. L. Beaucage et al., Current Protocols in Nucleic Acid Chemistry, John Wiley & Sons, New York, N.Y. (2000).

As discussed above, the term "interaction probe" refers to a probe that comprises at least two moieties that can interact with one another to provide a detectably different signal value depending upon whether a given nucleic acid sequence is present or absent. In certain embodiments, one of the moieties is a signal moiety and the other moiety is a quencher moiety. The signal value that is detected from the signal moiety is different depending on whether the quencher moiety is sufficiently close to the signal moiety or is spaced apart from the signal moiety. In certain embodiments, the quencher moiety decreases the detectable signal value from the signal moiety when the quencher moiety is sufficiently close to the signal moiety. In certain embodiments, the quencher moiety decreases the detectable signal value to zero or close to zero when the quencher moiety is sufficiently close to the signal moiety.

In certain embodiments, one of the moieties of the interaction probe is a signal moiety and the other moiety is a donor moiety. The signal value that is detected from the signal moiety is different depending on whether the donor moiety is sufficiently close to the signal moiety or is spaced apart from the signal moiety. In certain embodiments, the donor moiety increases the detectable signal value from the signal moiety when the donor moiety is sufficiently close to the signal moiety. In certain embodiments, the detectable signal value is zero or close to zero when the donor moiety is not sufficiently close to the signal moiety.

In certain embodiments employing a donor moiety and signal moiety, one may use certain energy-transfer fluorescent dyes. Certain nonlimiting exemplary pairs of donors (donor moieties) and acceptors (signal moieties) are illustrated, e.g., in U.S. Pat. Nos. 5,863,727; 5,800,996; and 5,945,526. Use of certain such combinations of a donor and an acceptor have also been called FRET (Fluorescent Resonance Energy Transfer).

In certain embodiments, the moieties of the interaction probe are linked to one another by a link element such as, but not limited to, an oligonucleotide. In certain such embodiments, the presence of a sequence that hybridizes to an interaction probe impacts the proximity of the moieties to one another during the methods described herein. In various embodiments, the moieties may be attached to the link element in various ways known in the art. For example, certain nonlimiting protocols for attaching moieties to oligonucleotides are found in, among other places, G. T. Hermanson, Bioconjugate Techniques, Academic Press, San Diego, Calif. (1996) and S. L. Beaucage et al., Current Protocols in Nucleic Acid Chemistry, John Wiley & Sons, New York, N.Y. (2000). In certain embodiments, an interaction probe comprises more than one signal moiety. In certain embodiments, an interaction probe comprises more than one quencher moiety. In certain embodiments, an interaction probe comprises more than one donor moiety.

According to certain embodiments, the interaction probe may be a "5'-nuclease probe," which comprises a signal moiety linked to a quencher moiety or a donor moiety through a short oligonucleotide link element. When the 5'-nuclease probe is intact, the quencher moiety or the donor moiety influences the detectable signal from the signal moiety. According to certain embodiments, the 5'-nuclease probe binds to a specific nucleic acid sequence, and is cleaved by a polymerase or other polypeptide having 5' nuclease activity when the probe is replaced by a newly polymerized strand during an amplification reaction such as PCR or some other strand displacement protocol.

When the oligonucleotide link element of the 5'-nuclease probe is cleaved, the detectable signal from the signal moiety changes when the signal moiety becomes further separated from the quencher moiety or the donor moiety. In certain such embodiments that employ a quencher moiety, the signal value increases when the signal moiety becomes further separated from the quencher moiety. In certain such embodiments that employ a donor moiety, the signal value decreases when the signal moiety becomes further separated from the donor moiety.

In certain embodiments, the 5'-nuclease probe is a 5'-nuclease fluorescent probe, in which the signal moiety is a fluorescent moiety and the quencher moiety is a fluorescence quencher moiety. When the probe is cleaved during a strand displacement protocol, the fluorescent moiety emits a detectable fluorescent signal. In certain embodiments, a 5'-nuclease fluorescent probe may emit a given level of signal when it is hybridized to a complementary sequence prior to cleavage, and the level of the signal is increased with cleavage. Certain exemplary embodiments of 5'-nuclease fluorescent probes are described, e.g., in U.S. Pat. No. 5,538,848, and exemplified by the TaqMan® probe molecule, which is part of the TaqMan® assay system (available from Applied Biosystems, Foster City, Calif.).

According to certain embodiments, the interaction probe may be a "hybridization dependent probe," which comprises a signal moiety linked to a quencher moiety or a donor moiety through an oligonucleotide link element. When the hybridization dependent probe is not bound to a given nucleic acid sequence, and is thus single stranded, the oligonucleotide link element can bend flexibly, and the quencher moiety or the donor moiety is sufficiently close to the signal moiety to influence the detectable signal from the signal moiety. In certain embodiments, the oligonucleotide link element of a hybridization dependent probe is designed such that when it is not hybridized to a given nucleic acid sequence, it folds back and hybridizes to itself, e.g., a molecular beacon probe. See, e.g., U.S. Pat. Nos. 5,118,801; 5,312,728; and 5,925,517. In certain embodiments, the oligonucleotide link element of a hybridization dependent probe does not hybridize to itself when it is not hybridized to the given nucleic acid sequence.

When a hybridization dependent probe is bound to a given nucleic acid as double stranded nucleic acid, the quencher moiety or the donor moiety is spaced apart from the signal moiety such that the detectable signal is changed. In certain such embodiments that employ a quencher moiety, the signal value increases when the signal moiety becomes further separated from the quencher moiety. In certain such embodiments that employ a donor moiety, the signal value decreases when the signal moiety becomes further separated from the donor moiety.

In certain embodiments of hybridization dependent probes, the signal moiety is a fluorescent moiety and the quencher moiety is a fluorescence quencher moiety. When the probe is hybridized to a specific nucleic acid sequence, the fluorescent moiety emits a detectable fluorescent signal.

When the probe is not hybridized to a nucleic acid sequence and is intact, quenching occurs and little or no fluorescence is detected.

Certain exemplary embodiments of hybridization dependent probes are described, e.g., in U.S. Pat. No. 5,723,591.

In certain embodiments, one employs nucleic acids in the hybridization dependent probes such that a substantial portion of the hybridization dependent probes are not cleaved by an enzyme during an amplification reaction. A "substantial portion of the hybridization dependent probes are not cleaved" refers to a portion of the total number of hybridization dependent probes that are designed to hybridize to a given nucleic sequence that is being amplified, and it does not refer to a portion of an individual probe. In certain embodiments, "a substantial portion of hybridization dependent probes that are not cleaved" means that at least 90% of the hybridization dependent probes are not cleaved. In certain embodiments, at least 95% of the hybridization dependent probes are not cleaved. In certain embodiments, one employs PNA for some or all of the nucleic acids of a hybridization dependent probe.

In certain embodiments, one employs hybridization dependent probes in which a substantial portion of the hybridization dependent probes do not hybridize to an addressable portion or a complement of the addressable portion during an extension reaction. A "substantial portion of the hybridization dependent probes do not hybridize" here refers to a portion of the total number of hybridization dependent probes that are designed to hybridize to a given nucleic sequence that is being amplified, and it does not refer to a portion of an individual probe. In certain embodiments, "a substantial portion of hybridization dependent probes that do not hybridize" means that at least 90% of the hybridization dependent probes do not hybridize. In certain embodiments, at least 95% of the hybridization dependent probes do not hybridize.

According to certain embodiments, the interaction probe may comprise two oligonucleotides that hybridize to a given nucleic acid sequence adjacent to one another. In certain embodiments, one of the oligonucleotides comprises a signal moiety and one of the oligonucleotides comprises a quencher moiety or a donor moiety. When both oligonucleotides are hybridized to the given nucleic acid sequence, the quencher moiety or the donor moiety is sufficiently close to the signal moiety to influence the detectable signal from the signal moiety.

In certain such embodiments that employ a donor moiety, the signal value increases when the two oligonucleotides are hybridized to the given nucleic acid sequence. In certain such embodiments that employ a quencher moiety, the signal value decreases when the two oligonucleotides are hybridized to the given nucleic acid sequence. In certain embodiments, the signal moiety is a fluorescent moiety.

Other examples of suitable interaction probes according to various embodiments are i-probes, scorpion probes, eclipse probes, and others. Exemplary, but nonlimiting, probes are discussed, for example, in Whitcombe et al., Nat. Biotechnol., 17(8):804-807 (1999) (includes scorpion probes); Thelwell et al., Nucleic Acids Res., 28(19):3752-3761 (2000) (includes scorpion probes); Afonina et al., Biotechniques, 32(4):940-944, 946-949 (2002) (includes eclipse probes); Li et al., Nuc. Acids Res., 30(2):E5 (2002); Kandimall et al., Bioorg. Med. Chem., 8(8):1911-1916 (2000); Isacsson et al., Mol. Cell. Probes, 14(5):321-328 (2000); French et al, Mol. Cell. Probes, 15(6):363-374 (2001); and Nurmi et al., Nuc. Acids Res., 28(8), E28 (2000). Exemplary quencher moieties according to certain embodiments may be those available from Epoch Biosciences, Bothell, Wash.

In certain embodiments, one may use a labeled probe and a threshold difference between first and second detectable signal values to detect the presence or absence of a target nucleic acid in a sample. In such embodiments, if the difference between the first and second detectable signal values is the same as or greater than the threshold difference, i.e., there is a threshold difference, one concludes that the target nucleic acid is present. If the difference between the first and second detectable signal values is less than the threshold difference, i.e., there is no threshold difference, one concludes that the target nucleic acid is absent.

Certain nonlimiting examples of how one may set a threshold difference according to certain embodiments follow.

First, in certain embodiments, a labeled probe that is not hybridized to a complementary sequence may have a first detectable signal value of zero. In certain embodiments, when one forms an amplification reaction composition comprising the labeled probe, and any unligated ligation probes and ligation products that include complementary addressable portions, before amplification, the detectable signal value may increase to 0.4. In certain such embodiments, when such an amplification reaction composition does not include any ligation products comprising the complementary addressable portion, the detectable signal value may remain at 0.4 during and/or after an amplification reaction. (In other words, the second detectable signal value is 0.4.) In certain such embodiments, when such an amplification reaction composition, however, includes a ligation product comprising a complementary addressable portion, the detectable signal value may increase to 2 during and/or after an amplification reaction. (In other words, the second detectable signal value is 2.)

Thus, in certain such embodiments, one may set a threshold difference between first and second detectable signal values at a value somewhere between a value just above 0.4 to about 2. For example, one may set the threshold difference at somewhere between 0.5 to 2.

Second, in certain embodiments, a labeled probe that is not hybridized to a complementary sequence may have a first detectable signal value of zero. In certain embodiments, when one forms an amplification reaction composition comprising the labeled probe, and any unligated ligation probes and ligation products that include complementary addressable portions, before amplification, the detectable signal value may increase to 0.4. In certain such embodiments, when such an amplification reaction composition does not include any ligation products comprising the complementary addressable portion, the detectable signal value may increase to 0.7 during and/or after an amplification reaction. (In other words, the second detectable signal value is 0.7.) In certain such embodiments, when such an amplification reaction composition, however, includes a ligation product comprising a complementary addressable portion, the detectable signal value may increase to 2 during and/or after an amplification reaction. (In other words, the second detectable signal value is 2.)

Thus, in certain such embodiments, one may set a threshold difference between first and second detectable signal values at a value somewhere between a value just above 0.7 to about 2. For example, one may set the threshold difference at somewhere between 0.8 to 2.

Third, in certain embodiments, a labeled probe that is not hybridized to a complementary sequence may have a first detectable signal value of zero. In certain embodiments, when one forms an amplification reaction composition comprising the labeled probe, and any unligated ligation probes and ligation products that include complementary addressable portions, before amplification, the detectable signal value may increase to 0.4. In certain embodiments, when such an amplification reaction composition does not include any ligation products comprising the complementary addressable portion, the detectable signal value may increase linearly during and/or after an amplification reaction. (In other words, the second detectable signal value is linearly increased from the first detectable signal value.) In certain such embodiments, when such an amplification reaction composition, however, includes a ligation product comprising a complementary addressable portion, the detectable signal value may increase exponentially during and/or after an amplification reaction. (In other words, the second detectable signal value is exponentially increased from the first detectable signal value.)

Thus, in certain such embodiments, one may measure detectable signal values at two or more points during amplification, and at the end of the amplification reaction, to determine if the increase in detectable signal value is linear or exponential. In certain embodiments, one may measure detectable signal values at three or more points during amplification to determine if the increase in detectable signal value is linear or exponential. In certain embodiments, if the increase is exponential, there is a threshold difference between the first and second detectable signal values.

In certain embodiments, one may employ different labeled probes that are specific to different addressable portions. In certain such embodiments, one may employ different labeled probes that comprise different sequences and detectably different signal moieties. Detectably different signal moieties include, but are not limited to, moieties that emit light of different wavelengths, moieties that absorb light of different wavelengths, moieties that have different fluorescent decay lifetimes, moieties that have different spectral signatures, and moieties that have different radioactive decay properties.

In certain embodiments, one may employ a labeled probe that remains intact unless a particular nucleic acid sequence is present. A label is attached to the probe. If the particular nucleic acid is present, the probe will be cleaved. Certain examples, of such probes include, but are not limited to, probes that are cleaved by 5' nuclease activity during an extension reaction and probes that are cleaved by RNase H or another agent with similar activity.

In certain such embodiments, the cleaved portion of the probe with the label can be separated from intact probes in view of different migration rates of the cleaved portion of the probe and the intact probe using a method such as a "mobility-dependent analysis technique." A "mobility-dependent analysis technique" refers to any analysis based on different rates of migration between different analytes. Exemplary mobility-dependent analysis techniques include, but are not limited to, electrophoresis, mass spectroscopy, chromatography, sedimentation, gradient centrifugation, field-flow fractionation, and multi-stage extraction techniques. Thus, in such embodiments, one may determine the presence or absence of (or quantitate) a particular nucleic acid sequence in a sample by detecting the presence of (or quantitating) labeled cleaved portions of the labeled probe.

In certain embodiments, one may employ a mobility modifier to separate different cleaved portions of labeled probes from one another. For example, in certain such embodiments, different labeled probes with the same label could be used for different loci if the labeled probes for each different loci had a different mobility modifier. In certain embodiments, mobility modifiers may be oligonucleotides of different lengths effecting different mobilities. In certain embodiments, mobility modifiers may be non-nucleotide polymers, such as a polyethylene oxide (PEO), polyglycolic acid, polyurethane polymers, polypeptides, or oligosaccharides, as non-limiting examples. In certain embodiments, mobility modifiers may work by adding size to a polynucleotide, or by increasing the "drag" of the molecule during migration through a medium without substantially adding to the size. Certain mobility modifiers such as PEO's have been described, e.g., in U.S. Pat. Nos. 5,470,705; 5,580,732; 5,624,800; and 5,989,871.

Certain Primers

A primer set according to certain embodiments comprises at least one primer capable of hybridizing with the primer-specific portion of at least one probe of a ligation probe set. In certain embodiments, a primer set comprises at least one first primer and at least one second primer, wherein the at least one first primer specifically hybridizes with one probe of a ligation probe set (or a complement of such a probe) and the at least one second primer of the primer set specifically hybridizes with a second probe of the same ligation probe set (or a complement of such a probe). In certain embodiments, the first and second primers of a primer set have different hybridization temperatures, to permit temperature-based asymmetric PCR reactions. In certain embodiments, the primer set comprises at least one spanning primer.

The skilled artisan will appreciate that while probes and primers may be described in the singular form, a plurality of probes or primers may be encompassed by the singular term, as will be apparent from the context. Thus, for example, in certain embodiments, a ligation probe set typically comprises a plurality of first probes and a plurality of second probes.

The criteria for designing certain sequence-specific primers and probes are well known to persons of ordinary skill in the art. Detailed descriptions of certain primer design that provide for sequence-specific annealing can be found, among other places, in Dieffenbach and Dveksler, PCR Primer, A Laboratory Manual, Cold Spring Harbor Press (1995), and Kwok et al., Nucl. Acids Res. 18:999-1005 (1990). The sequence-specific portions of the primers are of sufficient length to permit specific annealing to complementary sequences in ligation products and amplification products, as appropriate.

According to certain embodiments, a primer set comprises at least one first primer. In certain embodiments, the first primer in that primer set is designed to hybridize with both a 3' primer-specific portion of a ligation or amplification product and a 5' primer-specific portion of the same ligation or amplification product in a sequence-specific manner. In certain embodiments, the primer set further comprises at least one second primer. In certain embodiments, the second primer of a primer set is designed to hybridize with both the complement of the 5' primer-specific portion of that same ligation or amplification product and the complement of the 3' primer-specific portion of that same ligation or amplification product in a sequence-specific manner.

A universal primer or primer set may be employed according to certain embodiments. In certain embodiments, a universal primer or a universal primer set hybridizes with two or more of the probes, ligation products, and/or amplification products in a reaction, as appropriate. In certain embodiments, a universal primer or primer set comprises at least one spanning primer. When universal primer sets are used in certain amplification reactions, such as, but not limited to, PCR, qualitative or quantitative results may be obtained for a broad range of template concentrations.

In certain embodiments involving a ligation reaction and an amplification reaction, one may employ at least one probe and/or at least one primer that includes a minor groove binder attached to it. Certain exemplary minor groove binders and certain exemplary methods of attaching minor groove binders to oligonucleotides are discussed, e.g., in U.S. Pat. Nos. 5,801,155 and 6,084,102. Certain exemplary minor groove binders are those available from Epoch Biosciences, Bothell, Wash. According to certain embodiments, a minor groove binder may be attached to at least one moiety selected from: at least one probe of a ligation probe set; at least one primer of a primer set; and at least one labeled probe.

According to certain embodiments, a minor groove binder is attached to a probe that includes a 3' primer-specific portion. In certain such embodiments, the presence of the minor groove binder facilitates use of a short primer that hybridizes to the 3' primer-specific portion in an amplification reaction. For example, in certain embodiments, the short primer, or segment of the primer that hybridizes to the primer-specific portion or its complement, may have a length of anywhere between 8 and 15 nucleotides.

In certain embodiments, a minor groove binder is attached to at least one of a forward primer and a reverse primer to be used in an amplification reaction. In certain such embodiments, a primer with a minor groove binder attached to it may be a short primer. For example, in certain embodiments, the short primer, or segment of the primer that hybridizes to the primer-specific portion or its complement, may have a length of anywhere between 8 and 15 nucleotides. In certain embodiments, both the forward and reverse primers may have minor groove binders attached to them.

In certain embodiments, one may use minor groove binders as follows in methods that employ a ligation probe set comprising: a first probe comprising a 5' primer specific portion; and a second probe comprising a 3' primer-specific portion. A minor groove binder is attached to the 3' end of the second probe, and a minor groove binder is attached to a primer that hybridizes to the complement of the 5' primer-specific portion of the first probe. In certain such embodiments, the presence of the minor groove binders facilitates use of short forward and reverse primers in an amplification reaction. For example, in certain embodiments, the short primer, or segment of the primer that hybridizes to the primer-specific portion or its complement, may have a length of anywhere between 8 and 15 nucleotides.

One may use any of the arrangements involving minor groove binders discussed above with various methods employing ligation probes with addressable portions as discussed herein. In certain embodiments, one may use such arrangements with different types of ligation and amplification methods. For example, one may use at least one probe and/or at least one primer with an attached minor groove binder in any of a variety of methods employing ligation and amplification reactions. Exemplary methods include, but are not limited to, those discussed in U.S. Pat. No. 6,027,889, PCT Published Patent Application No. WO 01/92579, and U.S. patent application Ser. Nos. 09/584,905 and 10/011,993.

In certain embodiments, one may employ non-natural nucleotides other than the naturally occurring nucleotides A, G, C, T, and U. For example, in certain embodiments, one may employ primer-specific portions and primers and/or addressable portions and labeled probes that comprise pairs of non-natural nucleotides that specifically hybridize to one another and not to naturally occurring nucleotides. Exemplary, but nonlimiting, non-natural nucleotides are discussed, e.g., in Wu et al. *J. Am. Chem. Soc.* (2000) 122: 7621-32; Berger et al. *Nuc. Acids Res.* (2000) 28: 2911-14, Ogawa et al. *J. Am. Chem. Soc.* (2000) 122: 3274-87

The skilled artisan will appreciate that the complement of the disclosed probe, target, and primer sequences, or combinations thereof, may be employed in certain embodiments. For example, without limitation, a genomic DNA sample may comprise both the target sequence and its complement. Thus, in certain embodiments, when a genomic sample is denatured, both the target sequence and its complement are present in the sample as single-stranded sequences. In certain embodiments, ligation probes may be designed to specifically hybridize to an appropriate sequence, either the target sequence or its complement.

Certain Exemplary Ligation Methods

In various embodiments, ligation comprises any enzymatic or chemical process wherein an internucleotide linkage is formed between the opposing ends of nucleic acid sequences. In certain embodiments, the nucleic acid sequences are adjacently hybridized to a template such that their opposing ends are proximal. Additionally, the opposing ends of the annealed nucleic acid sequences are ligated together under suitable conditions. The internucleotide linkage may include, but is not limited to, phosphodiester bond formation. Such bond formation may include, without limitation, those created enzymatically by a DNA or RNA ligase, such as bacteriophage T4 DNA ligase, T4 RNA ligase, T7 DNA ligase, *Thermus thermophilus* (Tth) ligase, *Thermus aquaticus* (Taq) ligase, Tsp AK16D ligase, or *Pyrococcus furiosus* (Pfu) ligase. Other internucleotide linkages include, without limitation, covalent bond formation between appropriate reactive groups such as between an α-haloacyl group and a phosphothioate group to form a thiophosphorylacetylamino group; and between a phosphorothioate and a tosylate or iodide group to form a 5'-phosphorothioester or pyrophosphate linkage.

In certain embodiments, chemical ligation may, under appropriate conditions, occur spontaneously such as by autoligation. Alternatively, in certain embodiments, "activating," condensing, or reducing agents may be used. Examples of activating agents, condensing agents, and reducing agents include, but are not limited to, carbodiimide, cyanogen bromide (BrCN), imidazole, 1-methylimidazole/carbodiimide/cystamine, N-cyanoimidazole, and dithiothreitol (DTT) (see, e.g., Xu et al., Nucl. Acids Res. 27:875-81, 1999; Gryaznov and Letsinger, Nucl. Acids Res. 21: 1403-08, 1993; Gryaznov et al., Nucleic Acid Res. 22:2366-69, 1994; Kanaya and Yanagawa, Biochemistry 25:7423-30, 1986; Luebke and Dervan, Nucl. Acids Res. 20:3005-09, 1992; Sievers and von Kiedrowski, Nature 369:221-24, 1994; Liu and Taylor, Nucl. Acids res. 26:3300-04, 1999; Wang and Kool, Nucl. Acids Res. 22:2326-33, 1994; Purmal et al., Nucl. Acids Res. 20:3713-19, 1992; Ashley and Kushlan, Biochemistry 30:2927-33, 1991; Chu and Orgel, Nucl. Acids Res. 16:3671-91, 1988; Sokolova et al., FEBS Letters 232:153-55, 1988; Naylor and Gilham, Biochemistry 5:2722-28, 1966; Hames and Ellington, Chem. & Biol. 4:595-605, 1997; and U.S. Pat. No. 5,476,930). Non-enzymatic ligation according to certain embodiments may utilize specific reactive groups on the respective 3' and 5' ends of the aligned probes. In certain embodiments, chemical ligation may occur by photoligation. Photoligation includes, but is not limited to: probes comprising nucleotide analogs, including but not limited to, 4-thiothymidine (s4T), 5-vinyluracil and its derivatives, or combination thereof; light in the UV-A range (about 320 nm to about 400 nm); light in the UV-B range (about 290 nm to about 320 nm); combinations of light in the UV-A and UV-B range; light with a wavelength between about 300 nm and about 375 nm; light with a wavelength of about 360 nm to about 370 nm; light with a wavelength of about 364 nm to about 368 nm; and light with a wavelength of about 366 nm. In certain embodiments, photoligation is reversible. Descriptions of photoligation can be found in, for example, Fujimoto et al., Nucl. Acid Symp. Ser. 42:39-40, 1999; Fujimoto et al., Nucl. Acid Res. Suppl. 1: 185-86, 2001; Fujimoto et al., Nucl. Acid. Suppl. 2: 155-56, 2002; and Liu and Taylor, Nucl. Acid Res. 26: 3300-04, 1998.

In certain embodiments, ligation generally comprises at least one cycle of ligation, for example, the sequential procedures of: hybridizing the target-specific portions of a first probe and a second probe, which are suitable for ligation, to their respective complementary regions on a target nucleic acid sequence; ligating the 3' end of the first probe with the 5' end of the second probe to form a ligation product; and denaturing the nucleic acid duplex to separate the ligation product from the target nucleic acid sequence. The cycle may or may not be repeated. For example, without limitation in certain embodiments, thermocycling the ligation reaction may be employed to linearly increase the amount of ligation product.

According to certain embodiments, one may use ligation techniques such as gap-filling ligation, including, without limitation, gap-filling OLA and LCR, bridging oligonucleotide ligation, and correction ligation. Descriptions of these techniques can be found, among other places, in U.S. Pat. No. 5,185,243, published European Patent Applications EP 320308 and EP 439182, published PCT Patent Application WO 90/01069, published PCT Patent Application WO 02/02823, and U.S. Pat. No. 6,511,810.

In certain embodiments, ligation comprises at least one gap-filling procedure in situations where there is a gap between two probes of a ligation probe set when the probes are initially hybridized to a target nucleic acid. In certain embodiments, a DNA polymerase is used to extend the 3'-end of the first probe by one or more nucleotides to fill the gap. Thus, the probes become hybridized adjacent to each other on the target nucleic acid. In certain embodiments, a 'gap oligonucleotide' is hybridized in the gap between the ends of the two probes. In certain such embodiments, the 3'-end of the first probe can be ligated to the 5'-end of the gap oligonucleotide and the 3'-end of the gap oligonucleotide can be ligated to the 5'-end of the second probe. Thus, the probes become hybridized adjacent to each other on the target nucleic acid through the gap oligonucleotide. In certain embodiments, the use of a gap oligonucleotide increases the specificity of an OLA.

In certain embodiments, one may employ poly-deoxy-inosinic-deoxy-cytidylic acid (Poly [d(I-C)]) (Available in Roche Applied Science catalog, 2002) in a ligation reaction. In certain embodiments, one uses any number between 15 to 80 ng/μL of Poly [d(I-C)] in a ligation reaction. In certain embodiments, one uses 30 ng/μL of Poly [d(I-C)] in a ligation reaction.

In certain embodiments, one may use Poly [d(I-C)] in a ligation reaction with various methods employing ligation probes. In certain embodiments, one may use Poly [d(I-C)] with different types of ligation methods. For example, in certain embodiments, one may use Poly [d(I-C)] in a method employing ligation reactions. Exemplary methods include, but are not limited to, those discussed in U.S. Pat. No. 6,027,889, PCT Published Patent Application No. WO 01/92579, and U.S. Patent Application Publication 2004-0121371.

In certain embodiments, in a ligation reaction, one may employ unrelated double-stranded nucleic acid that does not include a sequence that is the same as or is similar to the target nucleic acid sequence that is sought. In certain such embodiments, such double-stranded nucleic acid also will not include a sequence that is the same as or is similar to the sequences of the primer-specific portions of the ligation probes. In certain such embodiments, such double-stranded nucleic acid also will not include a sequence that is the same as or is similar to the sequences of the target-specific portions of the ligation probes. In certain embodiments, one may employ double-stranded poly A and poly T nucleic acid. In certain embodiments, one may employ double-stranded poly G and poly C nucleic acid. In certain embodiments, one may employ nucleic acid from an organism unrelated to the organism from which the target nucleic acid sequence is derived. In certain embodiments, one may employ bacterial nucleic acid. In certain embodiments, one may employ viral DNA. In certain embodiments, one may employ plasmid DNA. In certain embodiments, the double-stranded nucleic acid assists in reducing the amount of ligation that may occur between ligation probes when the sought target nucleic acid sequence is not present.

In certain embodiments, one uses any number between 15 to 80 ng/μL of unrelated double-stranded nucleic acid in a ligation reaction. In certain embodiments, one uses 30 ng/μL of unrelated double-stranded nucleic acid in a ligation reaction.

In certain embodiments, one may use unrelated double-stranded nucleic acid in a ligation reaction employing ligation probes. In certain embodiments, one may use unrelated double-stranded nucleic acid with different types of ligation methods. For example, in certain embodiments, one may use unrelated double-stranded nucleic acid in a method employing ligation reactions. Exemplary methods include, but are not limited to, those discussed in U.S. Pat. No. 6,027,889, PCT Published Patent Application No. WO 01/92579, and U.S. Patent Application Publication No. 2004-0121371.

Exemplary, but nonlimiting ligation reaction conditions may be as follows. In certain embodiments, the ligation reaction temperature may range anywhere from about 45° C. to about 55° C. for anywhere from two to 10 minutes. In certain embodiments, any number from 2 to 100 cycles of ligation are performed. In certain embodiments, 60 cycles of ligation are performed. In certain embodiments, allele specific ligation probes (a probe of a probe set that is specific to a particular allele at a given locus) are in a concentration anywhere from 2 to 100 nM. In certain embodiments, allele specific ligation probes are in a concentration of 50 nM. In certain embodiments, allele specific ligation probes are in a concentration anywhere from 1 to 7 nM. In certain embodiments, locus specific ligation probes (a probe of a probe set that is not specific to a particular allele, but is specific for a given locus) are in a concentration anywhere from 2 to 200 nM. In certain embodiments, locus specific ligation probes are in a concentration of 100 nM. In certain embodiments, fragmented genomic DNA is in a concentration anywhere from 5 ng/μl to 200 ng/μl in the ligation reaction. In certain embodiments, fragmented genomic DNA is in a concentration of 130 ng/μl in the ligation reaction. In certain embodiments, the pH for the ligation reaction is anywhere from 7 to 8. In certain embodiments, the $Mg^{2+}$ concentration is anywhere from 2 to 22 nM. In certain embodiments, the ligase concentration is anywhere from 0.04 to 0.16 U/μl. In certain embodiments, the ligase concentration is anywhere from 0.02 to 0.12 U/μl. In certain embodiments, the $K^+$ concentration is anywhere from 0 to 70 mM. In certain embodiments, the $K^+$ concentration is anywhere from 0 to 20 mM. In certain embodiments, the Poly [d(I-C)] concentration is anywhere from 0 to 30 ng/μl. In certain embodiments, the Poly [d(I-C)] concentration is anywhere from 0 to 20 ng/μl. In certain embodiments, the NAD+ concentration is anywhere from 0.25 to 2.25 mM. In certain embodiments, the ATP concentration is anywhere from 0.1 to 10 mM.

In certain embodiments, one forms a test composition for a subsequent amplification reaction by subjecting a ligation reaction composition to at least one cycle of ligation. In certain embodiments, after ligation, the test composition may be used directly in the subsequent amplification reaction. In certain embodiments, prior to the amplification reaction, the test composition may be subjected to a purification technique that results in a test composition that includes less than all of the components that may have been present after the at least one cycle of ligation. For example, in certain embodiments, one may purify the ligation product.

Purifying the ligation product according to certain embodiments comprises any process that removes at least some unligated probes, target nucleic acid sequences, enzymes, and/or accessory agents from the ligation reaction composition following at least one cycle of ligation. Exemplary processes include, but are not limited to, molecular weight/size exclusion processes, e.g., gel filtration chromatography or dialysis; sequence-specific hybridization-based pullout methods; affinity capture techniques; precipitation; adsorption; and other nucleic acid purification techniques. The skilled artisan will appreciate that purifying the ligation product prior to amplification in certain embodiments reduces the quantity of primers needed to amplify the ligation product, thus reducing the cost of detecting a target sequence. Also, in certain embodiments, purifying the ligation product prior to amplification may decrease possible side reactions during amplification and may reduce competition from unligated probes during hybridization.

Hybridization-based pullout (HBP) according to certain embodiments comprises a process wherein a nucleotide sequence complementary to at least a portion of one probe (or its complement), for example, the primer-specific portion, is bound or immobilized to a solid or particulate pullout support (see, e.g., U.S. Pat. No. 6,124,092). In certain embodiments, a composition comprising ligation product, target sequences, and unligated probes is exposed to the pullout support. The ligation product, under appropriate conditions, hybridizes with the support-bound sequences. The unbound components of the composition are removed, purifying the ligation products from those ligation reaction composition components that do not contain sequences complementary to the sequence on the pullout support. One subsequently removes the purified ligation products from the support and combines them with at least one primer set to form a first amplification reaction composition. The skilled artisan will appreciate that, in certain embodiments, additional cycles of HBP using different complementary sequences on the pullout support may remove all or substantially all of the unligated probes, further purifying the ligation product.

Certain Exemplary Amplification Methods

Amplification according to various embodiments, encompasses a broad range of techniques for amplifying nucleic acid sequences, either linearly or exponentially. Exemplary amplification techniques include, but are not limited to, PCR or any other method employing a primer extension step. Other nonlimiting examples of amplification include, but are not limited to, ligase detection reaction (LDR) and ligase chain reaction (LCR). Amplification methods may comprise thermal-cycling or may be performed isothermally. In various embodiments, the term "amplification product" includes products from any number of cycles of amplification reactions.

In certain embodiments, amplification methods comprise at least one cycle of amplification, for example, but not limited to, the sequential procedures of: hybridizing primers to primer-specific portions of the ligation product or amplification products from any number of cycles of an amplification reaction; synthesizing a strand of nucleotides in a template-dependent manner using a polymerase; and denaturing the newly-formed nucleic acid duplex to separate the strands. The cycle may or may not be repeated.

Descriptions of certain amplification techniques can be found, among other places, in H. Ehrlich et al., Science, 252:1643-50 (1991), M. Innis et al., PCR Protocols: A Guide to Methods and Applications, Academic Press, New York, N.Y. (1990), R. Favis et al., Nature Biotechnology 18:561-64 (2000), and H. F. Rabenau et al., Infection 28:97-102 (2000); Sambrook and Russell, and Ausubel et al., supra.

Primer extension is an amplification process comprising elongating a primer that is annealed to a template in the 5' to 3' direction using a template-dependent polymerase. In certain embodiments, the primer that is extended is a spanning primer. According to certain embodiments, with appropriate buffers, salts, pH, temperature, and nucleotide triphosphates, including analogs and derivatives thereof, a template dependent polymerase incorporates nucleotides complementary to the template strand starting at the 3'-end of an annealed primer, to generate a complementary strand. Detailed descriptions of primer extension according to certain embodiments can be found, among other places, in Sambrook et al., Sambrook and Russell, and Ausubel et al, supra.

Certain embodiments of amplification may employ multiplex PCR, in which multiple target sequences are simultaneously amplified (see, e.g., H. Geada et al., Forensic Sci. Int. 108:31-37 (2000) and D. G. Wang et al., Science 280:1077-82 (1998)).

In certain embodiments, one employs asymmetric PCR. According to certain embodiments, asymmetric PCR comprises an amplification reaction composition comprising (i) at least one primer set in which there is an excess of one primer (relative to the other primer in the primer set); (ii) at least one primer set that comprises only a first primer or only a second primer; (iii) at least one primer set that, during given amplification conditions, comprises a primer that results in amplification of one strand and comprises another primer that is disabled; or (iv) at least one primer set that meets the description of both (i) and (iii) above. Consequently, when the ligation product is amplified, an excess of one strand of the amplification product (relative to its complement) is generated.

In certain embodiments, one may use at least one primer set wherein the melting temperature ($Tm_{50}$) of one of the primers is higher than the $Tm_{50}$ of the other primer. Such embodiments have been called asynchronous PCR (A-PCR). See, e.g., U.S. Pat. No. 6,887,664. In certain embodiments, the $Tm_{50}$ of the first primer is at least 4-15° C. different from the $Tm_{50}$ of the second primer. In certain embodiments, the $Tm_{50}$ of the first primer is at least 8-15° C. different from the $Tm_{50}$ of the second primer. In certain embodiments, the $Tm_{50}$ of the first primer is at least 10-15° C. different from the $Tm_{50}$ of the second primer. In certain embodiments, the $Tm_{50}$ of the first primer is at least 10-12° C. different from the $Tm_{50}$ of the second primer. In certain embodiments, in at least one primer set, the $Tm_{50}$ of the at least one first primer differs from the melting temperature of the at least one second primer by at least about 4° C., by at least about 8° C., by at least about 10° C., or by at least about 12° C.

In certain embodiments of A-PCR, in addition to the difference in $Tm_{50}$ of the primers in a primer set, there is also an excess of one primer relative to the other primer in the primer set. In certain embodiments, there is a five to twenty-fold excess of one primer relative to the other primer in the primer set. In certain embodiments of A-PCR, the primer concentration is at least 50 mM.

In A-PCR according to certain embodiments, one may use conventional PCR in the first cycles such that both primers anneal and both strands are amplified. By raising the temperature in subsequent cycles, however, one may disable the primer with the lower Tm such that only one strand is amplified. Thus, the subsequent cycles of A-PCR in which the primer with the lower Tm is disabled result in asymmetric amplification. Consequently, when the ligation product is amplified, an excess of one strand of the amplification product (relative to its complement) is generated.

According to certain embodiments of A-PCR, the level of amplification can be controlled by changing the number of cycles during the first phase of conventional PCR cycling. In such embodiments, by changing the number of initial conventional cycles, one may vary the amount of the double strands that are subjected to the subsequent cycles of PCR at the higher temperature in which the primer with the lower Tm is disabled.

In certain embodiments, an A-PCR protocol may comprise use of a pair of primers, each of which has a concentration of at least 50 mM. In certain embodiments, conventional PCR, in which both primers result in amplification, is performed for the first 20-30 cycles. In certain embodiments, after 20-30 cycles of conventional PCR, the annealing temperature increases to 66-70° C., and PCR is performed for 5 to 40 cycles at the higher annealing temperature. In such embodiments, the lower Tm primer is disabled during such 5 to 40 cycles at higher annealing temperature. In such embodiments, asymmetric amplification occurs during the second phase of PCR cycles at a higher annealing temperature.

In certain embodiments, one employs asymmetric reamplification. According to certain embodiments, asymmetric reamplification comprises generating single-stranded amplification product in a second amplification process. In certain embodiments, the double-stranded amplification product of a first amplification process serves as the amplification target in the asymmetric reamplification process. In certain embodiments, one may achieve asymmetric reamplification using asynchronous PCR in which initial cycles of PCR conventionally amplify two strands and subsequent cycles are performed at a higher annealing temperature that disables one of the primers of a primer set as discussed above. In certain embodiments, the second amplification reaction composition comprises at least one primer set which comprises the at least one first primer, or the at least one second primer of a primer set, but typically not both. The skilled artisan understands that, in certain embodiments, asymmetric reamplification will also eventually occur if the primers in the primer set are not present in an equimolar ratio. In certain asymmetric reamplification methods, typically only single-stranded amplicons are generated since the second amplification reaction composition comprises only first or second primers from each primer set or a non-equimolar ratio of first and second primers from a primer set.

In certain embodiments, additional polymerase may also be a component of the second amplification reaction composition. In certain embodiments, there may be sufficient residual polymerase from the first amplification composition to synthesize the second amplification product.

Certain methods of optimizing amplification reactions are known to those skilled in the art. For example, it is known that PCR may be optimized by altering times and temperatures for annealing, polymerization, and denaturing, as well as changing the buffers, salts, and other reagents in the reaction composition. Optimization may also be affected by the design of the amplification primers used. For example, the length of the primers, as well as the G-C:A-T ratio may alter the efficiency of primer annealing, thus altering the amplification reaction. See James G. Wetmur, "Nucleic Acid Hybrids, Formation and Structure," in Molecular Biology and Biotechnology, pp. 605-8, (Robert A. Meyers ed., 1995).

In certain amplification reactions, one may use dUTP and uracil-N-glucosidase (UNG). Discussion of use of dUTP and UNG may be found, for example, in Kwok et al., Nature, 339:237-238 (1989); and Longo et al., Gene, 93:125-128 (1990).

To detect whether a particular sequence is present, in certain embodiments, a labeled probe is included in the amplification reaction. According to certain embodiments, the labeled probe indicates the presence or absence (or amount) of a specific nucleic acid sequence in the reaction. These include, but are not limited to, 5'-nuclease probes, cleavage RNA probes, and hybridization dependent probes. In certain embodiments, the labeled probe comprises a fluorescing dye connected to a quenching molecule through a link element, e.g., through a specific oligonucleotide. Examples of such systems are described, e.g., in U.S. Pat. Nos. 5,538,848 and 5,723,591.

In certain embodiments, the amount of labeled probe that gives a fluorescent signal in response to an emitted light typically relates to the amount of nucleic acid produced in the amplification reaction. Thus, in certain embodiments, the amount of fluorescent signal is related to the amount of product created in the amplification reaction. In such embodiments, one can therefore measure the amount of amplification product by measuring the intensity of the fluorescent signal from the fluorescent indicator. According to certain embodiments, one can employ an internal standard to quantify the amplification product indicated by the fluorescent signal. See, e.g., U.S. Pat. No. 5,736,333.

Devices have been developed that can perform a thermal cycling reaction with compositions containing a fluorescent indicator, emit a light beam of a specified wavelength, read the intensity of the fluorescent dye, and display the intensity of fluorescence after each cycle. Devices comprising a thermal cycler, light beam emitter, and a fluorescent signal detector, have been described, e.g., in U.S. Pat. Nos. 5,928,907; 6,015,674; and 6,174,670, and include, but are not limited to the ABI Prism® 7700 Sequence Detection System (Applied Biosystems, Foster City, Calif.) and the ABI GeneAmp® 5700 Sequence Detection System (Applied Biosystems, Foster City, Calif.).

In certain embodiments, each of these functions may be performed by separate devices. For example, if one employs a Q-beta replicase reaction for amplification, the reaction may not take place in a thermal cycler, but could include a light beam emitted at a specific wavelength, detection of the fluorescent signal, and calculation and display of the amount of amplification product.

In certain embodiments, combined thermal cycling and fluorescence detecting devices can be used for precise quantification of target nucleic acid sequences in samples. In certain embodiments, fluorescent signals can be detected and displayed during and/or after one or more thermal cycles, thus permitting monitoring of amplification products as the reactions occur in "real time." In certain embodiments, one can use the amount of amplification product and number of amplification cycles to calculate how much of the target nucleic acid sequence was in the sample prior to amplification.

According to certain embodiments, one could simply monitor the amount of amplification product after a predetermined number of cycles sufficient to indicate the presence of the target nucleic acid sequence in the sample. In various embodiments, one skilled in the art can easily determine, for any given sample type, primer sequence, and reaction condition, how many cycles are sufficient to determine the presence of a given target polynucleotide.

According to certain embodiments, the amplification products can be scored as positive or negative as soon as a given number of cycles is complete. In certain embodiments, the results may be transmitted electronically directly to a database and tabulated. Thus, in certain embodiments, large numbers of samples may be processed and analyzed with less time and labor required.

According to certain embodiments, different labeled probes may distinguish between different target nucleic acid sequences. A non-limiting example of such a probe is a 5'-nuclease fluorescent probe, such as a TaqMan® probe molecule, wherein a fluorescent molecule is attached to a fluorescence-quenching molecule through an oligonucleotide link element. In certain embodiments, the oligonucleotide link element of the 5'-nuclease fluorescent probe binds to a specific sequence of an addressable portion or its complement. In certain embodiments, different 5'-nuclease fluorescent probes, each fluorescing at different wavelengths, can distinguish between different amplification products within the same amplification reaction.

For example, in certain embodiments, one could use two different 5'-nuclease fluorescent probes that fluoresce at two different wavelengths ($WL_A$ and $WL_B$) and that are specific to two different addressable portions of two different ligation products (A' and B', respectively). Ligation product A' is formed if target nucleic acid sequence A is in the sample, and ligation product B' is formed if target nucleic acid sequence B is in the sample. In certain embodiments, ligation product A' and/or B' may form even if the appropriate target nucleic acid sequence is not in the sample, but such ligation occurs to a measurably lesser extent than when the appropriate target nucleic acid sequence is in the sample. After amplification, one can determine which specific target nucleic acid sequences are present in the sample based on the wavelength of signal detected. Thus, if an appropriate detectable signal value of only wavelength $WL_A$ is detected, one would know that the sample includes target nucleic acid sequence A, but not target nucleic acid sequence B. If an appropriate detectable signal value of both wavelengths $WL_A$ and $WL_B$ are detected, one would know that the sample includes both target nucleic acid sequence A and target nucleic acid sequence B.

The following examples are intended for illustration purposes only, and should not be construed as limiting the scope of the teachings in any way.

EXAMPLES

Example 1

Exemplary Spanning Primer Sequences

Exemplary spanning primer sequences are provided below (SEQ ID NOS. 1-4 are disclosed respectively in order of appearance from top to bottom):

```
5' TCGTacGTGGTGGTGCG-GGCCTG ->3' first spanning primer (Tm = ~69° C.)
     |||||||||||| ||||||
   ...TCGCCACCACCACGC CCGGACGTGGACCGGA... ligation product
         5' end 3' end 3'<-GCCACCACCACGCt-AGCATGCACCAA 5' second spanning primer (Tm = ~74° C.)
     ||||||||||||| |||||||||||
   ...AGCGGTGGTGGTGCGa TCGTacGTGGTGGTGCGGGCCTG... amplification product
         5' end 3' end
```

Example 2

Linear Amplification Using Spanning Primers

A target nucleic acid sequence is amplified linearly using a spanning primer. One ng of target nucleic acid sequence is combined with 5 mM $MgCl_2$, 0.5 µM of a spanning primer complementary to both the 3' end and the 5' end of the target nucleic acid sequence, 0.2 mM of each of dATP, dCTP, dGTP, and dTTP, 1× amplification buffer (50 mM KCl, 10 mM Tris-Cl, pH 8.4, 0.1 mg/mL gelatin), and 2.5 U Taq DNA polymerase in a final volume of 100 µL. The target nucleic acid sequence is amplified in an automated thermal cycler using the following protocol: 94° C. for 90 seconds (denaturation), 60° C. for 2 minutes (initial annealing), 72° C. for 3 minutes (extension), followed by 40 cycles of 94° C. for 90 seconds, 60-70° C. for 2 minutes, and 72° C. for 3 minutes. The amplification product is detected.

Example 3

Exponential Amplification Using Spanning Primers

A target nucleic acid sequence is amplified exponentially using two spanning primers. One ng of target nucleic acid sequence is combined with 5 mM $MgCl_2$, 0.5 µM of a first spanning primer complementary to both the 3' end and the 5' end of the target nucleic acid sequence, 0.2 mM of each of dATP, dCTP, dGTP, and dTTP, 1× amplification buffer (50 mM KCl, 10 mM Tris-Cl, pH 8.4, 0.1 mg/mL gelatin), and 2.5 U Taq DNA polymerase in a final volume of 100 µL. Also included in the reaction is 0.5 µM of a second spanning primer. In certain embodiments, the second spanning primer comprises a sequence complementary to both the 3' end of a complement of the target nucleic acid sequence and to the 5' end of the first spanning primer. In certain embodiments, the second spanning primer comprises a sequence complementary to both the 3' end of a complement of the target nucleic acid sequence and to any portion of the first spanning primer.

The target nucleic acid sequence is amplified in an automated thermal cycler using the following protocol: 94° C. for 90 seconds (denaturation), 55-60° C. for 2 minutes (initial annealing), 65-72° C. for 3 minutes (extension), followed by 30-40 cycles of 94° C. for 10-90 seconds, 60-70° C. for 2 minutes, and 72° C. for 3 minutes. The amplification product is detected.

Example 4

Detection of Single Nucleotide Polymorphisms Using Ligation and Linear Amplification The presence of a single nucleotide polymorphism (SNP) in a target nucleic acid sequence is detected using ligation and linear amplification with a spanning primer. A target nucleic acid sequence comprising a SNP is incubated with a ligation probe set comprising (a) a first probe, comprising a first target-specific portion, and (b) a second probe, comprising a second target-specific portion, wherein the probes in each set are suitable for ligation together when hybridized adjacent to one another on the target nucleic acid sequence. One µg of target nucleic acid sequence is combined with 1 µg of the first probe and 1 µg of the second probe, 10 mM Tris-Cl, pH 7.5, 10 mM $MgCl_2$, 10 mM dithiothreitol, and 20 U T4 DNA ligase in a final volume of 20 µL. The reaction is incubated at 15° C. for 12 hours. The resulting ligation product serves as a second target nucleic acid sequence for subsequent amplification.

One ng of ligation product is combined with 5 mM $MgCl_2$, 0.5 µM of a spanning primer complementary to both the 3' end and the 5' end of the ligation product, 0.2 mM of each of dATP, dCTP, dGTP, and dTTP, 1× amplification buffer (50 mM KCl, 10 mM Tris-Cl, pH 8.4, 0.1 mg/mL gelatin), and 2.5 U Taq DNA polymerase in a final volume of 100 µL. The ligation product is amplified in an automated thermal cycler using the following protocol: 94° C. for 90 seconds (denaturation), 55-60° C. for 2 minutes (initial annealing), 72° C. for 3 minutes (extension), followed by 29-40 cycles of 94° C. for 10-90 seconds, 60-70° C. for 2 minutes, and 72° C. for 3 minutes. The presence of the SNP is detected by detecting the presence of the amplification product.

Example 5

Detection of Single Nucleotide Polymorphisms Using Ligation and Exponential Amplification The presence of a single nucleotide polymorphism (SNP) in a target nucleic acid sequence is detected using ligation and exponential amplification with a spanning primer. A target nucleic acid sequence comprising a SNP is incubated with a ligation probe set comprising (a) a first probe, comprising a first target-specific portion, and (b) a second probe, comprising a second target-specific portion, wherein the probes in each set are suitable for ligation together when hybridized adjacent to one another on the target nucleic acid sequence. One µg of target nucleic acid sequence is combined with 1 µg of the first probe and 1 µg of the second probe, 10 mM Tris-Cl, pH 7.5, 10 mM $MgCl_2$, 10 mM dithiothreitol, and 20 U T4 DNA ligase in a final volume of 20 µL. The reaction is incubated at 15° C. for 12 hours. The resulting ligation product serves as a second target nucleic acid sequence for subsequent amplification.

The ligation product is amplified exponentially using two spanning primers. One ng of ligation product is combined with 5 mM $MgCl_2$, 0.5 µM of a first spanning primer complementary to both the 3' end and the 5' end of the ligation product, 0.2 mM of each of dATP, dCTP, dGTP, and dTTP, 1× amplification buffer (50 mM KCl, 10 mM Tris-Cl, pH 8.4, 0.1 mg/mL gelatin), and 2.5 U Taq DNA polymerase in a final volume of 100 µL. Also included in the reaction is 0.5 µM of a second spanning primer. In certain embodiments, the second spanning primer comprises a sequence complementary to both the 3' end of a complement of the ligation product and to the 5' end of the first spanning primer. In certain embodiments, the second spanning primer comprises a sequence complementary to both the 3' end of a complement of the ligation product and to any portion of the first spanning primer. The ligation product is amplified in an automated thermal cycler using the following protocol: 94° C. for 90 seconds (denaturation), 55-60° C. for 2 minutes (initial annealing), 72° C. for 3 minutes (extension), followed by 29-40 cycles of 94° C. for 90 seconds, 60-70° C. for 2 minutes, and 72° C. for 3 minutes. The presence of the SNP is detected by detecting the presence of the amplification product.

The foregoing examples are not intended to limit the scope of the teachings herein.

What is claimed is:

1. A method for determining whether at least one target nucleic acid sequence is present in a sample, comprising:

forming a ligation reaction composition comprising the sample, and a ligation probe set for each target nucleic acid sequence, the probe set comprising (a) a first probe, comprising a first target-specific portion, and (b) a second probe, comprising a second target-specific portion, wherein the probes in each set are suitable for ligation together when hybridized adjacent to one another on the complementary target nucleic acid sequence;

forming a first test composition by subjecting the ligation reaction composition to at least one cycle of ligation, wherein adjacently hybridizing complementary probes are ligated to one another to form a ligation product comprising the first probe and the second probe if a target nucleic acid sequence is present in the sample;

forming an amplification reaction composition comprising:

at least some of the first test composition;

a polymerase;

a first primer comprising (i) a sequence complementary to the 5' end of the ligation product and (ii) a sequence complementary to the 3' end of the ligation product;

forming a second test composition by subjecting the amplification reaction composition to at least one amplification reaction, wherein the second test composition comprises at least one amplification product if a target nucleic acid sequence is present in the sample; and wherein the 5' end of the ligation product and the 3' end of the ligation product are not ligated to one another; and determining whether the at least one target nucleic acid sequence is present by detecting at least one amplification product.

2. The method of claim 1, wherein the amplification reaction composition further comprises a second primer comprising (i) a sequence complementary to the 3' end of a complement of the target nucleic acid sequence and (ii) a sequence complementary to any portion of the first primer.

3. The method of claim 1, wherein the amplification reaction composition further comprises a second primer comprising (i) a sequence complementary to the 3' end of a complement of the target nucleic acid sequence and (ii) a sequence complementary to the 5' end of the first primer.

4. The method of claim 2, wherein the second primer comprises a thymidine between (i) the sequence complementary to the 3' end of a complement of the target nucleic acid sequence and (ii) the sequence complementary to any portion of the first primer.

5. The method of claim 3, wherein the second primer comprises a thymidine between (i) the sequence complementary to the 3' end of a complement of the target nucleic acid sequence and (ii) the sequence complementary to the 5' end of the first primer.

6. The method of claim 1, wherein each probe set further comprises a third probe, comprising a third target specific portion, wherein the third target specific portion differs from the first target specific portion by at least one nucleotide.

7. The method of claim 1, wherein each target nucleic acid sequence contains at least one pivotal nucleotide, such that a first allele of the target nucleic acid sequence comprises a first nucleotide at the at least one pivotal nucleotide, and a second allele of the target nucleic acid sequence comprises a second nucleotide at the at least one pivotal nucleotide, and wherein the first nucleotide and the second nucleotide are different.

8. The method of claim 7, wherein each probe set further comprises a third probe, comprising a third target specific portion, wherein the third target specific portion differs from the first target specific portion by at least one nucleotide, and wherein the first target specific portion comprises at least one pivotal complement for the first allele of the target nucleic acid sequence and the third target specific portion comprises at least one pivotal complement for the second allele of the target nucleic acid sequence.

9. The method of claim 8, wherein the first probe comprises a first addressable specific portion and the third probe comprises a second addressable specific portion, such that the presence of the first addressable specific portion in at least one amplification product indicates the presence of the first allele of the target nucleic acid sequence and the presence of the second addressable specific portion in at least one amplification product indicates the presence of the second allele of the target nucleic acid sequence.

10. The method of claim 9, wherein the second probe comprises a third addressable specific portion, such that the presence of the third addressable specific portion in at least one amplification product indicates the presence of the target nucleic acid sequence.

11. The method of claim 10, wherein at least one amplification product comprises the first or second addressable specific portion within four to ten nucleotides of the third addressable specific portion.

12. The method of claim 10, wherein the amplification reaction composition further comprises a second primer comprising a sequence complementary to the 3' end of a complement of the target nucleic acid sequence.

13. The method of claim 12, wherein the detecting comprises:
exposing at least some of the second test composition to (a) a first detection probe comprising (i) a sequence complementary to the first addressable specific portion and (ii) a sequence complementary to the third addressable specific portion; and (b) a second detection probe comprising (i) a sequence complementary to the second addressable specific portion and (ii) a sequence complementary to the third addressable specific portion; and
detecting whether the first detection probe hybridizes to at least one amplification product to determine whether the first allele of the target nucleic acid sequence is present and detecting whether the second detection probe hybridizes to at least one amplification product to determine whether the second allele of the target nucleic acid sequence is present.

14. The method of claim 12, wherein the detecting comprises:
exposing at least some of the second test composition to a first restriction endonuclease and a second restriction endonuclease to produce a third test composition which comprises a cleavage product if at least one amplification product is present in the second test composition, wherein the first addressable specific portion has a recognition site for the first restriction endonuclease, the second addressable specific portion has a recognition site for the second restriction endonuclease, and wherein the cleavage site for the first restriction endonuclease and the second restriction endonuclease is within the third addressable specific portion of at least one amplification product;
exposing the third test composition to a first detection probe comprising a sequence complementary to the first addressable specific portion and to a second detection probe comprising a sequence complementary to the second addressable specific portion;
separating the hybridized cleavage product from unhybridized first detection probes and second detection probes; and
detecting the presence or absence of the cleavage product.

15. The method of claim 12, wherein the detecting comprises:
forming a second ligation reaction composition comprising at least some of the second test composition, a first detection probe comprising a sequence complementary to the first addressable specific portion and a first label, a second detection probe comprising a second label and a sequence complementary to the second addressable specific portion, and a third detection probe comprising a sequence complementary to the third addressable specific portion, wherein the first detection probe and the third detection probe are suitable for ligation together when hybridized adjacent to one another on at least one amplification product, and wherein the second probe and the third probe are suitable for ligation together when hybridized adjacent to one another on at least one amplification product;
forming a third test composition by subjecting the second ligation reaction composition to at least one cycle of ligation, wherein adjacently hybridizing complementary detection probes are ligated to one another to form a second ligation product comprising the first detection probe or the second detection probe and the third detection probe;
separating the second ligation product from unligated first detection probes, second detection probes, and third detection probes; and
detecting the presence or absence of the first label and the second label.

16. The method of claim 12, wherein the detecting comprises:
forming a second amplification reaction composition comprising at least some of the second test composition, a detection probe comprising a sequence complementary to the third addressable specific portion, a first POR primer comprising a first label and a sequence complementary to the first addressable specific portion, a second PCR primer comprising a second label and a sequence complementary to the second addressable specific portion, and a polymerase, wherein the detection probe is attached to a solid support;
subjecting the second amplification reaction composition to at least one amplification reaction; and
detecting the presence or absence of the first label and the second label.

17. The method of claim 12, wherein the detecting comprises:
forming a second ligation reaction composition comprising at least some of the second test composition, a first detection probe comprising a first label and a sequence complementary to the first addressable specific portion, a second detection probe comprising a second label and a sequence complementary to the second addressable specific portion, and a third detection probe comprising a sequence complementary to the third addressable specific portion, wherein the first detection probe and the third detection probe are suitable for ligation together when hybridized adjacent to one another on at least one amplification product, and wherein the second detection probe and the third detection probe are suitable for ligation together when hybridized adjacent to one another on at least one amplification product, and wherein the third detection probe is attached to a solid support;

forming a third test composition by subjecting the ligation reaction composition to at least one cycle of ligation, wherein adjacently hybridizing complementary probes are ligated to one another to form a second ligation product comprising the first detection probe or the second detection probe and the third detection probe;

separating the second ligation product from unligated first detection probes and second detection probes; and detecting the presence or absence of the first label and the second label.

18. The method of claim 12, wherein the detecting comprises:

exposing the second test composition to at least two different sequence-specific mobility-modifiers, wherein each different mobility-modifier is capable of sequence-specific binding to a different addressable specific portion and comprises (a) a tag complement for specifically binding the addressable specific portion of at least one amplification product, and (b) a tail which imparts to each mobility modifier a mobility that is distinctive relative to the mobilities of one or more other of the at least two different mobility-modifiers in a mobility-dependent analysis technique;

removing mobility-modifiers that are not sequence-specifically bound to the amplification reaction products from mobility-modifiers that are sequence-specifically bound to at least one amplification product;

releasing the sequence-specifically bound mobility-modifiers from the amplification reaction products;

subjecting the released mobility-modifiers to a mobility-dependent analysis technique; and detecting one or more target nucleic acid sequences by detecting distinctive positions of the mobility-modifiers.

19. The method of claim 18, wherein at least one sequence-specific mobility modifier comprises a label.

20. The method of claim 18, wherein the mobility-dependent analysis technique is electrophoresis.

21. The method of claim 1, wherein the 3' end of the second probe is blocked.

22. The method of claim 1, wherein the amplification reaction comprises an annealing step that takes place at a predetermined annealing temperature, and wherein the annealing temperature is 70° C. or greater.

23. The method of claim 1, wherein the amplification reaction comprises an annealing step that takes place at a predetermined annealing temperature, and wherein the annealing temperature of two first cycles of amplification is 65° C., and is increased to at least 70° C. for subsequent cycles of amplification.

24. A method for determining whether at least one target nucleic acid sequence is present in a sample comprising:
  (a) forming a reaction composition comprising:
    the sample;
    a ligation probe set for each target nucleic acid sequence, the probe set comprising (i) at least one first probe, comprising a first target-specific portion and (ii) at least one second probe, comprising a second target-specific portion,
    wherein the probes in each set are suitable for ligation together to form a ligation product when hybridized adjacent to one another on a complementary target nucleic acid sequence;
    a polymerase; and
    a first primer comprising (i) a sequence complementary to the 5' end of the ligation product and (ii) a sequence complementary to the 3 end of the ligation product;
  (b) subjecting the reaction composition to at least one cycle of ligation, wherein adjacently hybridizing complementary probes are ligated to one another to form a ligation product comprising the first probe and the second probe if a target nucleic acid sequence is present in the sample; and wherein the 5' end of the ligation product and the 3' end of the ligation product are not ligated to one another;
  (c) after the at least one cycle of ligation, subjecting the reaction composition to at least one amplification reaction to form at least one amplification product if a target nucleic acid sequence is present in the sample; and
  (d) determining whether the at least one target nucleic acid sequence is present by detecting at least one amplification product.

25. The method of claim 24, further comprising a second primer comprising (i) a sequence complementary to the 3' end of a complement of the target nucleic acid sequence product and (ii) a sequence complementary to the 5' end of the first primer.

* * * * *